US012715922B2

(12) United States Patent
Koide et al.

(10) Patent No.: US 12,715,922 B2
(45) **Date of Patent: *Aug. 25, 2026**

(54) ANTI-GALECTIN-9 ANTIBODIES AND USES THEREOF

(71) Applicants: New York University, New York, NY (US); PureTech LYT, Inc., Boston, MA (US)

(72) Inventors: Shohei Koide, New York, NY (US); George Miller, New York, NY (US); Akiko Koide, New York, NY (US); Linxiao Chen, New York, NY (US); Aleksandra Filipovic, London (GB); Eric Elenko, Boston, MA (US); Joseph Bolen, Boston, MA (US)

(73) Assignees: New York University, New York, NY (US); PureTech LYT, Inc., Boston, MA (US)

( * ) Notice: Subject to any disclaimer, the term of this patent is extended or adjusted under 35 U.S.C. 154(b) by 1089 days.

This patent is subject to a terminal disclaimer.

(21) Appl. No.: 17/598,215

(22) PCT Filed: Mar. 25, 2020

(86) PCT No.: PCT/US2020/024767

§ 371 (c)(1),
(2) Date: Sep. 24, 2021

(87) PCT Pub. No.: WO2020/198390

PCT Pub. Date: Oct. 1, 2020

(65) Prior Publication Data

US 2022/0204629 A1 Jun. 30, 2022

Related U.S. Application Data

(60) Provisional application No. 62/959,606, filed on Jan. 10, 2020, provisional application No. 62/946,898, filed on Dec. 11, 2019, provisional application No. 62/931,140, filed on Nov. 5, 2019, provisional application No. 62/931,159, filed on Nov. 5, 2019, provisional application No. 62/841,730, filed on May 1, 2019, provisional application No. 62/823,458, filed on Mar. 25, 2019.

(51) Int. Cl.

| | |
|---|---|
| ***C07K 16/28*** | (2006.01) |
| ***A61K 31/337*** | (2006.01) |
| ***A61K 31/7068*** | (2006.01) |
| ***A61K 39/395*** | (2006.01) |
| ***A61P 35/00*** | (2006.01) |

(52) U.S. Cl.

CPC ........ *C07K 16/2851* (2013.01); *A61K 31/337* (2013.01); *A61K 31/7068* (2013.01); *A61K 39/3955* (2013.01); *A61P 35/00* (2018.01); *C07K 16/2818* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/622* (2013.01)

(58) Field of Classification Search

CPC .............. A61K 31/337; A61K 31/7068; A61K 39/3955; A61P 35/00; C07K 16/2851; C07K 16/2818; C07K 2317/24; C07K 2317/51; C07K 2317/515; C07K 2317/56; C07K 2317/565; C07K 2317/622

See application file for complete search history.

(56) References Cited

U.S. PATENT DOCUMENTS

| | | | | |
|---|---|---|---|---|
| 6,737,056 | B1 * | 5/2004 | Presta | C07K 16/18 530/387.3 |
| 7,625,560 | B2 * | 12/2009 | Basi | C07K 16/18 435/7.1 |
| 10,344,091 | B2 * | 7/2019 | Koide | C07K 16/2827 |
| 10,450,374 | B2 * | 10/2019 | Koide | A61P 35/00 |
| 2007/0237764 | A1 | 10/2007 | Birtalan et al. | |
| 2008/0181888 | A1 | 7/2008 | Ambrose et al. | |
| 2009/0023143 | A1 | 1/2009 | Hirashima et al. | |
| 2009/0191209 | A1 | 7/2009 | Kelley et al. | |
| 2011/0151490 | A1 | 6/2011 | Hillman et al. | |
| 2012/0148599 | A1 | 6/2012 | Atwal et al. | |
| 2013/0323176 | A1 | 12/2013 | Hirashima et al. | |
| 2014/0234320 | A1 | 8/2014 | Croft et al. | |
| 2014/0242095 | A1 | 8/2014 | Wang et al. | |
| 2014/0378531 | A1 | 12/2014 | Miller et al. | |
| 2015/0265701 | A1 | 9/2015 | Ralph | |

(Continued)

FOREIGN PATENT DOCUMENTS

| | | |
|---|---|---|
| WO | 2009150275 A1 | 12/2009 |
| WO | 2011159877 A2 | 12/2011 |

(Continued)

OTHER PUBLICATIONS

Barjon, C. et al., A novel Monoclonal antibody for detection of galectin-9 in tissue sections: application to human tissues infected by oncogenic viruses, Infectious Agents and Cancer, 2012, vol. 7, No. 16, pp. 1-11.

(Continued)

*Primary Examiner* — Julie Wu

(74) *Attorney, Agent, or Firm* — Hodgson Russ LLP

(57) ABSTRACT

Disclosed herein are anti-Galectin-9 antibodies and methods of using in modulating (e.g., increasing) immune responses in a subject, either taken alone or in combination with an immune checkpoint inhibitor, such as a PD-1 inhibitor.

15 Claims, 30 Drawing Sheets

Specification includes a Sequence Listing.

(56) References Cited

U.S. PATENT DOCUMENTS

| | | | | |
|---|---|---|---|---|
| 2016/0209425 | A1 | 7/2016 | Miller et al. | |
| 2017/0283499 | A1 | 10/2017 | Delhem et al. | |
| 2017/0343552 | A1 | 11/2017 | Hodi et al. | |
| 2018/0044422 | A1* | 2/2018 | Miller | C12N 15/1138 |
| 2018/0251532 | A1 | 9/2018 | Gavathiotis et al. | |
| 2019/0127472 | A1 | 5/2019 | Koide et al. | |
| 2019/0256604 | A1 | 8/2019 | Koide et al. | |
| 2022/0204629 | A1 | 6/2022 | Koide et al. | |
| 2024/0287195 | A1* | 8/2024 | Filipovic | G01N 33/57476 |

FOREIGN PATENT DOCUMENTS

| | | | |
|---|---|---|---|
| WO | 2015035112 | A1 | 3/2015 |
| WO | 2015164330 | A1 | 10/2015 |
| WO | 2016008005 | A1 | 1/2016 |
| WO | 2016041945 | A1 | 3/2016 |
| WO | 2016061504 | A2 | 4/2016 |
| WO | 2017202962 | A1 | 11/2017 |
| WO | 2018/053597 | A1 | 3/2018 |
| WO | 2019084553 | A1 | 5/2019 |
| WO | 2020014465 | A1 | 1/2020 |
| WO | 2020223702 | A1 | 11/2020 |

OTHER PUBLICATIONS

Daley, D., et al, Dectin 1 activation on macrophages by galectin 9 promotes pancreatic carcinoma and peritumoral immune tolerance, Nature Medicine, Apr. 10, 2017, vol. 23, No. 5, pp. 556-567.

Ikeda et al., Blocking Effect of Anti-Dectin-1 Antibodies on the Anti-tumor Activity of 1,3-Beta-Glucan and the Binding of Dectin-1 to 1,3-Beta-Glucan, Biological and Pharmaceutical Bulletin, Jun. 4, 2007, vol. 30, No. 8, pp. 1384-1389.

Kadowaki, T., et al., Galectin-9 signaling prolongs survival in murine lung cancer by inducing macrophages to differentiate into plasmacytoid dendritic cell-like macrophages, Clinical immunology, Nov. 25, 2011, vol. 142, No. 3, pp. 296-307.

Long, Y. et al., Research progress on the expression and function of Galectin-9 in various tumors, Journal of Medical Research, Dec. 31, 2015, vol. 44, No. 9, pp. 169-172.

Luheshi et al., Transformation of the tumour microenvironment by a CD40 agonist antibody correlates with improved responses to PD-L1 blockade in a mouse orthotopic pancreatic tumour model, Oncotarget, Feb. 23, 2016, vol. 7, No. 14, pp. 18508-18520.

Orth, M., et al., Pancreatic ductal adenocarcinoma: biological hallmarks, current status, and future perspectives of combined modality treatment approaches, Radiation Oncology, Aug. 8, 2019, vol. 14, No. 1, article 141, pp. 1-20.

Seifert, L., et al., Dectin-1 regulates hepatic fibrosis and hepatocarcinogenesis by suppressing TLR4 signaling pathways, Cell Reports, Dec. 1, 2015, vol. 13, No. 9, pp. 1909-1921.

Seyed, M.A., et al, A comprehensive review on the chemotherapeutic potential of piceatannol for cancer treatment, with mechanistic insights, Journal of Agricultural and Food Chemistry, Jan. 26, 2016, vol. 64, No. 4, pp. 725-737.

Tang et al., microRNA-22 acts as a metastasis suppressor by targeting metadherin in gastric cancer, Molecular Medicine Reports, Oct. 16, 2014, vol. 11, No. 1, pp. 454-460.

Tureci, O. et al., Molecular Definition of a Novel Human Galectin Which is Immunogenic in Patients with Hodgkin's Disease, The Journal of Biological Chemistry, Mar. 7, 1997, vol. 272, No. 10. pp. 6416-6422.

Winograd et al., Induction of T-Cell Immunity Overcomes Complete Resistance to PD-1 and CTLA-4 Blockade and Improves Survival in Pancreatic Carcinoma, Cancer Immunology Research, Apr. 2015, vol. 3, No. 4, pp. 399-411.

Yan, H., et al., Targeting C-type lectin receptors for cancer immunity, Frontiers in Immunology, Aug. 24, 2015, vol. 6, No. 408, pp. 1-9.

Yang, Q., et al., microRNA-22 downregulation of galectin-9 influences lymphocyte apoptosis and tumor cell proliferation in liver cancer, Oncology Reports, Jul. 31, 2015, vol. 34, No. 4, pp. 1771-1778.

Bertino, P., et al., Targeting the C-terminus of galectin-9 induces mesothelioma apoptosis and M2 macrophage depletion, Oncoimmunology, Apr. 17, 2019, vol. 8, No. 8, 12 pages.

Lee, C.V., et al., Chain H, Cb3s Fab Heavy Chain, Protein Data bank entry 2HFG_H, (online). National Institute of Biotechnology Information, Feb. 11, 2013, 3 pages. https://www.ncbi.nlm.nih.gov/protein/2HFG_H.

Tyson, K.L., et al., anti-rozanolixizumab immunoglobulin heavy chain, partial [synthetic construct], Genbank entry AYI49806.1, National Institute of Biotechnology Information, Feb. 22, 2019, 2 pages. https://www.ncbi.nlm.nih.gov/protein/AYI49806.1.

Niki, T., et al., Plasma Galectin-9 Concentrations in Normal and Diseased Condition., Cellular Physiology and Biochemistry, Nov. 3, 2018, vol. 50, No. 5, pp. 1856-1868.

Miyanishi, N., et al., Carbohydrate-recognition domains of galectin-9 are involved in intermolecular interaction with galectin-9 itself and other members of the galectin family, Glycobiology, Jan. 12, 2007, vol. 17, No. 4, pp. 423-432.

* cited by examiner n = 8 / arm
** p< 0.02
NS; p = 0.80

$p<0.05$

SEQUENCE LISTING

```
<160> NUMBER OF SEQ ID NOS: 62

<210> SEQ ID NO 1
<211> LENGTH: 355
<212> TYPE: PRT
<213> ORGANISM: Homo sapiens

<400> SEQUENCE: 1

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                165                 170                 175

Arg Arg Gln Lys Pro Pro Gly Val Trp Pro Ala Asn Pro Ala Pro Ile
            180                 185                 190

Thr Gln Thr Val Ile His Thr Val Gln Ser Ala Pro Gly Gln Met Phe
        195                 200                 205

Ser Thr Pro Ala Ile Pro Pro Met Met Tyr Pro His Pro Ala Tyr Pro
    210                 215                 220

Met Pro Phe Ile Thr Thr Ile Leu Gly Gly Leu Tyr Pro Ser Lys Ser
225                 230                 235                 240

Ile Leu Leu Ser Gly Thr Val Leu Pro Ser Ala Gln Arg Phe His Ile
```

```
                245                 250                 255

Asn Leu Cys Ser Gly Asn His Ile Ala Phe His Leu Asn Pro Arg Phe
            260                 265                 270

Asp Glu Asn Ala Val Val Arg Asn Thr Gln Ile Asp Asn Ser Trp Gly
        275                 280                 285

Ser Glu Glu Arg Ser Leu Pro Arg Lys Met Pro Phe Val Arg Gly Gln
    290                 295                 300

Ser Phe Ser Val Trp Ile Leu Cys Glu Ala His Cys Leu Lys Val Ala
305                 310                 315                 320

Val Asp Gly Gln His Leu Phe Glu Tyr Tyr His Arg Leu Arg Asn Leu
                325                 330                 335

Pro Thr Ile Asn Arg Leu Glu Val Gly Gly Asp Ile Gln Leu Thr His
            340                 345                 350

Val Gln Thr
        355


<210> SEQ ID NO 2
<211> LENGTH: 323
<212> TYPE: PRT
<213> ORGANISM: Homo sapiens

<400> SEQUENCE: 2

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Phe His Ile
    210                 215                 220

Asn Leu Cys Ser Gly Asn His Ile Ala Phe His Leu Asn Pro Arg Phe
225                 230                 235                 240

Asp Glu Asn Ala Val Val Arg Asn Thr Gln Ile Asp Asn Ser Trp Gly
                245                 250                 255
```

```
Ser Glu Glu Arg Ser Leu Pro Arg Lys Met Pro Phe Val Arg Gly Gln
            260                 265                 270

Ser Phe Ser Val Trp Ile Leu Cys Glu Ala His Cys Leu Lys Val Ala
        275                 280                 285

Val Asp Gly Gln His Leu Phe Glu Tyr Tyr His Arg Leu Arg Asn Leu
    290                 295                 300

Pro Thr Ile Asn Arg Leu Glu Val Gly Gly Asp Ile Gln Leu Thr His
305                 310                 315                 320

Val Gln Thr


<210> SEQ ID NO 3
<211> LENGTH: 148
<212> TYPE: PRT
<213> ORGANISM: Homo sapiens

<400> SEQUENCE: 3

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln
145


<210> SEQ ID NO 4
<211> LENGTH: 138
<212> TYPE: PRT
<213> ORGANISM: Homo sapiens

<400> SEQUENCE: 4

Tyr Pro His Pro Ala Tyr Pro Met Pro Phe Ile Thr Thr Ile Leu Gly
1               5                   10                  15

Gly Leu Tyr Pro Ser Lys Ser Ile Leu Leu Ser Gly Thr Val Leu Pro
            20                  25                  30

Ser Ala Gln Arg Phe His Ile Asn Leu Cys Ser Gly Asn His Ile Ala
        35                  40                  45

Phe His Leu Asn Pro Arg Phe Asp Glu Asn Ala Val Val Arg Asn Thr
    50                  55                  60

Gln Ile Asp Asn Ser Trp Gly Ser Glu Glu Arg Ser Leu Pro Arg Lys
65                  70                  75                  80

Met Pro Phe Val Arg Gly Gln Ser Phe Ser Val Trp Ile Leu Cys Glu
                85                  90                  95

Ala His Cys Leu Lys Val Ala Val Asp Gly Gln His Leu Phe Glu Tyr
```

```
            100                 105                 110

Tyr His Arg Leu Arg Asn Leu Pro Thr Ile Asn Arg Leu Glu Val Gly
        115                 120                 125

Gly Asp Ile Gln Leu Thr His Val Gln Thr
    130                 135


<210> SEQ ID NO 5
<211> LENGTH: 147
<212> TYPE: PRT
<213> ORGANISM: Mus musculus

<400> SEQUENCE: 5

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe
145


<210> SEQ ID NO 6
<211> LENGTH: 98
<212> TYPE: PRT
<213> ORGANISM: Mus musculus

<400> SEQUENCE: 6

Leu Cys Ser Gly Asn His Ile Ala Phe His Leu Asn Pro Arg Phe Asp
1               5                   10                  15

Glu Asn Ala Val Val Arg Asn Thr Gln Ile Asp Asn Ser Trp Gly Ser
            20                  25                  30

Glu Glu Arg Ser Leu Pro Arg Lys Met Pro Phe Val Arg Gly Gln Ser
        35                  40                  45

Phe Ser Val Trp Ile Leu Cys Glu Ala His Cys Leu Lys Val Ala Val
    50                  55                  60

Asp Gly Gln His Leu Phe Glu Tyr Tyr His Arg Leu Arg Asn Leu Pro
65                  70                  75                  80

Thr Ile Asn Arg Leu Glu Val Gly Gly Asp Ile Gln Leu Thr His Val
                85                  90                  95

Gln Thr


<210> SEQ ID NO 7
<211> LENGTH: 110
<212> TYPE: PRT
<213> ORGANISM: Homo sapiens
```

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Asp Ser Asn
                85                  90                  95

Pro Ile Thr Phe Gly Gln Gly Thr Lys Val Glu Ile Lys Arg
            100                 105                 110
```

<210> SEQ ID NO 8
<211> LENGTH: 123
<212> TYPE: PRT
<213> ORGANISM: Homo sapiens

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Ser Ser Ser Ser Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ser Thr Tyr Ser Ser Lys Trp Val Trp Gly Met Asp Tyr
            100                 105                 110

Trp Gly Gln Gly Thr Leu Val Thr Val Ser Ser
        115                 120
```

<210> SEQ ID NO 9
<211> LENGTH: 108
<212> TYPE: PRT
<213> ORGANISM: Homo sapiens

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Ser Thr Asp Pro Ile
                85                  90                  95

Thr Phe Gly Gln Gly Thr Lys Val Glu Ile Lys Arg
            100                 105


<210> SEQ ID NO 10
<211> LENGTH: 124
<212> TYPE: PRT
<213> ORGANISM: Homo sapiens

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Ser Tyr Pro Ser Trp Trp Pro Tyr Arg Gly Met Asp
            100                 105                 110

Tyr Trp Gly Gln Gly Thr Leu Val Thr Val Ser Ser
        115                 120


<210> SEQ ID NO 11
<211> LENGTH: 108
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Asp Pro Ile
                85                  90                  95

Thr Phe Gly Gln Gly Thr Lys Val Glu Ile Lys Arg
            100                 105


<210> SEQ ID NO 12
<211> LENGTH: 124
<212> TYPE: PRT
<213> ORGANISM: Homo sapiens

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
```

```
            20                  25                  30

Ser Ile His Trp Val Arg Gln Ala Pro Gly Lys Gly Leu Glu Trp Val
        35                  40                  45

Ala Tyr Ile Ser Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Ser Tyr Pro Ser Trp Ser Pro Tyr Arg Gly Met Asp
            100                 105                 110

Tyr Trp Gly Gln Gly Thr Leu Val Thr Val Ser Ser
        115                 120


<210> SEQ ID NO 13
<211> LENGTH: 11
<212> TYPE: PRT
<213> ORGANISM: Homo sapiens

<400> SEQUENCE: 13

Arg Ala Ser Gln Ser Val Ser Ser Ala Val Ala
1               5                   10


<210> SEQ ID NO 14
<211> LENGTH: 7
<212> TYPE: PRT
<213> ORGANISM: Homo sapiens

<400> SEQUENCE: 14

Ser Ala Ser Ser Leu Tyr Ser
1               5


<210> SEQ ID NO 15
<211> LENGTH: 11
<212> TYPE: PRT
<213> ORGANISM: Homo sapiens

<400> SEQUENCE: 15

Gln Gln Ser Tyr Tyr Asp Ser Asn Pro Ile Thr
1               5                   10


<210> SEQ ID NO 16
<211> LENGTH: 9
<212> TYPE: PRT
<213> ORGANISM: Homo sapiens

<400> SEQUENCE: 16

Phe Thr Val Ser Ser Ser Ser Ile His
1               5


<210> SEQ ID NO 17
<211> LENGTH: 17
<212> TYPE: PRT
<213> ORGANISM: Homo sapiens

<400> SEQUENCE: 17

Tyr Ile Tyr Pro Tyr Ser Ser Ser Ser Ser Tyr Ala Asp Ser Val Lys
1               5                   10                  15

Gly


<210> SEQ ID NO 18
```

<211> LENGTH: 14
<212> TYPE: PRT
<213> ORGANISM: Homo sapiens

<400> SEQUENCE: 18

Tyr Ser Thr Tyr Ser Ser Lys Trp Val Trp Gly Met Asp Tyr
1 5 10

<210> SEQ ID NO 19
<211> LENGTH: 11
<212> TYPE: PRT
<213> ORGANISM: Homo sapiens

<400> SEQUENCE: 19

Arg Ala Ser Gln Ser Val Ser Ser Ala Val Ala
1 5 10

<210> SEQ ID NO 20
<211> LENGTH: 7
<212> TYPE: PRT
<213> ORGANISM: Homo sapiens

<400> SEQUENCE: 20

Ser Ala Ser Ser Leu Tyr Ser
1 5

<210> SEQ ID NO 21
<211> LENGTH: 9
<212> TYPE: PRT
<213> ORGANISM: Homo sapiens

<400> SEQUENCE: 21

Gln Gln Ser Ser Thr Asp Pro Ile Thr
1 5

<210> SEQ ID NO 22
<211> LENGTH: 9
<212> TYPE: PRT
<213> ORGANISM: Homo sapiens

<400> SEQUENCE: 22

Phe Thr Val Ser Ser Ser Ser Ile His
1 5

<210> SEQ ID NO 23
<211> LENGTH: 17
<212> TYPE: PRT
<213> ORGANISM: Homo sapiens

<400> SEQUENCE: 23

Tyr Ile Ser Ser Ser Ser Gly Tyr Thr Tyr Tyr Ala Asp Ser Val Lys
1 5 10 15

Gly

<210> SEQ ID NO 24
<211> LENGTH: 15
<212> TYPE: PRT
<213> ORGANISM: Homo sapiens

<400> SEQUENCE: 24

Tyr Trp Ser Tyr Pro Ser Trp Trp Pro Tyr Arg Gly Met Asp Tyr
1 5 10 15

<210> SEQ ID NO 25

<211> LENGTH: 11
<212> TYPE: PRT
<213> ORGANISM: Homo sapiens

<400> SEQUENCE: 25

```
Arg Ala Ser Gln Ser Val Ser Ser Ala Val Ala
1               5                   10
```

<210> SEQ ID NO 26
<211> LENGTH: 7
<212> TYPE: PRT
<213> ORGANISM: Homo sapiens

<400> SEQUENCE: 26

```
Ser Ala Ser Ser Leu Tyr Ser
1               5
```

<210> SEQ ID NO 27
<211> LENGTH: 9
<212> TYPE: PRT
<213> ORGANISM: Homo sapiens

<400> SEQUENCE: 27

```
Gln Gln Ser Ser Thr Asp Pro Ile Thr
1               5
```

<210> SEQ ID NO 28
<211> LENGTH: 9
<212> TYPE: PRT
<213> ORGANISM: Homo sapiens

<400> SEQUENCE: 28

```
Phe Thr Val Ser Ser Ser Ser Ile His
1               5
```

<210> SEQ ID NO 29
<211> LENGTH: 17
<212> TYPE: PRT
<213> ORGANISM: Homo sapiens

<400> SEQUENCE: 29

```
Tyr Ile Ser Ser Ser Ser Gly Tyr Thr Tyr Tyr Ala Asp Ser Val Lys
1               5                   10                  15

Gly
```

<210> SEQ ID NO 30
<211> LENGTH: 15
<212> TYPE: PRT
<213> ORGANISM: Homo sapiens

<400> SEQUENCE: 30

```
Tyr Trp Ser Tyr Pro Ser Trp Ser Pro Tyr Arg Gly Met Asp Tyr
1               5                   10                  15
```

<210> SEQ ID NO 31
<211> LENGTH: 330
<212> TYPE: PRT
<213> ORGANISM: Homo sapiens

<400> SEQUENCE: 31

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 32
<211> LENGTH: 330
<212> TYPE: PRT
<213> ORGANISM: Homo sapiens

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

-continued

```
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 33
<211> LENGTH: 327
<212> TYPE: PRT
<213> ORGANISM: Homo sapiens

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110
```

```
Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 34
<211> LENGTH: 327
<212> TYPE: PRT
<213> ORGANISM: Homo sapiens

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325


<210> SEQ ID NO 35
<211> LENGTH: 327
<212> TYPE: PRT
<213> ORGANISM: Homo sapiens

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325


<210> SEQ ID NO 36
<211> LENGTH: 327
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 37
<211> LENGTH: 106
<212> TYPE: PRT
<213> ORGANISM: Homo sapiens

<400> SEQUENCE: 37

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 38
<211> LENGTH: 454
<212> TYPE: PRT
<213> ORGANISM: Homo sapiens

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Ser Tyr Pro Ser Trp Trp Pro Tyr Arg Gly Met Asp
            100                 105                 110

Tyr Trp Gly Gln Gly Thr Leu Val Thr Val Ser Ser Ala Ser Thr Lys
        115                 120                 125
```

```
Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 39
<211> LENGTH: 454
<212> TYPE: PRT
<213> ORGANISM: Homo sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45
```

```
Ala Tyr Ile Ser Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Ser Tyr Pro Ser Trp Trp Pro Tyr Arg Gly Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Gly
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 40
<211> LENGTH: 451
<212> TYPE: PRT
<213> ORGANISM: Homo sapiens

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Ser Tyr Pro Ser Trp Trp Pro Tyr Arg Gly Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 41
<211> LENGTH: 451
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Ser Tyr Pro Ser Trp Trp Pro Tyr Arg Gly Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
```

```
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 42
<211> LENGTH: 451
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Ser Tyr Pro Ser Trp Trp Pro Tyr Arg Gly Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205
```

```
Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 43
<211> LENGTH: 453
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Ser Ser Ser Ser Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ser Thr Tyr Ser Ser Lys Trp Val Trp Gly Met Asp Tyr
            100                 105                 110

Trp Gly Gln Gly Thr Leu Val Thr Val Ser Ser Ala Ser Thr Lys Gly
        115                 120                 125
```

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 44
<211> LENGTH: 450
<212> TYPE: PRT
<213> ORGANISM: Homo sapiens

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val

```
        35                  40                  45

Ala Tyr Ile Tyr Pro Tyr Ser Ser Ser Ser Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ser Thr Tyr Ser Ser Lys Trp Val Trp Gly Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 45
<211> LENGTH: 450
<212> TYPE: PRT
<213> ORGANISM: Homo sapiens

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Ser Ser Ser Ser Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ser Thr Tyr Ser Ser Lys Trp Val Trp Gly Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
```

```
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 46
<211> LENGTH: 450
<212> TYPE: PRT
<213> ORGANISM: Homo sapiens

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Ser Ser Ser Ser Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ser Thr Tyr Ser Ser Lys Trp Val Trp Gly Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285
```

```
Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 47
<211> LENGTH: 214
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Asp Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 48
<211> LENGTH: 20
<212> TYPE: PRT
<213> ORGANISM: Homo sapiens

<400> SEQUENCE: 48

Met Tyr Arg Met Gln Leu Leu Ser Cys Ile Ala Leu Ser Leu Ala Leu
1               5                   10                  15

Val Thr Asn Ser
            20


<210> SEQ ID NO 49
<211> LENGTH: 32
<212> TYPE: PRT
<213> ORGANISM: Homo sapiens

<400> SEQUENCE: 49

Pro Ser Lys Ser Ile Leu Leu Ser Gly Thr Val Ser Phe Ser Val Trp
1               5                   10                  15

Ile Leu Cys Glu Ala His Cys Leu Lys Val Ala Val Asp Gly Gln His
            20                  25                  30


<210> SEQ ID NO 50
<211> LENGTH: 32
<212> TYPE: PRT
<213> ORGANISM: Macaque

<400> SEQUENCE: 50

Pro Ser Lys Ser Ile Thr Leu Ser Gly Thr Val Ser Phe Ser Val Trp
1               5                   10                  15

Ile Leu Cys Asp Ala His Cys Leu Lys Val Ala Val Asp Gly Gln His
            20                  25                  30


<210> SEQ ID NO 51
<211> LENGTH: 32
<212> TYPE: PRT
<213> ORGANISM: Rat

<400> SEQUENCE: 51

Pro Ser Lys Ser Ile Asn Ile Ser Gly Val Val Ser Phe Ser Val Trp
1               5                   10                  15

Ile Leu Cys Glu Gly His Cys Phe Lys Val Ala Val Asp Gly Gln His
            20                  25                  30


<210> SEQ ID NO 52
<211> LENGTH: 32
<212> TYPE: PRT
<213> ORGANISM: Mus musculus

<400> SEQUENCE: 52

Pro Ser Lys Ser Ile Met Ile Ser Gly Asn Val Ser Phe Ser Val Trp
1               5                   10                  15

Ile Ile Cys Glu Gly His Cys Phe Lys Val Ala Val Asn Gly Gln His
            20                  25                  30


<210> SEQ ID NO 53
<211> LENGTH: 32
<212> TYPE: PRT
<213> ORGANISM: Homo sapiens
```

<400> SEQUENCE: 53

```
Pro Ser Lys Ser Ile Leu Leu Ser Gly Thr Val Ser Phe Ser Val Trp
1               5                   10                  15

Ile Leu Cys Glu Ala His Cys Leu Lys Val Ala Val Asp Gly Gln His
            20                  25                  30
```

<210> SEQ ID NO 54
<211> LENGTH: 32
<212> TYPE: PRT
<213> ORGANISM: Homo sapiens

<400> SEQUENCE: 54

```
Pro Gly Glu Cys Leu Arg Val Arg Gly Glu Val Val Ala Glu Val Cys
1               5                   10                  15

Ile Thr Phe Asp Gln Ala Asn Leu Thr Val Lys Leu Pro Asp Gly Tyr
            20                  25                  30
```

<210> SEQ ID NO 55
<211> LENGTH: 32
<212> TYPE: PRT
<213> ORGANISM: Homo sapiens

<400> SEQUENCE: 55

```
Pro Gly Ser Thr Leu Lys Ile Thr Gly Ser Ile Glu Val Lys Phe Thr
1               5                   10                  15

Val Thr Phe Glu Ser Asp Lys Phe Lys Val Lys Leu Pro Asp Gly His
            20                  25                  30
```

<210> SEQ ID NO 56
<211> LENGTH: 32
<212> TYPE: PRT
<213> ORGANISM: Homo sapiens

<400> SEQUENCE: 56

```
Pro Arg Met Leu Ile Thr Ile Leu Gly Thr Val Pro Phe Lys Ile Gln
1               5                   10                  15

Val Leu Val Glu Pro Asp His Phe Lys Val Ala Val Asn Asp Ala His
            20                  25                  30
```

<210> SEQ ID NO 57
<211> LENGTH: 32
<212> TYPE: PRT
<213> ORGANISM: Homo sapiens

<400> SEQUENCE: 57

```
Ala Arg Arg Thr Ile Ile Ile Lys Gly Tyr Val Phe Phe Asp Leu Ser
1               5                   10                  15

Ile Arg Cys Gly Leu Asp Arg Phe Lys Val Tyr Ala Asn Gly Gln His
            20                  25                  30
```

<210> SEQ ID NO 58
<211> LENGTH: 32
<212> TYPE: PRT
<213> ORGANISM: Homo sapiens

<400> SEQUENCE: 58

```
Pro Gly Thr Val Leu Arg Ile Arg Gly Leu Val Pro Phe Glu Val Leu
1               5                   10                  15

Ile Ile Ala Ser Asp Asp Gly Phe Lys Ala Val Val Gly Asp Ala Gln
            20                  25                  30
```

<210> SEQ ID NO 59
<211> LENGTH: 32
<212> TYPE: PRT
<213> ORGANISM: Homo sapiens

<400> SEQUENCE: 59

Pro Gly Arg Thr Val Val Val Lys Gly Glu Val Tyr Phe Glu Met Ile
1               5                   10                  15

Ile Tyr Cys Asp Val Arg Glu Phe Lys Val Ala Val Asn Gly Val His
            20                  25                  30

<210> SEQ ID NO 60
<211> LENGTH: 32
<212> TYPE: PRT
<213> ORGANISM: Homo sapiens

<400> SEQUENCE: 60

Thr Gly Ser Thr Val Thr Ile Lys Gly Arg Pro Glu Phe Glu Leu Ser
1               5                   10                  15

Ile Ser Val Leu Pro Asp Lys Tyr Gln Val Met Val Asn Gly Gln Ser
            20                  25                  30

<210> SEQ ID NO 61
<211> LENGTH: 453
<212> TYPE: PRT
<213> ORGANISM: Homo sapiens

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Ser Ser Ser Ser Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ser Thr Tyr Ser Ser Lys Trp Val Trp Gly Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu

```
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 62
<211> LENGTH: 216
<212> TYPE: PRT
<213> ORGANISM: Homo sapiens

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Asp Ser Asn
                85                  90                  95

Pro Ile Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140
```

-continued

```
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

ANTI-GALECTIN-9 ANTIBODIES AND USES THEREOF

SEQUENCE LISTING

The instant application contains a Sequence Listing which has been submitted in ASCII format and is hereby incorporated by reference in its entirety. Said ASCII copy was created on Jul. 1, 2022, is named Corrected_Seq_Listing.TXT, and is 131,072 bytes in size.

BACKGROUND OF INVENTION

Immune checkpoint blockade has demonstrated unprecedented success in the past few years as cancer treatment. Often antibodies are used to block immune inhibitory pathways, such as the cytotoxic T-lymphocyte-associated protein 4 (CTLA-4) and programmed death 1 (PD-1) pathways. While therapies targeting those two pathways have shown success in treating several cancer types, anti-CTLA-4 and anti-PD-1 therapies have a response rate of 10 to 60% of treated patients, depending on cancer type, and have not yet shown the ability to exceed a response rate of 60%, even when used in combination (Kyvistborg et al., *Science*. 2018 Feb. 2; 359(6375):516-517). Additionally, a large number of cancer types are refractory to these therapies. As part of efforts to improve existing immunotherapies in the clinic, the field has started to focus on the role of abnormalities in interferon signaling and upregulation of alternative checkpoints as potential causes for the limitation of current therapies. One such potential alternate checkpoint is T-cell immunoglobulin mucin-3 (Tim-3)/Galectin-9 (e.g., reviewed in Yang and Hung; *Cancer biology and cancer treatment*; October 2017, Vol. 60 No. 10: 1058-1064, and references therein).

Galectin-9 is a tandem-repeat lectin consisting of two carbohydrate recognition domains (CRDs) and was discovered and described for the first time in 1997 in patients suffering from Hodgkin's lymphoma (HL) (Tureci et al., *J. Biol. Chem.* 1997, 272, 6416-6422). Three isoforms exist, and can be located within the cell or extracellularly. Elevated Galectin-9 levels have been in observed a wide range of cancers, including melanoma, Hodgkin's lymphoma, hepatocellular, pancreatic, gastric, colon and clear cell renal cell cancers (Wdowiak et al. *Int. J. Mol. Sci.* 2018, 19, 210). In renal cancer, patients with high Galectin-9 expression showed more advanced progression of the disease with larger tumor size and necrosis (Kawashima et al.; *BJU Int.* 2014; 113:320-332). In melanoma—a cancer considered as one of the most lethal cancers due to its aggressive metastasis and resistance to therapy—Galectin-9 was expressed in 57% of tumors and was significantly increased in the plasma of patients with advanced melanoma compared to healthy controls (Enninga et al., *Melanoma Res.* 2016 October; 26(5): 429-441). A number of studies have shown utility for Gal-9 as a prognostic marker, and more recently as a potential new drug target (Enninga et al., 2016; Kawashima et al. *BJU Int* 2014; 113: 320-332; Kageshita et al., Int J Cancer. 2002 Jun. 20; 99(6):809-16, and references therein). Galectin-9 has been described to play an important role in in a number of cellular processes such as adhesion, cancer cell aggregation, apoptosis, and chemotaxis. Recent studies have shown a role for Galectin-9 in immune modulation in support of the tumor, e.g., through negative regulation of Th1 type responses, Th2 polarization and polarization of macrophages to the M2 phenotype. This work also includes studies that have shown that Galectin-9 participates in direct inactivation of T cells through interactions with the T-cell immunoglobulin and mucin protein 3 (TIM-3) receptor (Dardalhon et al., *J Immunol.,* 2010, 185, 1383-1392; Sanchez-Fueyo et al., *Nat Immunol.,* 2003, 4, 1093-1101). Galectin-9 has also been found to play a role in polarizing T cell differentiation into tumor suppressive phenotypes), as well as promoting tolerogenic macrophage programming and adaptive immune suppression (Daley et al., *Nat Med.,* 2017, 23, 556-567). In mouse models of pancreatic ductal adenocarcinoma (PDA), blockade of the checkpoint interaction between Galectin-9 and the receptor Dectin-1 found on innate immune cells in the tumor microenvironment (TME) has been shown to increase anti-tumor immune responses in the TME and to slow tumor progression (Daley et al., *Nat Med.,* 2017, 23, 556-567). Galectin-9 also has been found to bind to CD206, a surface marker of M2 type macrophages, resulting in a reduced secretion of CVL22 (MDC), a macrophage derived chemokine which has been associated with longer survival and lower recurrence risk in lung cancer (Enninga et al, *J Pathol.* 2018 August; 245(4): 468-477).

Accordingly, modulating the activity of Galectin-9 and/or one or more of its receptors may provide a novel cancer therapy approach, alone or in combination with existing therapies. Described herein are novel human antibodies which bind to human Galectin-9 and their therapeutic use in the treatment of cancer.

SUMMARY OF INVENTION

The present disclosure is based, at least in part, on the development of anti-Galectin-9 antibodies that potently suppress signaling triggered by Galectin-9. Such antibodies are capable of suppressing Galectin-9 signaling and/or eliminating Galectin-9 positive pathologic cells, thereby benefiting treatment of diseases associated with Galectin-9.

Accordingly, one aspect of the present disclosure provides a method for modulating an immune response in a subject. In some embodiments, the method comprises treating a subject with an anti-Galectin-9 antibody and a checkpoint inhibitor. In some embodiments, the anti-Galectin-9 antibody is administered to a subject that is being treated with a checkpoint inhibitor. In some embodiments, a checkpoint inhibitor is administered to a subject being treated with an anti-galectin-9 antibody. In some embodiments, the method comprises administering to a subject in need thereof an anti-Galectin-9 antibody and a checkpoint inhibitor. In some embodiments, the anti-Galectin-9 antibody and the checkpoint inhibitor are administered concurrently. In some embodiments, the anti-Galectin-9 antibody is administered subsequently to the checkpoint inhibitor. In some embodiments, the checkpoint inhibitor is administered subsequently to the anti-Galectin-9 antibody.

In some embodiments, the method comprises administering to a subject in need thereof an effective amount of an anti-Galectin-9 antibody (anti-Gal-9 antibody) that binds a Galectin-9 polypeptide, wherein the subject is on a treatment or planning to be on a treatment comprising a checkpoint inhibitor. In some embodiments, the method comprises: (i) administering to a subject in need thereof an effective amount of an anti-Galectin-9 antibody (anti-Gal-9 antibody) that binds a Galectin-9 polypeptide; and (ii) administering to the subject an effective amount of a checkpoint inhibitor. In some embodiments, the checkpoint inhibitor in step (ii) is administered at the same time or around the same time as the anti-galectin-9 antibody in step (i). In some embodiments, the checkpoint inhibitor in step (ii) is administered at a future date (e.g., subsequently) to the anti-galectin-9 antibody in step (i). In some embodiments the method comprises administering to a subject in need thereof an effective amount of an anti-Galectin-9 antibody (anti-Gal-9 antibody) that binds a Galectin-9 polypeptide, wherein the subject is on an existing treatment comprising a checkpoint inhibitor. In some embodiments, the method comprises administering to a subject in need thereof an effective amount of a checkpoint inhibitor, wherein the subject is on a treatment or planning to be on a treatment comprising an anti-Galectin-9 antibody (anti-Gal-9 antibody) that binds a Galectin-9 polypeptide. In some embodiments, the method comprises: (i) administering to a subject in need thereof an effective amount of a checkpoint inhibitor; and (ii) administering to a subject in need thereof an effective amount of an anti-Galectin-9 antibody (anti-Gal-9 antibody) that binds a Galectin-9 polypeptide. In some embodiments, the anti-Galectin-9 antibody in step (ii) is administered at the same time or around the same time as the checkpoint inhibitor in step (i). In some embodiments, the anti-Galectin-9 antibody in step (ii) is administered at a future date (e.g., subsequently) to the checkpoint inhibitor in step (i). In some embodiments the method comprises administering to a subject in need thereof an effective amount checkpoint inhibitor, wherein the subject is on an existing treatment comprising an anti-Galectin-9 antibody that binds a Galectin-9 polypeptide.

Accordingly, one aspect of the present disclosure provides a method for modulating (e.g., increasing) an immune response in a subject. In some embodiments, the method comprises administering to a subject in need thereof an effective amount of an anti-Galectin-9 antibody (anti-Gal9 antibody) that binds a Galectin-9 polypeptide, wherein the subject is on a treatment comprising a checkpoint inhibitor. In some embodiments, the method comprises administering to a subject in need thereof an effective amount of a checkpoint inhibitor, wherein the subject is on a treatment comprising an anti-Galectin-9 antibody (anti-Gal9 antibody) that binds a Galectin-9 polypeptide. In some embodiments, the method comprises: (i) administering to a subject in need thereof an effective amount of an anti-Galectin-9 antibody (anti-Gal9 antibody) that binds a Galectin-9 polypeptide; and (ii) administering to the subject an effective amount of a checkpoint inhibitor. In some embodiments, the anti-Galectin-9 antibody and the checkpoint inhibitor are administered concurrently. In some embodiments, the anti-Galectin-9 antibody is administered subsequently to the checkpoint inhibitor. In some embodiments, the checkpoint inhibitor is administered subsequently to the anti-Galectin-9 antibody.

In some embodiments, the modulation of the immune response comprises increased levels of one or more of: interferon γ expression in one or more T cell populations, TNF-alpha expression in one or more T cell populations, CD44 expression in CD4+ cells, CD44 expression in CD8+ cells, or an increased number of CD4+ T cells or CD8+ T cells, or combinations thereof, as compared to a level found in a control subject or or a level found prior to administration of the galectin-9 antibody, alone or in combination with a checkpoint inhibitor or a level found prior to administration of the checkpoint inhibitor, alone or in combination with the galectin-9 antibody.

In any of the methods disclosed herein, the anti-Gal9 antibody may specifically bind a carbohydrate recognition 2 (CRD2) domain of the Galectin-9 polypeptide as relative to a carbohydrate recognition 1 (CRD1) domain of the Galectin-9 polypeptide. For example, the anti-Gal9 antibody may not bind to the CRD1 domain. In some examples, the Galectin-9 polypeptide is a human Galectin-9 polypeptide.

In some examples, the anti-Gal9 antibody may bind an epitope of the Galectin-9 polypeptide, and wherein the epitope comprises one or more of residues corresponding to S208, L210, A288, L279, and W277 of SEQ ID NO: 2. Alternatively or in addition, the anti-Gal9 antibody may bind an epitope of the Galectin-9 polypeptide, and the epitope does not comprise one or more of residues corresponding to Y204, R221, R239, Y298, R302, and R309 of SEQ ID NO: 2.

In some examples, the anti-Gal9 antibody comprises the same heavy chain complementary determining regions (CDRs) as antibody G9.2-17, and/or the same light chain complementary determining regions (CDRs) as antibody G9.2-17. In some examples, the anti-Gal9 antibody comprises a heavy chain framework of $V_H$ 3-48; and/or a light chain framework of Vκ 1-39. In specific examples, the anti-Gal9 antibody comprises the same heavy chain variable region ($V_H$) and/or the same light chain variable region ($V_L$) as antibody G9.2-17.

Any of the anti-Gal9 antibodies disclosed herein may be a human antibody or a humanized antibody. In some examples, the anti-Gal9 antibody is a full-length antibody. In some examples, the anti-Gal9 antibody is an antigen binding fragment, for example, Fab. For example, the anti-Gal9 antibody can be a human IgG1 or human IgG4 molecule. In specific examples, the anti-Gal9 antibody is a human IgG4 molecule comprises a heavy chain constant region, which comprises the amino acid sequence of SEQ ID NO: 35 or SEQ ID NO: 36. In one specific example, the anti-Gal9 antibody comprises a heavy chain that comprises the amino acid sequence of SEQ ID NO: 41 or SEQ ID NO: 42; and a light chain that comprises the amino acid sequence of SEQ ID NO: 47.

In any of the methods disclosed herein, the checkpoint inhibitor is an antibody that binds PD-1 or PD-L1. Examples include cemiplimab, nivolumab, pembrolizumab, avelumab, durvalumab, or atezolizumab.

In any of the methods disclosed herein, the subject is a human subject having or suspected of having an autoimmune disease, a solid cancer, a microbial disease, a hematological malignancy, or an allergic disorder. In some examples, the subject is a human patient having an autoimmune disease selected from the group consisting of a rheumatoid condition, an autoimmune respiratory disease, an autoimmune metabolic and/or endocrine disorder, and a fibrotic condition. In some examples, the subject is a human patient having a solid tumor selected from the group consisting of pancreatic ductal adenocarcinoma (PDA), colorectal cancer (CRC), melanoma, cholangiocarcinoma, breast cancer, lung cancer, upper and lower gastrointestinal malignancies, squamous cell head and neck cancer, genitourinary cancer, ovarian cancer, and sarcomas. In other examples, the subject is a human patient having a hematological malignancy selected from the group consisting of acute lymphoblastic leukemia, chronic lymphocytic leukemia, lymphomas, multiple myeloma, acute myelogenous leukemia, acute myeloid leukemia (AML), chronic myelogenous leukemia, myelodysplastic syndromes, and myeloproliferative neoplasms.

In another aspect, provided herein is an isolated antibody that binds a Galectin 9 polypeptide (e.g., a human galectin 9 polypeptide), wherein the antibody is a human IgG4 molecule comprising a heavy chain constant region that comprises the amino acid sequence of SEQ ID NO: 36. In some embodiments, the anti-Gal9 antibody specifically binds a carbohydrate recognition 2 (CRD2) domain of the Galectin-9 polypeptide as relative to a carbohydrate recognition 1 (CRD1) domain of the Galectin-9 polypeptide. For example, the anti-Gal9 antibody may not bind to the CRD1 domain.

In some embodiments, the anti-Gal9 antibody binds an epitope of the Galectin-9 polypeptide, and the epitope comprises one or more of residues corresponding to S208, L210, A288, L279, and W277 of SEQ ID NO: 2. Alternatively or in addition, the anti-Gal9 antibody binds an epitope of the Galectin-9 polypeptide, and the epitope does not comprise one or more of residues corresponding to Y204, R221, R239, Y298, R302, and R309 of SEQ ID NO: 2.

In some embodiments, the anti-Gal9 antibody comprises the same heavy chain complementary determining regions (CDRs) as antibody G9.2-17, and/or the same light chain complementary determining regions (CDRs) as antibody G9.2-17. The anti-Gal9 antibody comprises a heavy chain framework of $V_H$ 3-48; and/or a light chain framework of Vκ 1-39. In some examples, the anti-Gal9 antibody comprises the same heavy chain variable region ($V_H$) and/or the same light chain variable region ($V_L$) as antibody G9.2-17. In specific examples, the anti-Gal9 antibody comprises a heavy chain that comprises the amino acid sequence of SEQ ID NO: 42 and a light chain that comprises the amino acid sequence of SEQ ID NO: 47.

Also within the scope of the present disclosure are pharmaceutical compositions comprising any of the anti-galectin 9 antibodies described herein and optionally a checkpoint inhibitor such as a PD1 or PD-L1 inhibitor for modulating (e.g., increasing) immune responses and/or treating any of the target diseases disclosed herein, as well as uses of the anti-galectin 9 antibody, either alone or in combination with the checkpoint inhibitor, for manufacturing a medicament for use in the intended therapeutic uses.

Also within the scope of the present disclosure are pharmaceutical compositions comprising any of the anti-galectin 9 antibodies described herein and optionally a checkpoint inhibitor such as a PD1 or PD-L1 inhibitor for modulating immune responses and/or treating any of the target diseases disclosed herein, as well as uses of the anti-galectin 9 antibody, either alone or in combination with the checkpoint inhibitor, for manufacturing a medicament for use in the intended therapeutic uses.

Also within the scope of the present disclosure are methods comprising administering any of the anti-galectin 9 antibodies or anti-galectin 9 antibody compositions described herein and optionally a checkpoint inhibitor such as a PD1 or PD-L1 inhibitor for modulating immune responses and/or treating any of the target diseases disclosed herein, as well as uses of the anti-galectin 9 antibody, either alone or in combination with the checkpoint inhibitor, for manufacturing a medicament for use in the intended therapeutic uses.

Also within the scope of the present disclosure are methods comprising administering any of the anti-galectin 9 antibodies or anti-galectin 9 antibody compositions described herein and optionally a checkpoint inhibitor such as a PD1 or PD-L1 inhibitor for modulating (e.g., increasing) immune responses and/or treating any of the target diseases disclosed herein, as well as uses of the anti-galectin 9 antibody, either alone or in combination with the checkpoint inhibitor, for manufacturing a medicament for use in the intended therapeutic uses.

The details of one or more embodiments of the invention are set forth in the description below. Other features or advantages of the present invention will be apparent from the following drawing and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to the drawing in combination with the detailed description of specific embodiments presented herein.

FIG. 2A: A diagram showing the binding activity of G9.2-17 to Galectin-9 CRD2 mutants as determined by phage ELISA. The reduction in ELISA signal indicates a site on the Galectin-9 CRD2 that is critical to G9.2-17 binding. FIG. 2B: a diagram depicting the location of W309 as mapped on the crystal structure of human Galectin-9 CRD2 (PDB ID 3NV2), which is opposite to the binding site of the sugar ligand as mapped on the crystal structure (W309 corresponds with W277 in UniProt ID 000182-2; PDB ID 3NV2).

Figure 9A:
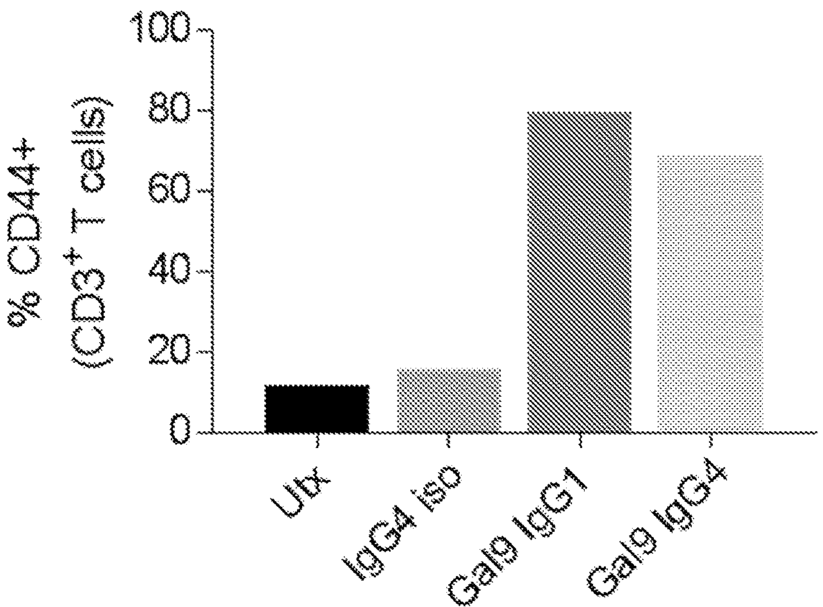
Figure 9B:
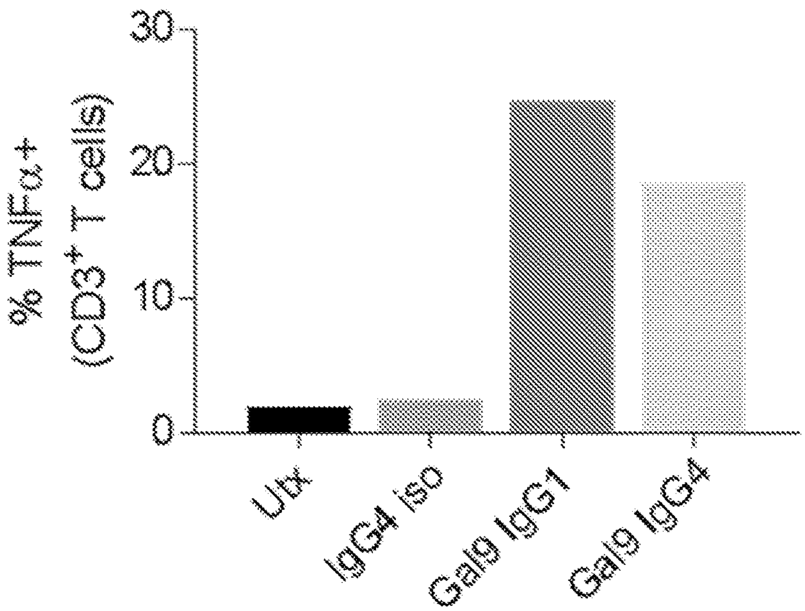
Figure 9C:
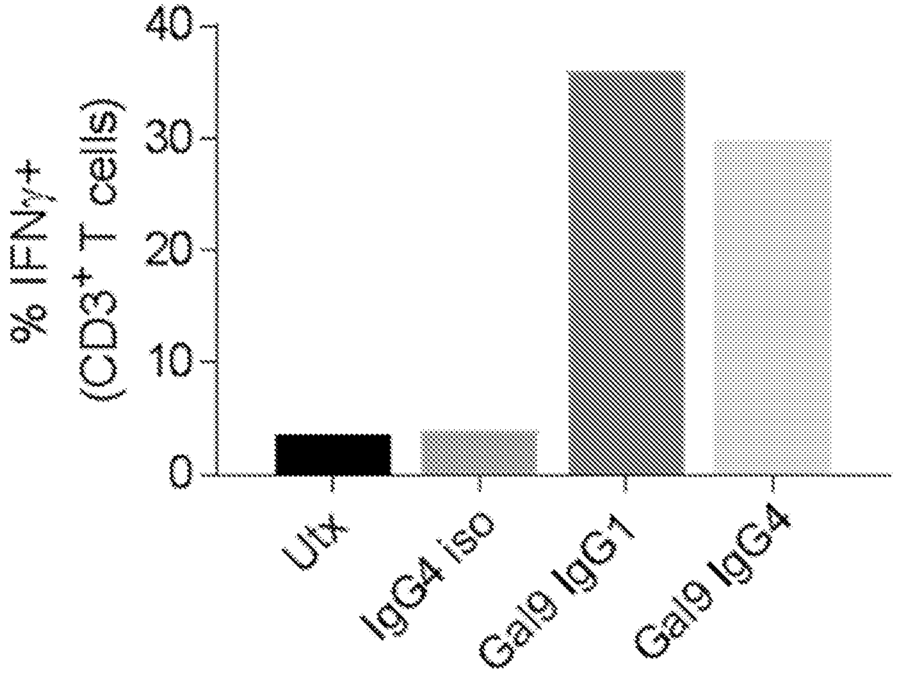

FIGS. 9A-9C depict bar graphs showing CD44 (FIG. 9A), TNF-alpha (FIG. 9B) and IFN-gamma (FIG. 9C) expression in CD3+ T cells in a sample of liver metastasis from a colorectal cancer patient (PDOTs) treated with G9.2-17 IgG1 (100 nM) or G9.2-17 IgG4 (100 nM) as compared to IgG1 (100 nM) or untreated control (Utx).

Figure 10:
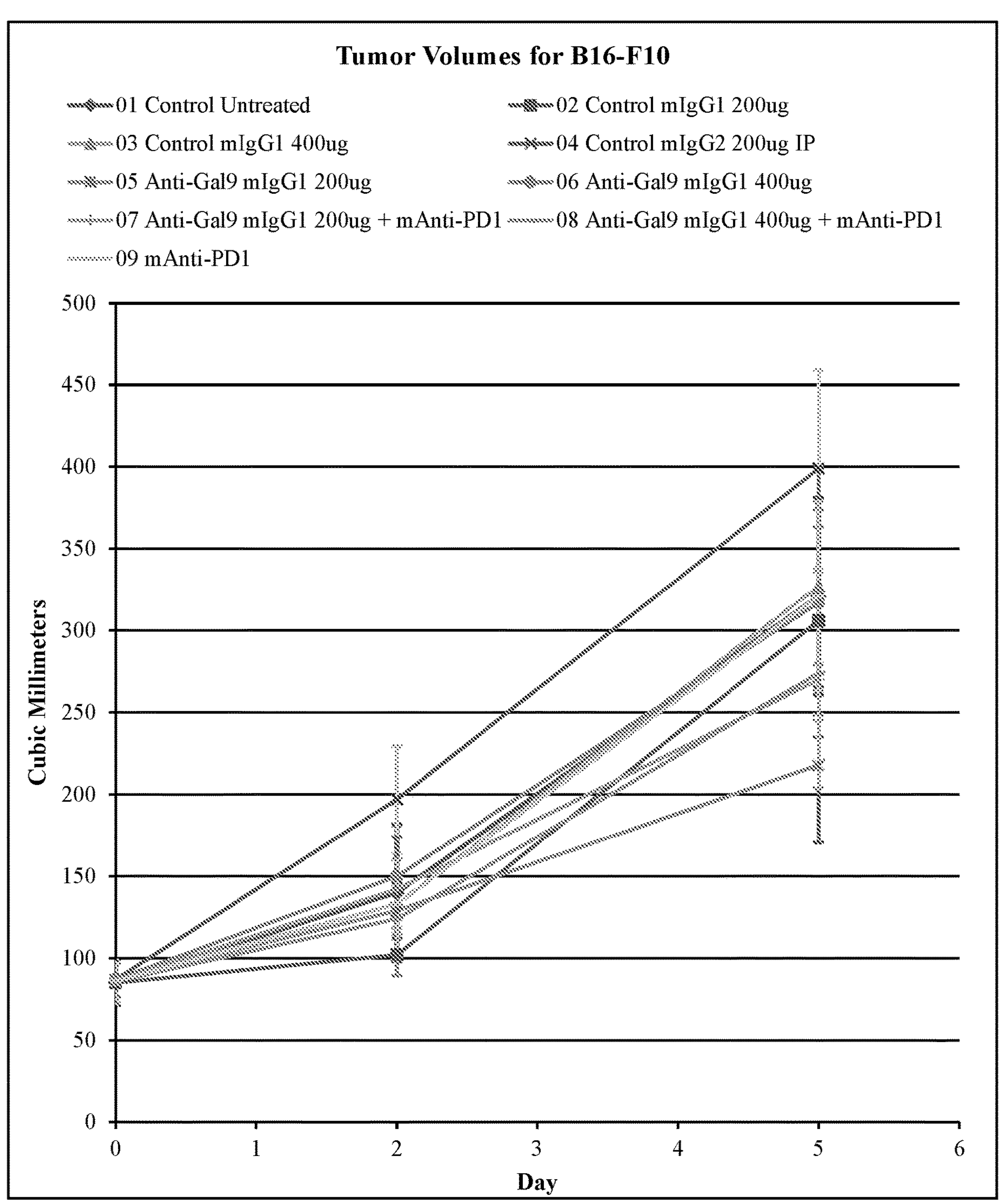

FIG. 10 depicts a line graph showing the effect of 9.2-17 in a B16F10 subcutaneous syngeneic model. Tumors were engrafted subcutaneously and treated with G9.2-17 IgG1 mouse mAb. Animals were dosed on day 0 and day 4 intravenously (i.v.) unless otherwise specified in the legend.

Figure 11:
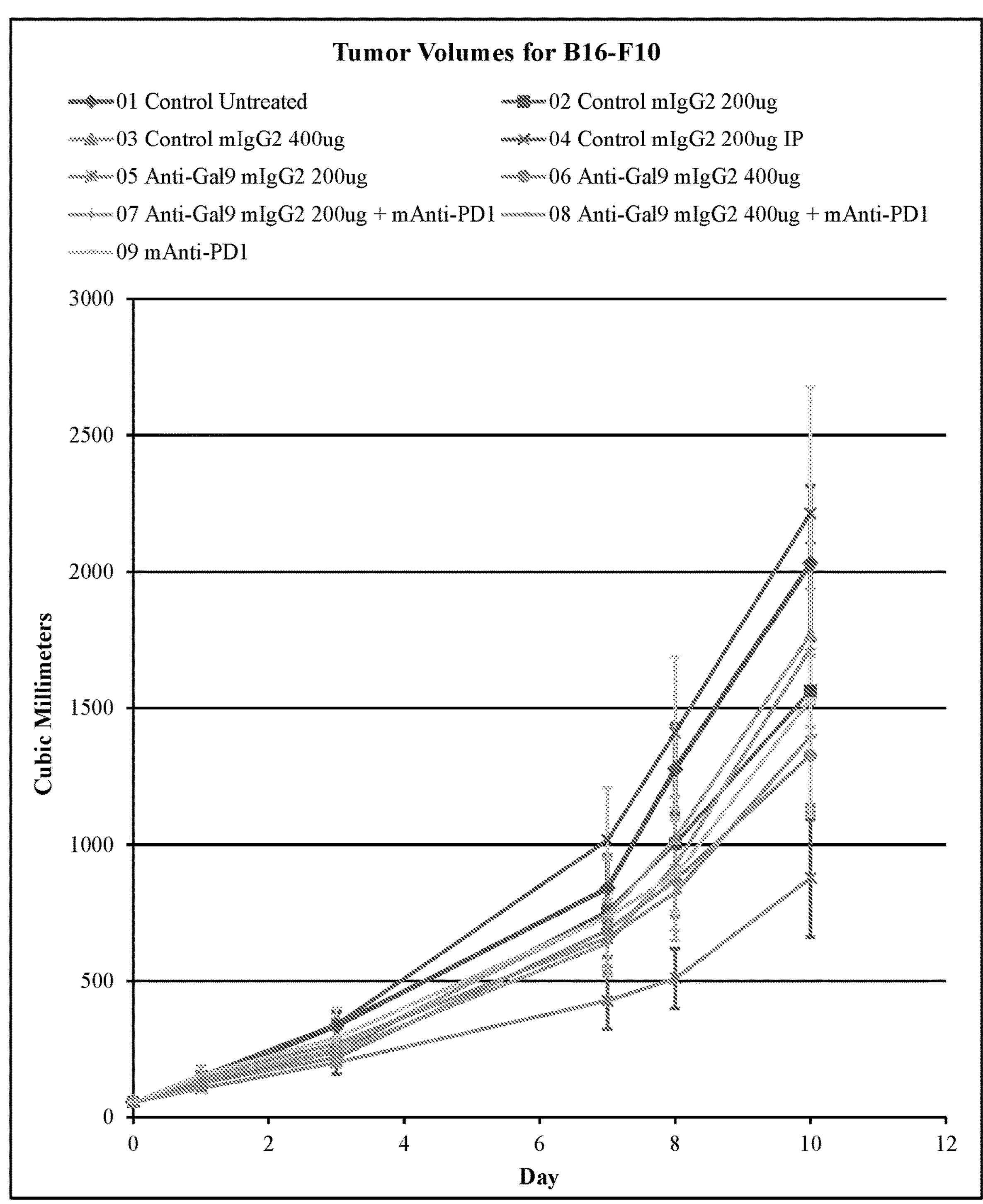

FIG. 11 depicts a line graph showing the effect of 9.2-17 in a B16F10 subcutaneous syngeneic model. Tumors were engrafted subcutaneously and treated with G9.2-17 IgG2a mouse mAb. Animals were dosed on day 0 and once every 4 days thereafter until the end of the experiment. mAbs were administered i.v. unless otherwise specified in the legend.

Figure 12:
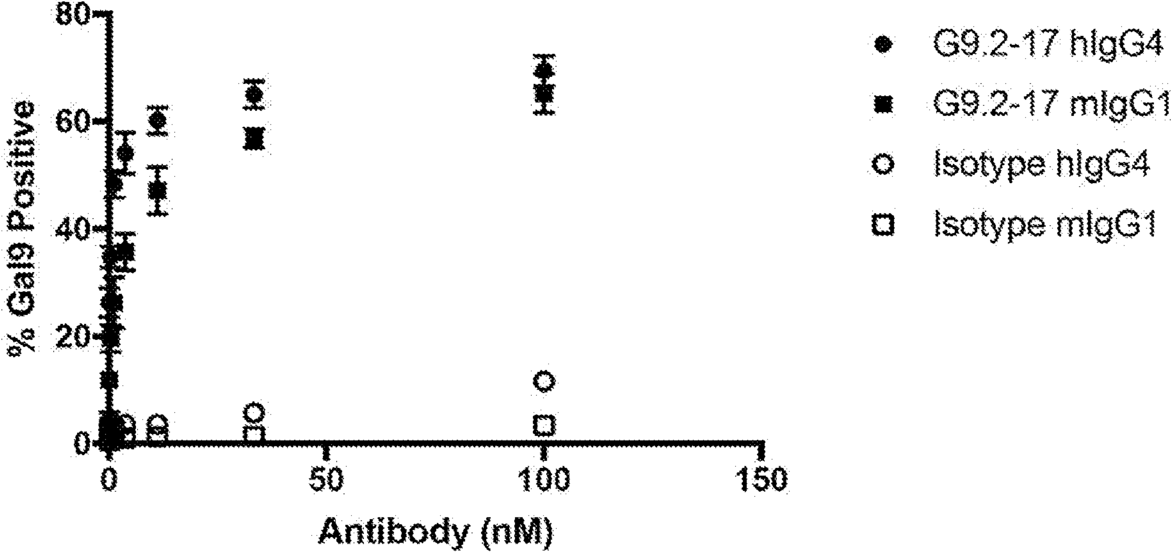

FIG. 12 depicts a graph showing a cell based binding assay CRL-2134 cell lines were incubated with a biotinylated Fab, and bound Fab was detected using neutravidin conjugated with DyLight 650. Samples were then analyzed using flow cytometry. Strong signals were observed for the Galectin-9 antibody 9.2-17, but not for the isotype controls. The $K_D$ (nM) values for the Gal-9 antibodies in the two formats were as follows: G9.2-17 hIgG1: 0.41±0.07; G9.2-17 mIgG1: 2.91±0.66.

Figure 13A:
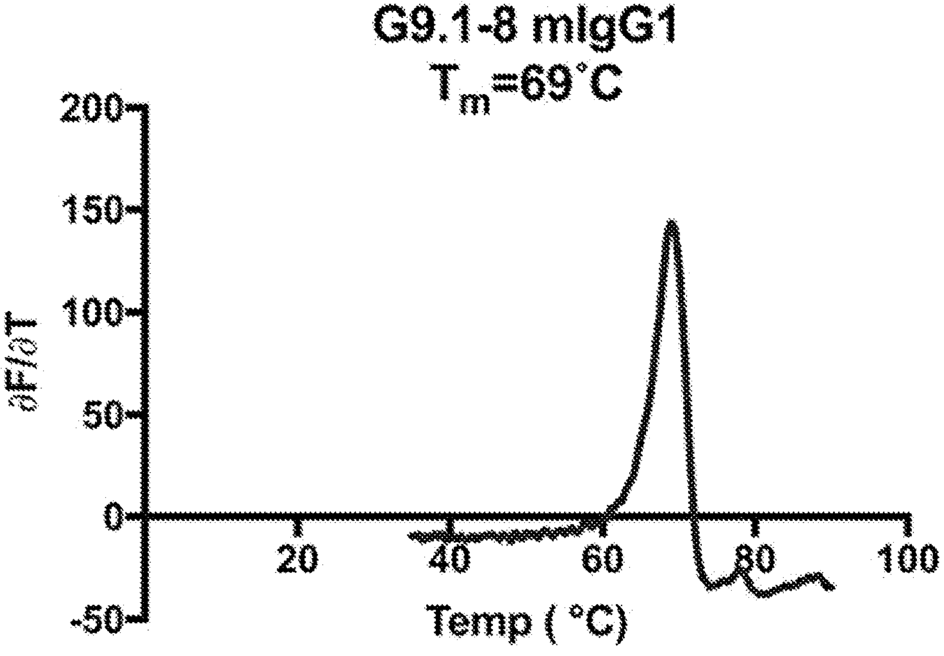
Figure 13B:
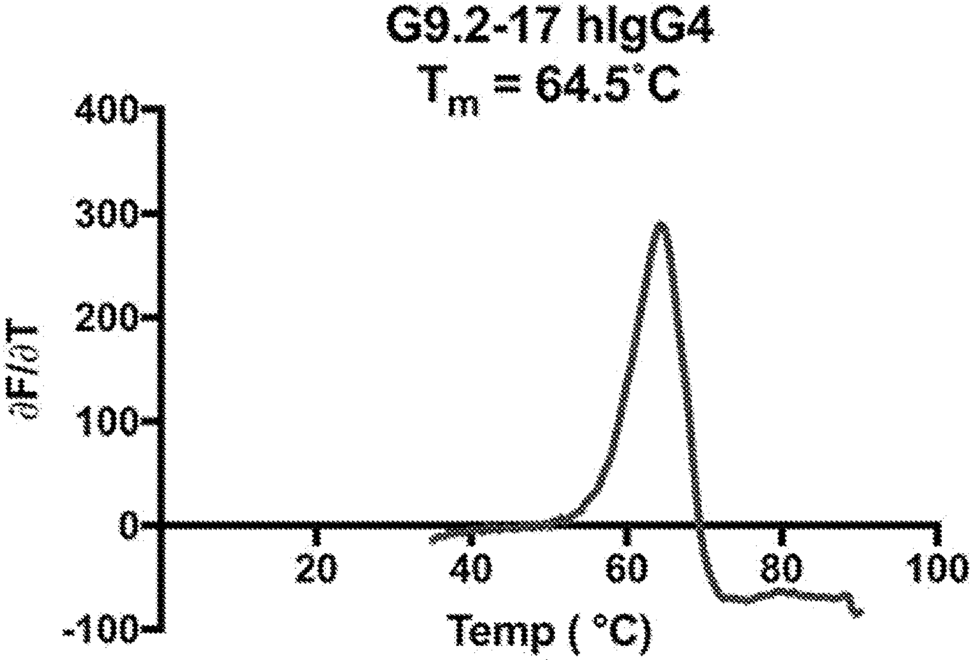

FIGS. 13A and 13B depict graphs showing a thermal stability determination of anti-Galectin-9 antibodies. The first derivative of the fluorescence emission plotted as a function of temperature (−dF/dT). The melting temperature is represented as the temperature at which a peak is observed for G9.1-8 mIgG1 (FIG. 13A) and G9.2-17 hIgG4 (FIG. 13B). Thermal transition was determined using change in binding of fluorophor SYPRO Orange (ThermoFisher) using a real-time PCR instrument with a heating rate of 1° C. per minute, essentially following a method as described in Vedadi et al., Chemical screening methods to identify ligands that promote protein stability, protein crystallization, and structure determination; Proc Natl Acad Sci USA. 2006 Oct. 24; 103(43):15835-40.

Figure 14:
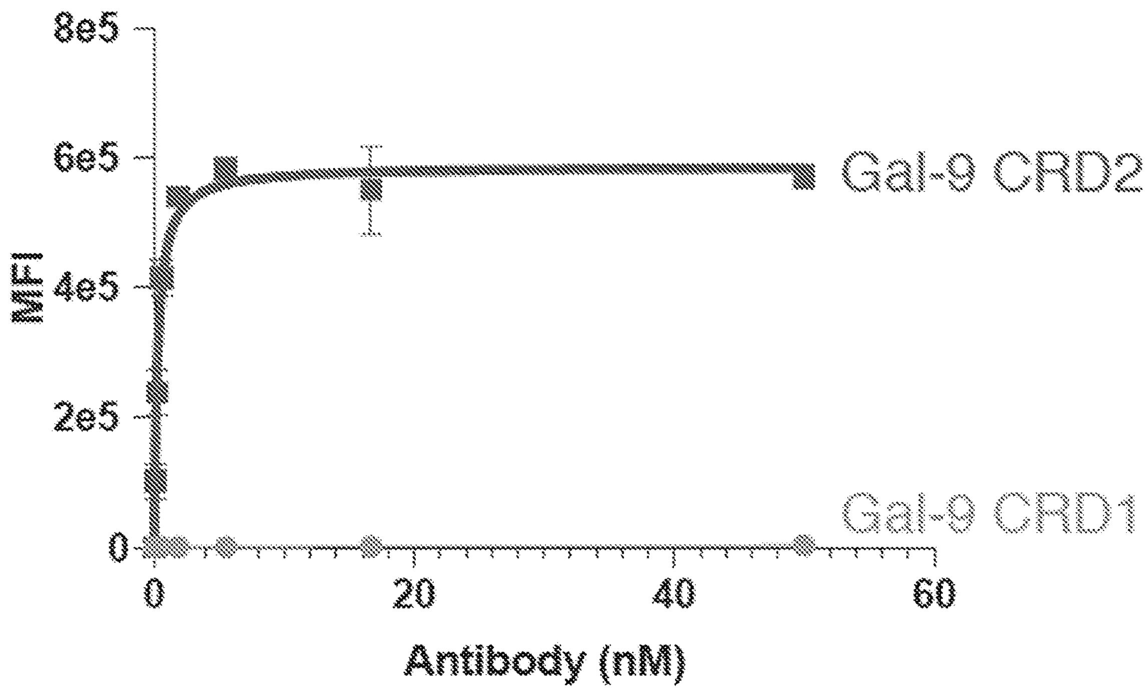

FIG. 14 depicts a graph showing that the G9.2-17 antibody is specific for the CRD2 domain of Galectin-9 relative to CRD1.

Figure 15:
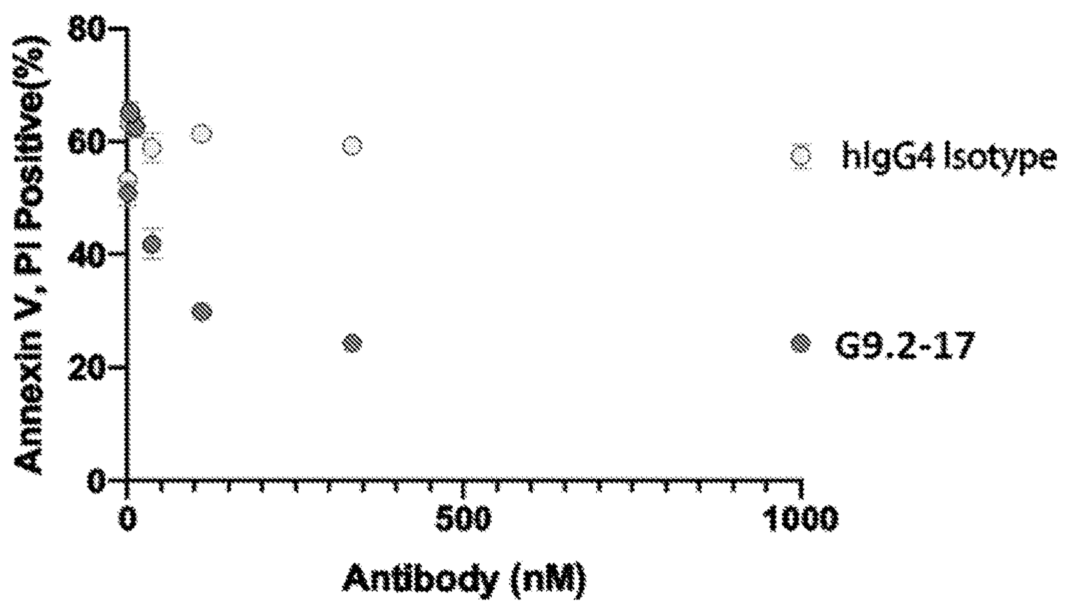
Figure 16A:
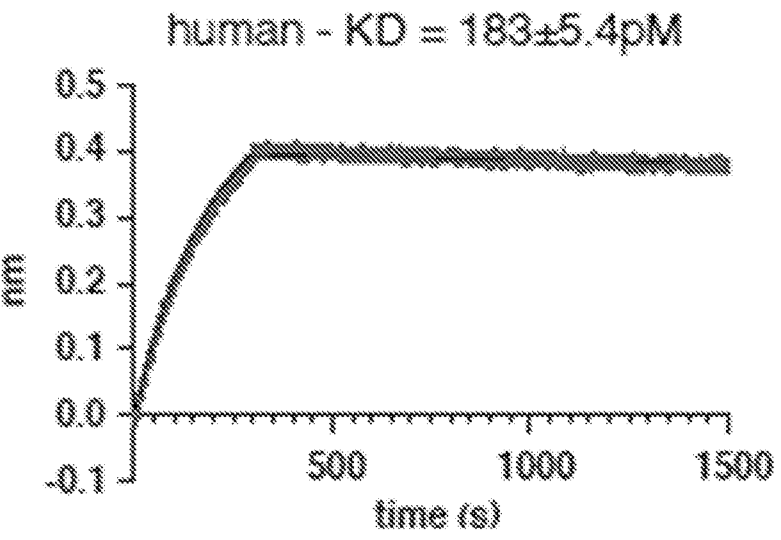
Figure 16B:
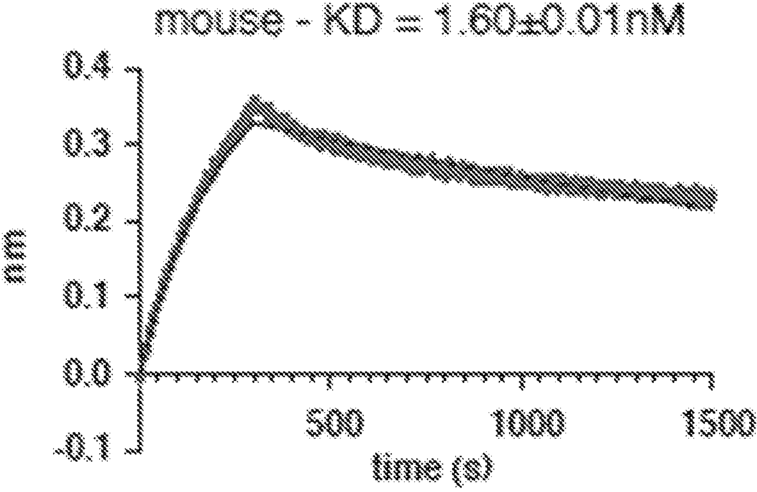
Figure 16C:
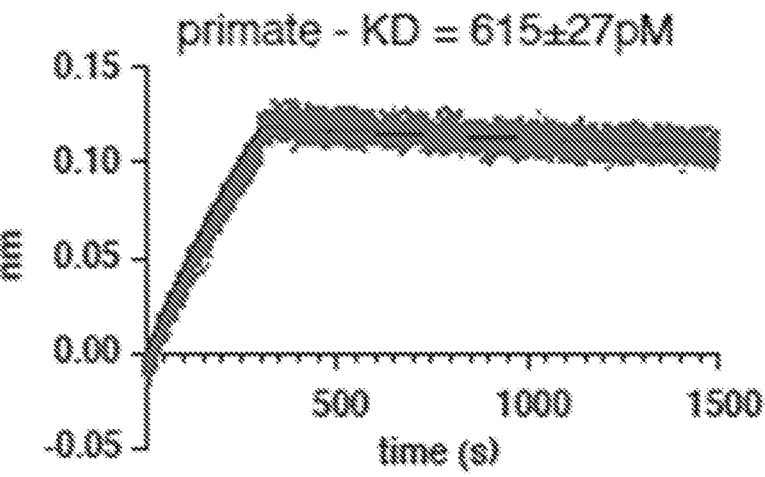
Figure 16D:
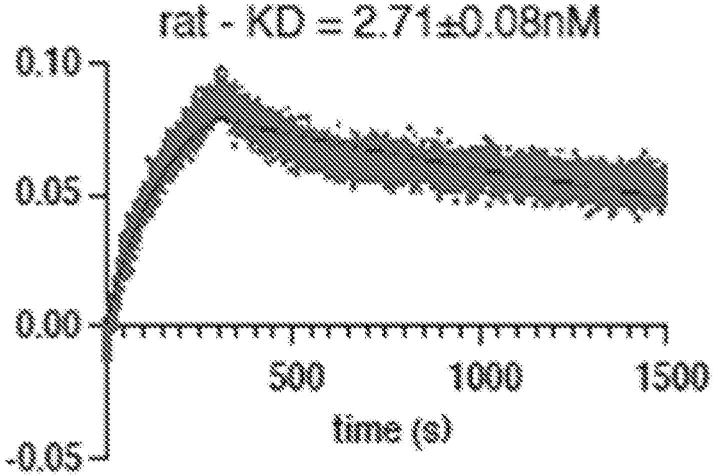

FIG. 15 includes a graph showing the fraction of annexin V- and propidium iodide (PI)-positive cells plotted as a function of antibody concentration used. MOLM-13 cells were co-incubated with varying concentrations of either G9.2-17 or human IgG4 isotype antibody and recombinant human Galectin-9 for 16 hours. Cells were stained with annexin V and propidium iodide prior to analysis by flow cytometry. Each condition was performed in triplicate. Analysis was performed on FlowJo software.

FIGS. 16A-16D include graphs showing biolayer interferometry analysis to measure binding affinity to human (FIG. 16A), mouse (FIG. 16B), primate (FIG. 16C) or rat (FIG. 16D) gal-9 CRD2. G9.2-17 was captured onto anti-Fab probes and incubated either recombinant human, mouse, primate or rat gal-9 CRD2. Global fit, shown in black line, was used to calculate the dissociation constants. Representative data from triplicate runs shown. Results indicate G9.2-17 binds tightly to and is cross reactive with human, mouse, primate and rat Galectin-9.

Figure 17:
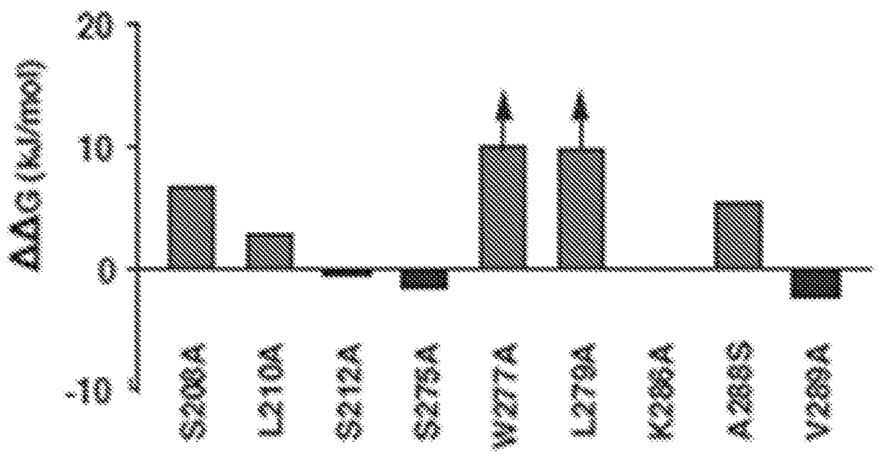

FIG. 17 depicts a bar graph showing the results of epitope mapping studies of gal-9 CRD2 using alanine scanning to characterize G9.2-17 binding. Galectin-9 CRD2 mutants were generated using site-directed mutagenesis. Mutants were immobilized onto streptavidin coated beads and G9.2-17 was titrated to generate a saturation curve. KD values were calculated by fitting curves to Michaelis Menton kinetics. ΔΔG values of binding for each mutant versus wild-type galectin shown. Arrows indicate values that are outside the limit of detection for the assay. Higher ΔΔG values represent greater contribution to G9.2-17 epitope. Mutations were mapped onto the surface of gal CRD2 crystal structure (PDB 3nv4). Residues shown in red represent mutations that resulted in reduction or loss of G9.2-17 binding.

Figure 18:
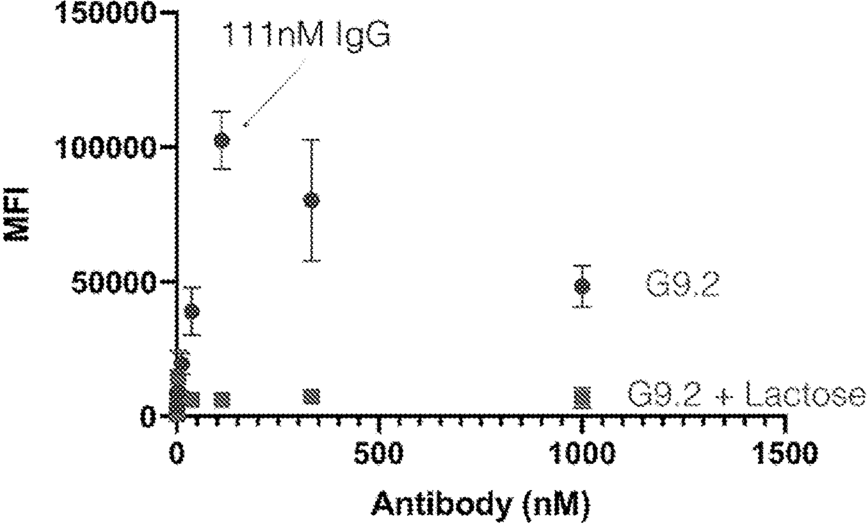

FIG. 18 depicts a graph showing the results of a binding assay in which muscle-specific kinase (MuSK) extracellular region (ECR) (known to contain carbohydrate regions which are used as unspecific carbohydrate regions for the purpose of this assay) was immobilized on beads and binding of monomeric galectin-9 CRD2 was detected in the presence or absence of lactose with G9.2-17 or G9.2-17 alone.

Figure 19:
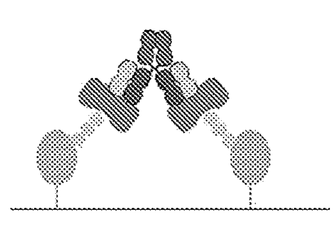
Figure 19:
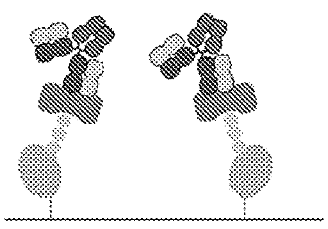
Figure 19:
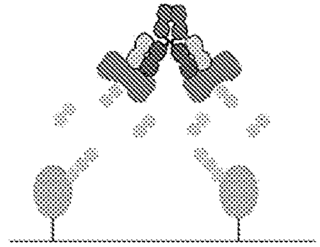

FIG. 19 depicts a schematic showing one antibody binding to two CRD2 monomers at a relatively lower antibody to CRD2 domain ratio (right panel) resulting in increased avidity to CRD2, two antibodies separately binding to two CRD2 monomers at a relatively higher antibody to CRD2 domain ratio and achieving affinity not avidity (middle panel) and disruption of carbohydrate CRD2 interaction in the presence of lactose+LYT-200 (right panel).

Figure 20:
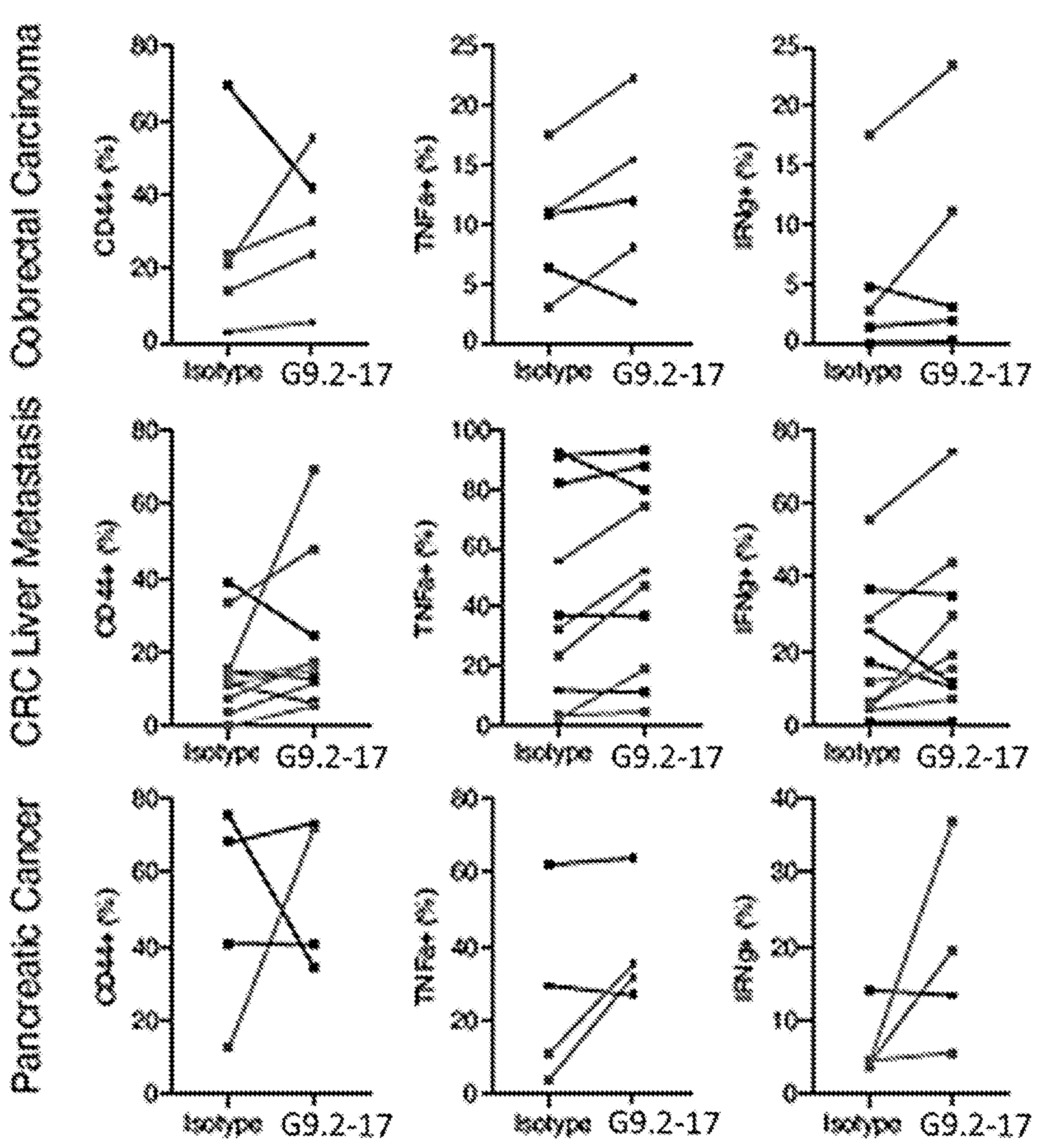

FIG. 20 depicts graphs showing a summary of immune profiling in PDOTS from pancreatic cancer, CRC liver metastasis, and colorectal carcinoma, some of the individual results of which are shown elsewhere herein. G9.2-17 activates T cells in PDOTS tumor cultures. PDOTS were treated with G9.2-17 hIgG4 or isotype for three days. Expression of CD44, IFNγ, and TNFα in CD3+ T cells from PDOTS. A total of 16 PDOTs were treated using tumors from gall bladder, pancreatic, colorectal cancers and colorectal carcinoma liver metastasis. Responders determined as 20% increase in response in two of three measured criteria.

Figure 21:
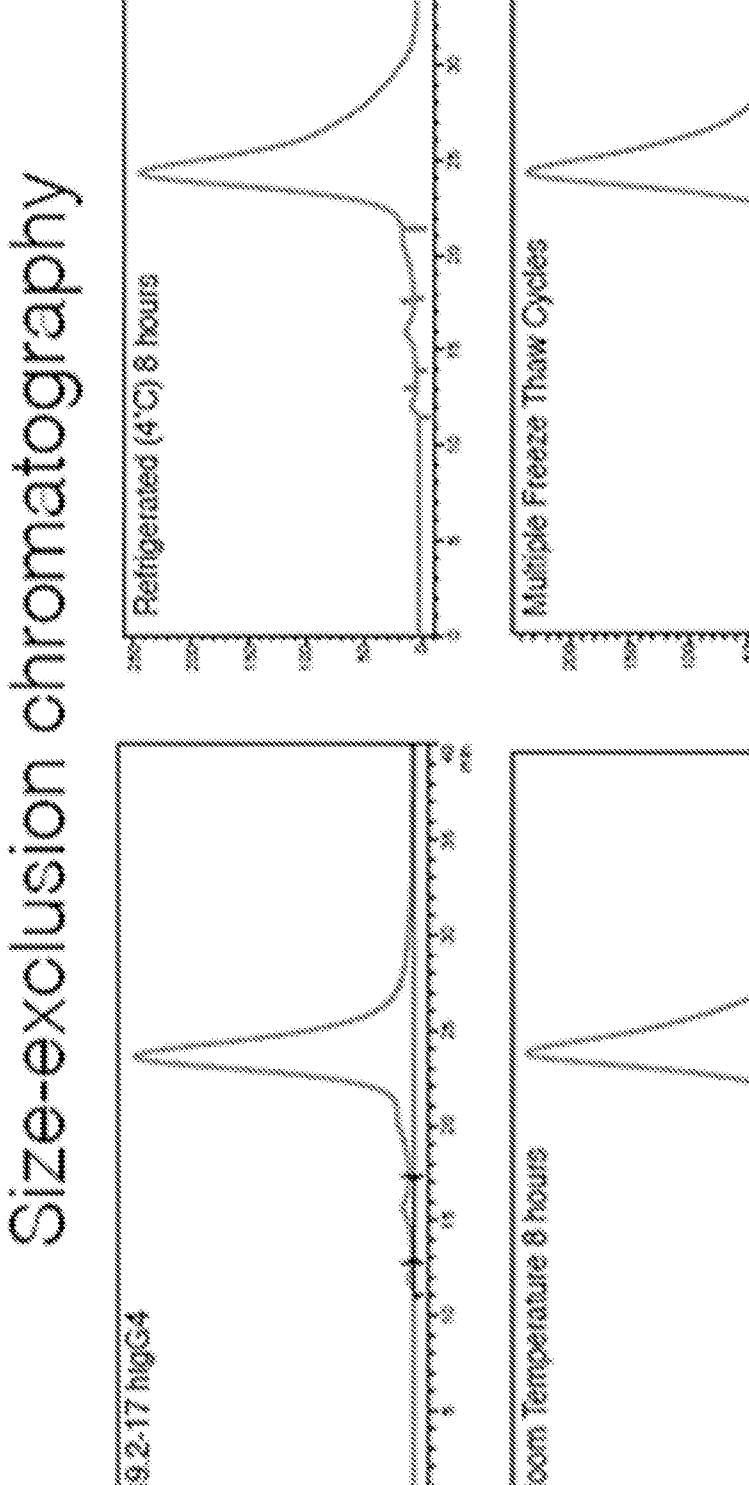

FIG. 21 depicts graphs showing the size exclusion exchange chromatography (SEC) profiles for the anti-Galectin-9 antibody G9.2-17 IgG4. The high molecular weight peaks are labeled. In the upper left panel is a graph showing a representative size exclusion chromatography (SEC) profile for the anti-Galectin-9 antibody. In the upper right panel is a graph showing size exclusion chromatography (SEC) profile for the anti-Galectin-9 antibody after refrigeration for 8 hours at 4 C. In the lower left panel is a graph showing size exclusion chromatography (SEC) profile for the anti-Galectin-9 antibody after storage at room temperature for 8 hours. In the lower right panel is a graph showing size exclusion chromatography (SEC) profile for the anti-Galectin-9 antibody after multiple freeze/thaw cycles.

Figure 22A:
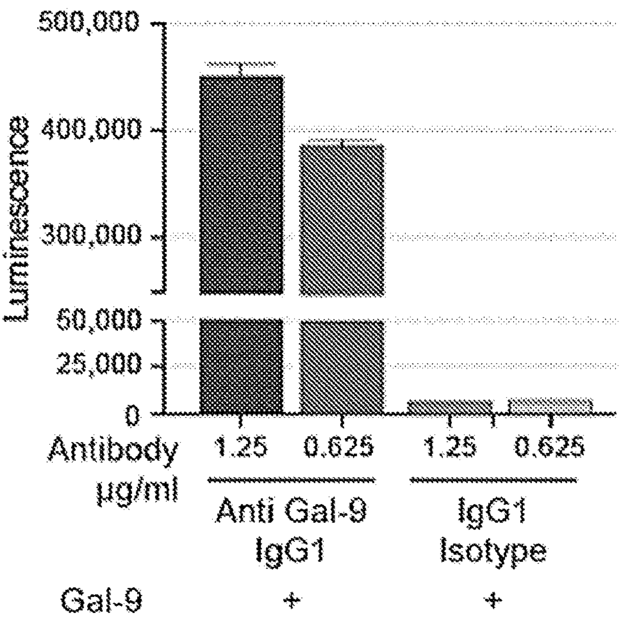
Figure 22B:
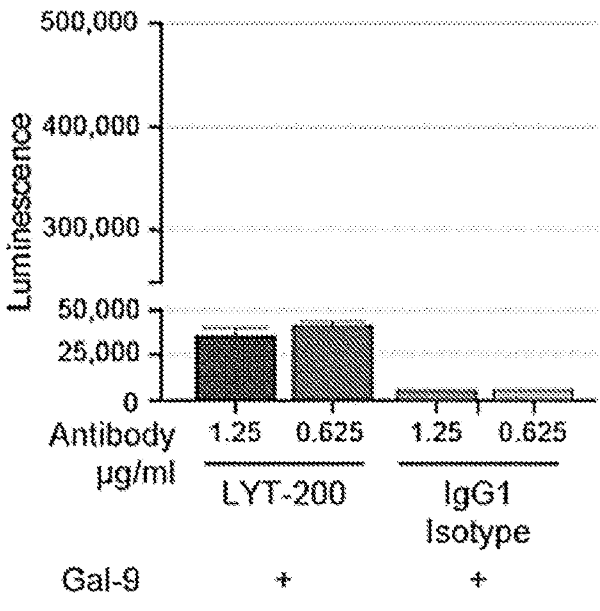

FIGS. 22A and 22B depict graphs showing the results of ADCC assays performed with the IgG1 form of G9.2-17 (FIG. 22A) and the IgG4 form of G9.2-17 (FIG. 22B). As expected for a human IgG4 mAb, G9.2-17 does not mediate ADCC (FIG. 22B). This was tested against the IgG1 human counterpart of G9.2-17 as a positive control, which mediates ADCC and ADCP, as expected (FIG. 22A).

Figure 23A:
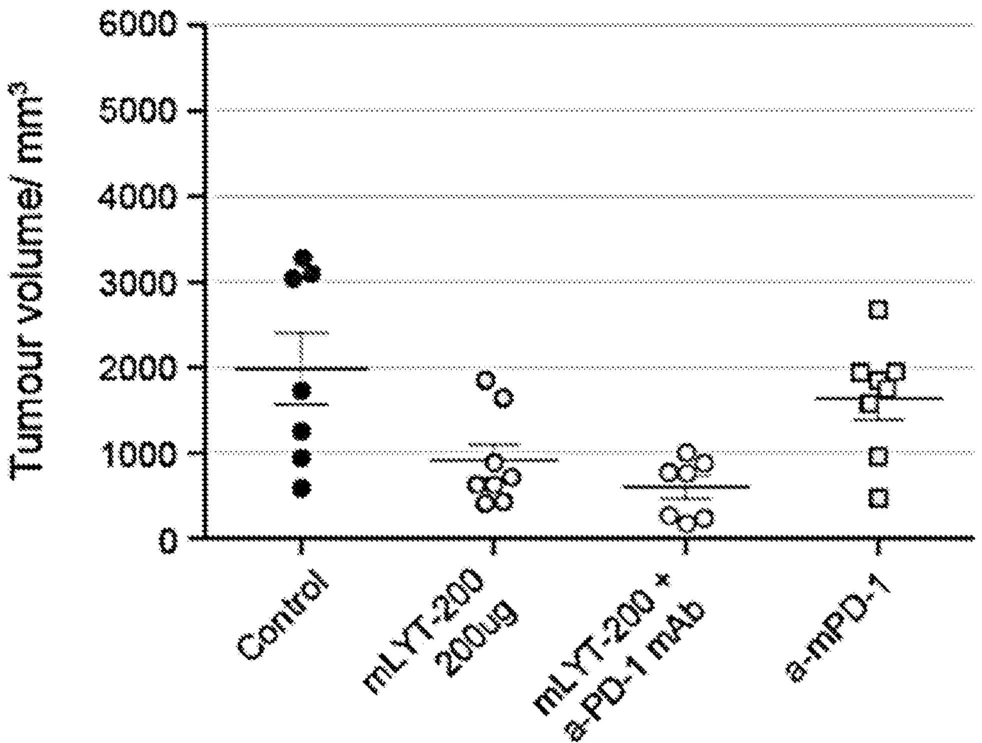
Figure 23B:
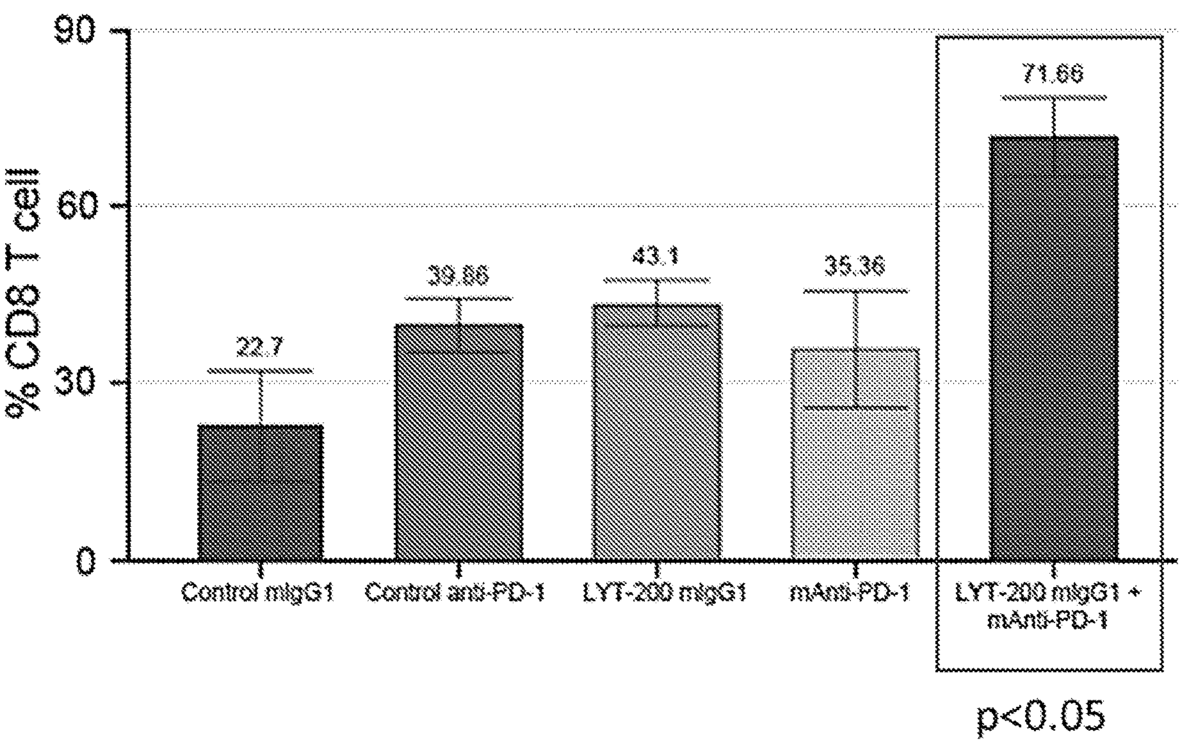

FIGS. 23A and 23B depict graphs showing the effect of 9.2-17 in a B16F10 subcutaneous syngeneic model. Tumors were engrafted subcutaneously and treated with G9.2-17 IgG1 mouse mAb, anti-PD1 antibody or a combination of G9.2-17 IgG1 mouse mAb and anti-PD1 antibody.

FIG. 23A depicts a graph showing the effect on tumor volume. FIG. 23B depicts a graph showing intratumoral CD8 T cell infiltration. Results show that intra-tumoral presence effector T cells were enhanced in the combination arm.

Figure 24A:
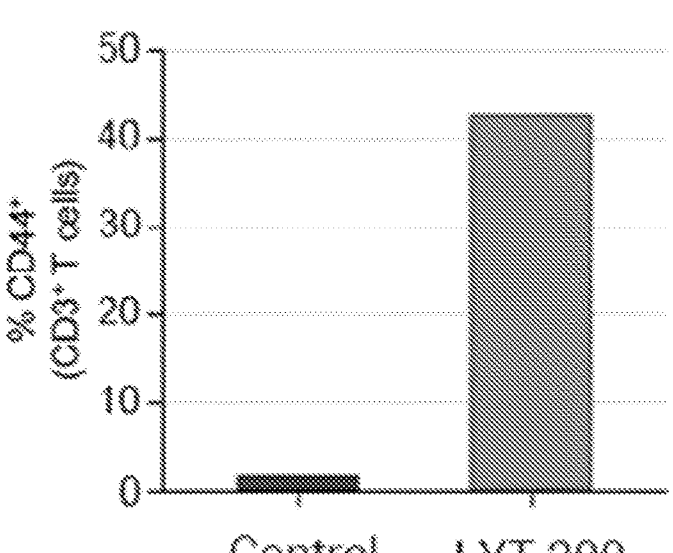
Figure 24B:
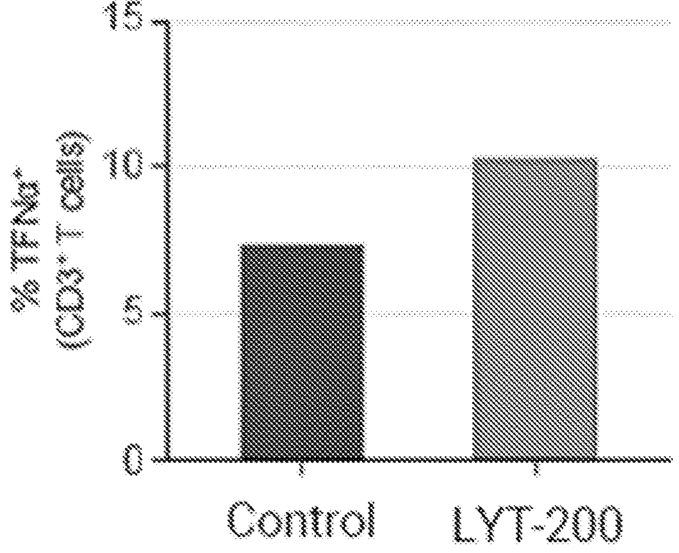

FIGS. 24A and 24B include charts showing cholangiocarcinoma patient-derived tumor cultures ex vivo (organoids) treated with G9.2-17. Patient derived tumor cultures ex vivo (organoids) were treated with G9.2-17 or isotype control for three days. Expression of CD44 (FIG. 24A), and TNFα (FIG. 24B) in CD3+ T cells from PDOTS was assessed.

DETAILED DESCRIPTION OF INVENTION

Galectin-9, a tandem-repeat lectin, is a beta-galactoside-binding protein, which has been shown to have a role in modulating cell-cell and cell-matrix interactions. It is found to be strongly overexpressed in Hodgkin's disease tissue and in other pathologic states. It may also be found circulating in the tumor microenvironment (TME).

Galectin-9 is found to interact with Dectin-1, an innate immune receptor which is highly expressed on macrophages in PDA, as well as on cancer cells (Daley D, et al. Dectin 1 activation on macrophages by galectin 9 promotes pancreatic carcinoma and peritumoral immune tolerance; *Nat Med.* 2017; 23(5):556-6). Regardless of the source of Galectin-9, disruption of its interaction with Dectin-1 has been shown to lead to the reprogramming of $CD4^+$ and $CD8^+$ cells into indispensable mediators of anti-tumor immunity. Thus, Galectin-9 serves as a valuable therapeutic target for blocking the signaling mediated by Dectin-1. Accordingly, in some embodiments, the anti-Galectin-9 antibodies describe herein disrupt the interaction between Galectin-9 and Dectin-1.

Galectin-9 is also found to interact with TIM-3, a type I cell surface glycoprotein expressed on the surface of leukemic stem cells in all varieties of acute myeloid leukemia (except for M3 (acute promyelocytic leukemia)), but not expressed in normal human hematopoietic stem cells (HSCs). TIM-3 signaling resulting from Galectin-9 ligation has been found to have a pleiotropic effect on immune cells, inducing apoptosis in Th1 cells (Zhu et al., *Nat Immunol.,* 2005, 6:1245-1252) and stimulating the secretion of tumor necrosis factor-α (TNF-α), leading to the maturation of monocytes into dendritic cells, resulting in inflammation by innate immunity (Kuchroo et al., *Nat Rev Immunol.,* 2008, 8:577-580). Further Galectin-9/TIM-3 signaling has been found to co-activate NF-κB and β-catenin signaling, two pathways that promote leukemia stem cells (LSC) self-renewal (Kikushige et al., *Cell Stem Cell,* 2015, 17(3):341-352). An anti-Galectin-9 antibody that interferes with Galectin-9/TIM-3 binding could have a therapeutic effect, especially with respect to leukemia and other hematological malignancies. Accordingly, in some embodiments, the anti-Galectin-9 antibodies described herein disrupt the interaction between Galectin-9 and TIM-3.

Galectin-9 is also found to interact with CD206, a mannose receptor highly expressed on M2 polarized macrophages, thereby promoting tumor survival (Enninga et al., *J Pathol.* 2018 August; 245(4):468-477). Tumor-associated macrophages expressing CD206 are mediators of tumor immunosuppression, angiogenesis, metastasis, and relapse (see, e.g., Scodeller et al., *Sci Rep.* 2017 Nov. 7; 7(1):14655, and references therein). Specifically, M1 (also termed classically activated macrophages) are trigged by Th1-related cytokines and bacterial products, express high levels of IL-12, and are tumoricidal. By contrast, M2 (so-called alternatively activated macrophages) are activated by Th2-related factors, express high level of anti-inflammatory cytokines, such as IL-10, and facilitate tumor progression (Biswas and Mantovani; *Nat Immunol.* 2010 October; 11(10):889-96). The pro-tumoral effects of M2 include the promotion of angiogenesis, advancement of invasion and metastasis, and the protection of the tumor cells from chemotherapy-induced apoptosis (Hu et al., *Tumour Biol.* 2015 December; 36(12): 9119-9126, and references therein). Tumor-associated macrophages are thought be of M2-like phenotype and have a protumor role. Galectin-9 has been shown to mediate myeloid cell differentiation toward an M2 phenotype (Enninga et al., *Melanoma Res.* 2016 October; 26(5):429-41). It is possible that Galectin-9 binding CD206 may result in reprogramming tumor-associated macrophages (TAMs) towards the M2 phenotype, similar to what has been previously shown for Dectin. Without wishing to be bound by theory, blocking the interaction of Galectin-9 with CD206 may provide one mechanism by which an anti-Galectin antibody, e.g., as described herein in Table 1 and Table 2, such as antibody 9.1-8m13 and/or antibody 9.2-17, can be therapeutically beneficial. Accordingly, in some embodiments, the anti-Galectin-9 antibodies described herein disrupt the interaction between Galectin-9 and CD206.

Galectin-9 has also been shown to interact with protein disulfide isomerase (PDI) and 4-1BB (Bi S, et al. *Proc Natl Acad Sci USA.* 2011; 108(26):10650-5; Madireddi et al. *J Exp Med.* 2014; 211(7):1433-48).

Provided herein are antibodies capable of binding to Galectin-9 (e.g., human, mouse, or both) and methods and uses thereof, either alone or in combination with a checkpoint inhibitor (e.g., an anti-PD1 antibody or an anti-PD-L1 antibody) for modulating (e.g., increasing) an immune response. In some embodiments, the modulation (e.g., increasing) of an immune response comprises increasing production of one or more cytokines (e.g., interferon γ (IFNg)) and/or enhancing a T cell population (e.g., CD8+ cells). In some embodiments, the disclosure provides methods for modulating (e.g., increasing) an immune response in a subject, including a human subject, e.g., having or suspected of having or at risk of having a cancer, comprising administering to the subject a therapeutically effective amount of one or more anti-galetin-9 antibodies described herein, alone or in combination with a checkpoint inhibitor (e.g., an anti-PD1 antibody or an anti-PD-L1 antibody).

Antibodies Binding to Galectin-9

The present disclosure provides antibodies that bind Galectin-9, for example, human and/or mouse Galectin-9.

In some instances, the anti-Galectin antibody described herein binds to an epitope in a carbohydrate recognition domain (CRD) of Galectin-9, e.g., CRD2. Such an antibody specifically binds CRD2 of a Galectin-9 polypeptide, such as a human Galectin-9 polypeptide, or an epitope within the CRD2 fragment. In some instances, the anti-Galectin antibody does not bind CRD1 of the same Galectin-9 polypeptide. An antibody that does not bind to a target antigen means that no significant level of binding can be observed in a conventional assay for determining antibody binding activity to the target antigen, e.g., in an ELISA assay, for example, no detectable binding activity in the assay. Galectin-9 is a protein well known in the art. For example, NCBI GenBank Accession Nos. BAB83625.1 and NP_034838.2 provide information for human and mouse Galectin-1, respectively. Provided herein are exemplary human and mouse Galectin-9 polypeptides. The amino acid sequences of human galectin-9 (isoform 1; aka "long") and human galectin-9 (isoform 2; aka "short") are provided below as SEQ ID: NO: 1 and SEQ ID NO: 2, respectively.

```
Amino acid sequence of human Galectin-9 (isoform 1, GenBank Accession No.
BAB83625.1; SEQ ID NO: 1)
  1 mafsgsqapy lspavpfsgt iqggladglq itvngtvlss sgtrfavnfq tgfsgndiaf

 61 hfnprfedgg yvvcntrqng swgpeerkth mpfqkgmpfd lcflvqssdf kvmvngilfv

121 qyfhrvpfhr vdtisvngsv qlsyisfqnp rtvpvqpafs tvpfsqpvcf pprprgrrqk

181 ppgvwpanpa pitqtvihtv qsapgqmfst paippmmyph paypmpfitt ilgglypsks

241 illsgtvlps aqrfhinlcs gnhiafhlnp rfdenavvrn tqidnswgse erslprkmpf

301 vrgqsfsvwi lceahclkva vdgqhlfeyy hrlrnlptin rlevggdigl thvqt

Amino acid sequence of human Galectin-9 (isoform 2, UniProt ID 000182-2;
SEQ ID NO: 2)
MAFSGSQAPY LSPAVPFSGT IQGGLQDGLQ ITVNGTVLSS SGTRFAVNFQ TGESGNDIAF

HFNPRFEDGG YVVCNTRQNG SWGPEERKTH MPFQKGMPFD LCFLVQSSDF KVMVNGILFV

QYFHRVPFHR VDTISVNGSV QLSYISFQPP GVWPANPAPI TQTVIHTVQS APGQMESTPA

IPPMMYPHPA YPMPFITTIL GGLYPSKSIL LSGTVLPSAQ RFHINLCSGN HIAFHLNPRF

DENAVVRNTQ IDNSWGSEER SLPRKMPFVR GQSFSVWILC EAHCLKVAVD GQHLFEYYHR

LRNLPTINRL EVGGDIQLTH VQT
```

The CRD1 domain of human Galectin-9 (SEQ ID NO: 3) encompasses residues 1-148 of SEQ ID NO: 1 (boldface and italicized), and the CRD2 domain (SEQ ID NO: 4) spans residues 218-355 of SEQ ID NO: 1 (boldface and underlined). Similarly, the CRD1 domain of murine Galectin-9 (SEQ ID NO: 5) spans residues 1-147 of SEQ ID NO: 2 (boldface and italicized), and the CRD2 domain (SEQ ID NO: 6) spans residues 226-323 of SEQ ID NO: 2 (boldface and underlined).

Galectin-9 polypeptides from other species are known in the art and can be obtained from publicly available gene database, for example, GenBank, using either the human sequence or the mouse sequence as a query. The CRD1 and CRD2 domains of a Galectin-9 polypeptide can be identified by aligning the sequence of that Galectin-9 polypeptide with that of the human or mouse Galectin-9 as described herein.

The antibodies described herein bind Galectin-9 or a fragment thereof (e.g., CRD2). As used herein, the term "anti-Galectin-9 antibody" refers to any antibody capable of binding to a Galectin-9 polypeptide, which can be of a suitable source, for example, human or a non-human mammal (e.g., mouse, rat, rabbit, primate such as monkey, etc.). In some embodiments, the anti-Galectin-9 antibody can be used therapeutically to suppress the bioactivity of Galectin-9. In some embodiments, the anti-Galectin-9 antibody may be used in research or may be used in diagnostic/prognostic methods, e.g., for the detection of cells expressing Galectin-9 in an assessment of treatment eligibility and/or efficacy. Alternatively, or in addition, an anti-Galectin-9 antibody may block the interaction between Galectin-9 and its ligand (e.g., Dectin-1, TIM-3), thereby suppressing the signaling pathway triggered by, for example, a Galectin-9/Dectin-1 or Galectin-9/TIM-3 interaction. An anti-Galectin-9 antibody may also elicit the death of cells expressing Galectin-9, for example, through an antibody-dependent cellular cytotoxicity (ADCC) mechanism.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody", e.g., anti-Galectin-9 antibody, encompasses not only intact (e.g., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody, e.g., anti-Galectin-9 antibody, includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgAQ1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, the EU definition, and/or the contact definition, all of which are well known in the art. See, e.g., Kabat, E. A., et al. (1991) *Sequences of Proteins of Immunological Interest*, Fifth Edition, U.S. Department of Health and Human Services, NIH Publication No. 91-3242, Chothia et al., (1989) *Nature* 342:877; Chothia, C. et al. (1987) *J. Mol. Biol.* 196:901-917, Al-lazikani et al (1997) *J. Molec. Biol.* 273:927-948; Edelman et al., *Proc Natl Acad Sci USA*. 1969 May; 63(1):78-85; and Almagro, *J. Mol.* Recognit. 17:132-143 (2004). See also hgmp.mrc.ac.uk and bioinf.org.uk/abs). Correspondence or alignments between C numberings according to different definitions can for example be A found at www.imgt.org/.

The anti-Galectin-9 antibody described herein may be a full-length antibody, which contains two heavy chains and two light chains, each including a variable domain and a constant domain. Alternatively, the anti-Galectin-9 antibody can be an antigen-binding fragment of a full-length antibody. Examples of binding fragments encompassed within the term "antigen-binding fragment" of a full length antibody include (i) a Fab fragment, a monovalent fragment consisting of the $V_L$, $V_H$, $C_L$ and $C_H1$ domains; (ii) a $F(ab')_2$ fragment, a bivalent fragment including two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) that retains functionality. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

The anti-Galectin-9 antibody as described herein, e.g., in Table 1 and/or Table 2, can bind and inhibit (e.g., reduce or eliminate) the activity of Galectin-9. In some embodiments, the anti-Galectin-9 antibody as described herein can bind and inhibit the activity of Galectin-9 by at least 30% (e.g., 31%, 35%, 40%, 45%, 50%, 60%, 70%, 80%, 90%, 95% or greater, including any increment therein). The apparent inhibition constant ($Ki^{app}$ or $K_{i,app}$), which provides a measure of inhibitor potency, is related to the concentration of inhibitor required to reduce enzyme activity and is not dependent on enzyme concentrations. The inhibitory activity of an anti-Galectin-9 antibody described herein can be determined by routine methods known in the art.

The $$K_{i,}^{app}$$

value of an antibody may be determined by measuring the inhibitory effect of different concentrations of the antibody on the extent of the reaction (e.g., enzyme activity); fitting the change in pseudo-first order rate constant (v) as a function of inhibitor concentration to the modified Morrison equation (Equation 1) yields an estimate of the apparent Ki value. For a competitive inhibitor, the $Ki^{app}$ can be obtained from the y-intercept extracted from a linear regression analysis of a plot of $$K_{i,}^{app}$$

versus substrate concentration.

$$v = A \cdot \frac{([E] - [I] - K_i^{app}) + \sqrt{([E] - [I] - K_i^{app})^2 + 4[E] \cdot K_i^{app}}}{2} \quad \text{(Equation 1)}$$

Where A is equivalent to $v_0/E$, the initial velocity ($v_0$) of the enzymatic reaction in the absence of inhibitor (I) divided by the total enzyme concentration (E). In some embodiments, the anti-Galectin-9 antibody described herein may have a $Ki^{app}$ value of 1000, 900, 800, 700, 600, 500, 400, 300, 200, 100, 50, 40, 30, 20, 19, 18, 17, 16, 15, 14, 13, 12, 11, 10, 9, 8, 7, 6, 5 pM or less for the target antigen or antigen epitope. In some embodiments, the anti-Galectin-9 antibody may have a lower $Ki^{app}$ for a first target (e.g., the CRD2 of Galectin-9) relative to a second target (e.g., CRD1 of the Galectin-9). Differences in $Ki^{app}$ (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some examples, the anti-Galectin-9 antibody inhibits a first antigen (e.g., a first protein in a first conformation or mimic thereof) greater relative to a second antigen (e.g., the same first protein in a second conformation or mimic thereof, or a second protein). In some embodiments, any of the anti-Galectin-9 antibodies may be further affinity matured to reduce the 10 $Ki^{app}$ of the antibody to the target antigen or antigenic epitope thereof.

In some embodiments, any of the anti-Galectin-9 antibodies described herein, either taken alone or in combination with a checkpoint inhibitor, induce T cell activation, e.g., in tumor infiltrating T cells, i.e., suppress Galectin-9 mediated inhibition of T cell activation, either directly or indirectly. In some embodiments, the anti-Galectin-9 antibody promotes T cell activation by at least 20%, 30% (e.g., 20%, 21%, 25%, 30%, 35%, 40%, 50%, 60%, 70%, 80%, 90%, 95% or greater, including any increment therein). T cell activation can be determined by conventional methods or the assays described herein (e.g., measurement of CD44, OX40, IFNgamma, and/or PD-1). In some embodiments, the anti-Galectin-9 antibody promotes CD4+ cell activation by at least 20% (e.g., 20%, 21%, 25%, 30%, 35%, 40%, 50%, 60%, 70%, 80%, 90%, 95% or greater, including any increment therein). In a non-limiting example, the anti-Galectin antibody induces CD44 expression in CD4+ cells. In some embodiments, the anti-Galectin-9 antibody increases CD44 expression in CD4+ cells by at least 20% (e.g., 20%, 21%, 25%, 30%, 35%, 40%, 50%, 60%, 70%, 80%, 90%, 95% or greater, including any increment therein). In a non-limiting example, the anti-Galectin antibody induces IFNgamma expression in CD4+ cells. In some embodiments, the anti-Galectin-9 antibody increases IFNgamma expression in CD4+ cells by at least 20% (e.g., 20%, 21%, 25%, 30%, 40%, 50%, 60%, 70%, 80%, 90%, 95% or greater, including any increment therein). In a non-limiting example, the anti-Galectin antibody induces TNFalpha expression in CD4+ cells. In some embodiments, the anti-Galectin-9 antibody increases TNFalpha expression in CD4+ cells by at least 20% (e.g., 20%, 21%, 25%, 30%, 35%, 40%, 50%, 60%, 70%, 80%, 90%, 95% or greater, including any increment therein). In any of these embodiments, the T cell activation is induced as compared with the level found prior to anti-Galectin antibody and/or checkpoint inhibitor treatment.

In some embodiments, the anti-Galectin-9 antibody promotes CD8+ cell activation by at least 20% (e.g., 20%, 21%, 25%, 30%, 40%, 50%, 60%, 70%, 80%, 90%, 95% or greater), including any increment therein). In a non-limiting example, the anti-Galectin antibody induces CD44 expression in CD8+ cells. In some embodiments, the anti-Galectin-9 antibody increases CD44 expression in CD8+ cells by at least 20% (e.g., 21%, 25%, 30%, 40%, 50%, 60%, 70%, 80%, 90%, 95% or greater, including any increment therein). In a non-limiting example, the anti-Galectin antibody induces IFNgamma expression in CD8+ cells. In some embodiments, the anti-Galectin-9 antibody increases IFNgamma expression in CD8+ cells by at least 20% (e.g., 21%, 25%, 30%, 40%, 50%, 60%, 70%, 80%, 90%, 95% or greater, including any increment therein). In a non-limiting example, the anti-Galectin antibody induces TNFalpha expression in CD8+ cells. In some embodiments, the anti-Galectin-9 antibody increases TNFalpha expression in CD8+ cells by at least 20% (e.g., 21%, 25%, 30%, 40%, 50%, 60%, 70%, 80%, 90%, 95% or greater, including any increment therein). In any of these embodiments, the CD8+ cell activation is induced as compared with the level found prior to anti-Galectin antibody and/or checkpoint inhibitor treatment.

The antibodies described herein can be murine, rat, human, or any other origin (including chimeric or humanized antibodies). Such antibodies are non-naturally occurring, i.e., would not be produced in an animal without human act (e.g., immunizing such an animal with a desired antigen or fragment thereof or isolated from antibody libraries).

Any of the antibodies described herein, e.g., anti-Galectin-9 antibody, can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In some embodiments, the anti-Galectin-9 antibody is a humanized antibody. In some embodiments, the anti-Galectin-9 antibody is a humanized antibody having one of more of the elements or characteristics described below or elsewhere herein. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. In general, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In some instances, the humanized antibody may comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation.

Methods for constructing humanized antibodies are also well known in the art. See, e.g., Queen et al., *Proc. Natl. Acad. Sci. USA,* 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions can be used to substitute for the corresponding residues in the human acceptor genes.

In some embodiments, the anti-Galectin-9 antibody is a chimeric antibody. In some embodiments, the anti-Galectin-9 antibody is a chimeric antibody which may include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-Galectin-9 antibodies described herein specifically bind to the corresponding target antigen or an epitope thereof, e.g., Galectin-9 antigen or epitope. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (Galectin-9) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (i.e., only baseline binding activity can be detected in a conventional method). In some embodiments, the anti-Galectin-9 antibodies described herein specifically bind to Galectin-9. In some embodiments, the anti-Galectin-9 antibodies described herein specifically bind to the CRD2 of Galectin-9 or an epitope therein. Alternatively, or in addition, the anti-Galectin-9 antibody described herein specifically binds human Galectin-9 or a fragment thereof as relative to the mouse counterpart, or vice versa (e.g., having a binding affinity at least 10-fold higher to one antigen than the other as determined in the same assay under the same assay conditions).

In some embodiments, the anti-Galectin-9 antibody binds only to CRD1 (and not CRD2), for example, meaningful binding to CRD2 or binding to CRD2 is not detectable by a routine assay method. In some embodiments, the anti-Galectin-9 or a fragment thereof binds only to CRD2 (and not CRD1). In some embodiments, certain antibodies described herein may bind to both CRD1 and CRD2. In some embodiments, certain antibodies or fragments thereof described herein may bind to both CRD1 and CRD2, but with a lower affinity to CRD2. In some embodiments, certain antibodies or fragments thereof described herein may bind to both CRD1 and CRD2, but with a lower affinity to CRD1.

In some embodiments, the anti-Galectin-9 antibody may bind to an epitope at least a segment of which is in CRD1 of a galectin-9 protein (e.g., a human galectin-9 or a mouse galectin-9). In some embodiments, the antibody may bind an epitope which is entirely within the CRD1 of the Galectin-9 protein. In some embodiments, the antibody may bind an epitope which is partially within the CRD1 of the Galectin-9 protein. In some embodiments, the epitope to which the anti-Galectin antibody binds is a linear epitope. In some embodiments, the epitope to which the anti-Galectin antibody binds is a conformational epitope.

In some embodiments, the anti-Galectin-9 antibody may bind an epitope at least a segment of which is in CRD2 of a Galectin-9 protein (e.g., a human galectin-9 or a mouse galectin-9). In some embodiments, the anti-Galectin-9 antibody may bind an epitope which is entirely within the CRD2 of the Galectin-9 protein. In some specific embodiments in which the anti-Galectin-9 antibody binds an epitope partially or entirely within CDR2, the antibody binds an epitope comprising at least residue W309. In some specific embodiments, in which the anti-Galectin-9 antibody binds an epitope partially or entirely within CDR2, the epitope to which the anti-Galectin-9 antibody binds does not contain one or more of R253, R271, Y330, R334, R341, and Y236 of SEQ ID NO: 1. In some embodiments, the epitope to which the anti-Galectin antibody binds is a linear epitope encompassing residue W309. In some embodiments, the epitope to which the anti-Galectin antibody binds is a conformational epitope comprising W309.

In some specific embodiments in which the anti-Galectin-9 antibody binds an epitope partially or entirely within CDR2, the antibody binds an epitope comprising at least residue W277 of SEQ ID NO: 2. In some specific embodiments in which the anti-Galectin-9 antibody binds an epitope partially or entirely within CDR2, the antibody binds an epitope comprising at least residue L279 of SEQ ID NO: 2. In some specific embodiments in which the anti-Galectin-9 antibody binds an epitope partially or entirely within CDR2, the antibody binds an epitope comprising at least residue L279 and W277 of SEQ ID NO: 2. In some specific embodiments in which the anti-Galectin-9 antibody binds an epitope partially or entirely within CDR2, the antibody binds an epitope comprising at least one or more residues selected from S208, L210 and A288 of SEQ ID NO: 2. In some specific embodiments in which the anti-Galectin-9 antibody binds an epitope partially or entirely within CDR2, the antibody binds an epitope comprising at least residue one or more residues selected from S208, L210, A288, L279 and W277 of SEQ ID NO: 2. In some specific embodiments, in which the anti-Galectin-9 antibody binds an epitope partially or entirely within CDR2, the epitope to which the anti-Galectin-9 antibody binds does not contain one or more of residues R253, R271, Y330, R334, R341, and Y236 of SEQ ID NO: 1. In some specific embodiments, in which the anti-Galectin-9 antibody binds an epitope partially or entirely within CDR2, the epitope to which the anti-Galectin-9 antibody binds does not contain R239 of SEQ ID NO: 2.

An "epitope" refers to the site on a target antigen that is recognized and bound by an antibody. The site can be entirely composed of amino acid components, entirely composed of chemical modifications of amino acids of the protein (e.g., glycosyl moieties), or composed of combinations thereof. Overlapping epitopes include at least one common amino acid residue. An epitope can be linear, which is typically 6-15 amino acids in length. Alternatively, the epitope can be conformational. The epitope to which an antibody binds can be determined by routine technology, for example, the epitope mapping method (see, e.g., descriptions below).

In some embodiments, an antibody might bind to both CRD1 and CRD2. In other instances, the anti-Galectin-9 antibody described herein may cross-react to human and a non-human Galectin-9 (e.g., mouse), e.g., the difference in binding affinity to the human and the non-human Galectin-9 is less than 5-fold, e.g., less than 2-fold, or substantially similar.

In some embodiments, an anti-Galectin-9 antibody as described herein has a suitable binding affinity for the target antigen (e.g., Galectin-9) or antigenic epitopes thereof. As used herein, "binding affinity" refers to the apparent association constant or $K_A$. The $K_A$ is the reciprocal of the dissociation constant ($K_D$). The anti-Galectin-9 antibody described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the anti-Galectin-9 antibodies described herein have a higher binding affinity (a higher $K_A$ or smaller $K_D$) to the CRD1 of Galectin-9 as compared to the binding affinity to the CRD2 of Galectin-9. In some embodiments, the anti-Galectin-9 antibodies described herein have a higher binding affinity (a higher $K_A$ or smaller $K_D$) to the CRD2 of Galectin-9 as compared to the binding affinity to the CRD1 of Galectin-9. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the anti-Galectin-9 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20).

These techniques can be used to measure the concentration of bound binding protein as a function of target protein concentration. Under certain conditions, the fractional concentration of bound binding protein ([Bound]/[Total]) is generally related to the concentration of total target protein ([Target]) by the following equation:

$$[\text{Bound}]/[\text{Total}] = [\text{Target}]/(\text{Kd} + [\text{Target}])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay. In some cases, the in vitro binding assay is indicative of in vivo activity. In other cases, the in vitro binding assay is not necessarily indicative of in vivo activity. In some cases tight binding is beneficial, but in other cases tight binding may not be as desirable in vivo, and an antibody with lower binding affinity may be more desirable. A number of exemplary anti-Galectin-9 antibodies (specific to CRD1 or CRD2) are provided herein.

An exemplary antibody clone (reference antibody) of the disclosure binding to CRD1 includes G9.1-8m13. Exemplary antibody clones (reference antibodies) of the disclosure binding to CRD2 include G9.2-17 and its variant G9.2-17mut6. The structural features of the exemplary antibodies, including heavy chain and light chain variable region sequences and the complementary determining regions therein, are provided in Tables 1 and 2 below.

TABLE 1

Antibodies directed against CRD1

| Clone | Sequence | SEQ ID NO: |
|---|---|---|
| G9.1-8m13 | $V_L$: DIQMTQSPSSLSASVGDRVTITC**RASQSVSSAVA**WYQQKPGKAPKLLIY**SASSLYS**GVPSRFSGSRSGTDFTLTISSLQPEDFATYYC**QQSYYDSNPIT**FGQGTKVEIKR | 7 |
| G9.1-8m13 | $V_H$: EVQLVESGGGLVQPGGSLRLSCAASG**FTVSSSSIH**WVRQAPGKGLEWVA**YIYPYSSSSYADSVKG**RFTISADTSKNTAYLQMNSLRAEDTAVYYCAR**YSTYSSKWVWGMDY**WGQGTLVTVSS | 8 |

TABLE 2

Antibodies directed against CRD2

| Clone | Sequence | SEQ ID NO: |
|---|---|---|
| G9.2-17 | $V_L$: DIQMTQSPSSLSASVGDRVTITC**RASQSVSSAVA**WYQQKPGKAPKLLIY**SASSLYS**GVPSRFSGSRSGTDFTLTISSLQPEDFATYYC**QQSSTDPIT**FGQGTKVEIKR | 9 |
| G9.2-17 | $V_H$: EVQLVESGGGLVQPGGSLRLSCAASG**FTVSSSSIH**WVRQAPGKGLEWVA**YISSSSGYTYYADSVKG**RFTISADTSKNTAYLQMNSLRAEDTAVYYCPAR**YWSYSWWPYRGMDY**WGQGTLVTVSS | 10 |
| G9.2-17mut6 | $V_L$: DIQMTQSPSSLSASVGDRVTITC**RASQSVSSAVA**WYQQKPGKAPKLLIY**SASSLYS**GVPSRFSGGSRSTDFTLTISSLQPEDFATYYC**QQSSTDPIT**FGQGTKVEIKR | 11 |
| G9.2-17mut6 (mutation underlined) | $V_H$: EVQLVESGGGLVQPGGSLRLSCAASG**FTVSSSSIH**WVRQAPGKGLEWVA**YISSSSGYTYYADSVKG**RFTISADTSKNTAYLQMNSLRAEDTAVYYCAR**YWSYPSWSPYRGMDY**WGQGTLVTVSS | 12 |

The heavy chain and light chain complementary determining regions determined by the Kabat scheme of the exemplary anti-galectin 9 antibodies listed in Tables 1 and 2 above are provided in Table 3 below.

TABLE 3

CDR Sequences of Exemplary Anti-Gal-9 Antibodies

| Clone | | CDR Sequences | SEQ ID NO: |
|---|---|---|---|
| G9.1-8m13 | $V_L$ CDR1 | RASQSVSSAVA | 13 |
| | $V_L$ CDR2 | SASSLYS | 14 |
| | $V_L$ CDR3 | QQSYYDSNPIT | 15 |
| | $V_H$ CDR1 | FTVSSSSIH | 16 |
| | $V_H$ CDR2 | YIYPYSSSSYADSVKG | 17 |
| | $V_H$ CDR3 | YSTYSSKWVWGMDY | 18 |
| G9.2-17 | $V_L$ CDR1 | RASQSVSSAVA | 19 |
| | $V_L$ CDR2 | SASSLYS | 20 |
| | $V_L$ CDR3 | QQSSTDPIT | 21 |
| | $V_H$ CDR1 | FTVSSSSIH | 22 |
| | $V_H$ CDR2 | YISSSSGYTYYADSVKG | 23 |
| | $V_H$ CDR3 | YWSYPSWWPYRGMDY | 24 |
| G9.2-17m6 | $V_L$ CDR1 | RASQSVSSAVA | 25 |
| | $V_L$ CDR2 | SASSLYS | 26 |
| | $V_L$ CDR3 | QQSSTDPIT | 27 |
| | $V_H$ CDR1 | FTVSSSSIH | 28 |
| | $V_H$ CDR2 | YISSSSGYTYYADSVKG | 29 |
| | $V_H$ CDR3 | YWSYPSWSPYRGMDY | 30 |

In some embodiments, the anti-Galectin-9 antibodies described herein bind to the same epitope as any of the exemplary antibodies described herein (e.g., G9.2-17 or G9.1-8m13) or competes against the exemplary antibody from binding to the Galectin-9 antigen. An antibody that binds the same epitope as an exemplary antibody described herein may bind to exactly the same epitope or a substantially overlapping epitope (e.g., containing less than 3 non-overlapping amino acid residue, less than 2 non-overlapping amino acid residues, or only 1 non-overlapping amino acid residue) as the exemplary antibody. Whether two antibodies compete against each other from binding to the cognate antigen can be determined by a competition assay, which is well known in the art.

In some examples, the anti-Galectin-9 antibody comprises the same $V_H$ and/or $V_L$ CDRs as an exemplary antibody described herein (e.g., G9.2-17, G9.2-17m6, or G9.1-8m13). Two antibodies having the same $V_H$ and/or $V_L$ CDRs means that their CDRs are identical when determined by the same approach (e.g., the Kabat approach or the Chothia approach as known in the art). Such anti-Galectin-9 antibodies may have the same $V_H$, the same $V_L$, or both as compared to the exemplary antibody described herein.

Two heavy chain variable regions (or two light chain variable regions) having the same CDRs means that the CDRs in the two heavy chain variable regions (or light chain variable regions) as determined by the same numbering scheme are identical. Exemplary numbering schemes for determining antibody CDRs include the "Kabat" numbering scheme (Kabat et al. (1991), 5th Ed. Public Health Service, National Institutes of Health, Bethesda, Md.), the "Chothia" numbering scheme (Al-Lazikani et al., (1997) JMB 273, 927-948), the "Contact" numbering scheme (MacCallum et al., *J. Mol. Biol.* 262:732-745 (1996)), the "IMGT" numbering scheme (Lefranc M P et al., *Dev Comp Immunol,* 2003 January; 27(1):55-77), and the "AHo" numbering scheme (Honegger A and Pluckthun A, *J Mol Biol,* 2001 Jun. 8; 309(3):657-70). As known to those skilled in the art, the CDR regions of the exemplary anti-pKa1 and anti-FXII antibodies identified herein are determined by the "Chothia" numbering scheme, which is used as an example.

In some examples, the anti-galectin antibody disclosed herein comprises a heavy chain CDR1, a heavy chain CDR2, and a heavy chain CDR3 comprising SEQ ID NOs: 16-18, respectively. Alternatively or in addition, the anti-galectin antibody comprises a light chain heavy chain CDR1, a light chain CDR2, and a light chain CDR3 comprising SEQ ID NOs: 13-15. In one specific example, the anti-galectin antibody comprises heavy chain and light chain CDRs set forth in SEQ ID NOs: 13-18.

In some examples, the anti-galectin antibody disclosed herein comprises a heavy chain CDR1, a heavy chain CDR2, and a heavy chain CDR3 comprising SEQ ID NOs: 22-24, respectively. Alternatively or in addition, the anti-galectin antibody comprises a light chain heavy chain CDR1, a light chain CDR2, and a light chain CDR3 comprising SEQ ID NOs: 19-21, respectively. In one specific example, the anti-galectin antibody comprises heavy chain and light chain CDRs set forth in SEQ ID NOs: 19-24.

In some examples, the anti-galectin antibody disclosed herein comprises a heavy chain CDR1, a heavy chain CDR2, and a heavy chain CDR3 comprising SEQ ID NOs: 28-30, respectively. Alternatively or in addition, the anti-galectin antibody comprises a light chain heavy chain CDR1, a light chain CDR2, and a light chain CDR3 comprising SEQ ID NOs: 25-27, respectively. In one specific example, the anti-galectin antibody comprises heavy chain and light chain CDRs set forth in SEQ ID NOs: 25-30.

Any of the anti-galectin 9 antibodies, e.g., those comprising the heavy chain and light chain CDRs disclosed above, may comprise a heavy chain variable region framework derived from a subclass of germline VH fragment. Such germline VH regions are well known in the art. See, e.g., the IMGT database (www.imgt.org) or at www.vbase2.org/vbstat.php. Examples include the IGHV1 subfamily (e.g., IGHV1-2, IGHV1-3, IGHV1-8, IGHV1-18, IGHV1-24, IGHV1-45, IGHV1-46, IGHV1-58, and IGHV1-69), the IGHV2 subfamily (e.g., IGHV2-5, IGHV2-26, and IGHV2-70), the IGHV3 subfamily (e.g., IGHV3-7, IGHV3-9, IGHV3-11, IGHV3-13, IGHV3-15, IGHV3-20, IGHV3-21, IGHV3-23, IGHV3-30, IGHV3-33, IGHV3-43, IGHV3-48, IGHV3-49, IGHV3-53, IGHV3-64, IGHV3-66, IGHV3-72, and IGHV3-73, IGHV3-74), the IGHV4 subfamily (e.g., IGHV4-4, IGHV4-28, IGHV4-31, IGHV4-34, IGHV4-39, IGHV4-59, IGHV4-61, and IGHV4-B), the IGHV subfamily (e.g., IGHV5-51, or IGHV6-1), and the IGHV7 subfamily (e.g., IGHV7-4-1).

Alternatively or in addition, the anti-Galectin-9 antibody may comprise a light chain variable region that contains a framework derived from a germline Vκ fragment. Examples include an IGKV1 framework (e.g., IGKV1-05, IGKV1-12, IGKV1-27, IGKV1-33, or IGKV1-39), an IGKV2 framework (e.g., IGKV2-28), an IGKV3 framework (e.g., IGKV3-11, IGKV3-15, or IGKV3-20), and an IGKV4 framework (e.g., IGKV4-1). In other instances, the anti-Galectin-9 antibody may comprise a light chain variable region that contains a framework derived from a germline Vλ fragment. Examples include an IGλ1 framework (e.g., IGλV1-36, IGλV1-40, IGλV1-44, IGλV1-47, IGλV1-51), an IGλ2 framework (e.g., IGλV2-8, IGλV2-11, IGλV2-14, IGλV2-18, IGλV2-23,), an IGλ3 framework (e.g., IGλV3-1, IGλV3-9, IGλV3-10, IGλV3-12, IGλV3-16, IGλV3-19, IGλV3-21, IGλV3-25, IGλV3-27,), an IGλ4 framework (e.g., IGλV4-3, IGλV4-60, IGλV4-69,), an IGλ5 framework (e.g., IGλV5-39, IGλV5-45,), an IGλ6 framework (e.g., IGλV6-57,), an IGλ7 framework (e.g., IGλV7-43, IGλV7-46,), an IGλ8 framework (e.g., IGλV8-61), an IGλ9 framework (e.g., IGλV9-49), or an IGλ10 framework (e.g., IGλV10-54).

Also within the scope of the present disclosure are functional variants of any of the exemplary anti-Galectin-9 antibodies as disclosed herein. Such functional variants are substantially similar to the exemplary antibody, both structurally and functionally. A functional variant comprises substantially the same $V_H$ and $V_L$ CDRs as the exemplary antibody. For example, it may comprise only up to 5 (e.g., 4, 3, 2, or 1) amino acid residue variations in the total CDR regions of the antibody and binds the same epitope of Galectin-9 with substantially similar affinity (e.g., having a $K_D$ value in the same order). Alternatively or in addition, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Such CRD1 and CRD2 binding anti-Galectin-9 antibodies are isolated and structurally characterized as described herein. The disclosure also contemplates antibodies having at least 80% identity (e.g., at least 85%, at least 90%, at least 95%, or at least 99% identity) to their variable region or CDR sequences.

For example, the anti-Galectin-9 antibody may comprise a heavy chain variable region comprising an amino acid sequence that is at least 80% (e.g., 80%, 85%, 90%, 95%, 96%, 97%, 98%, 99% and any incremental percent therein) sequence identity with the $V_H$ region of any of the exemplary anti-Galectin-9 antibodies described herein (e.g., G9.2-17. G9.2-17m6, or G9.1-8m13, the $V_H$ sequences of each of which are provided in Tables 1 and 2 above). Alternatively or in addition, the anti-Galectin-9 antibody may comprise a $V_L$ region that has at least 80% (e.g., 85%, 90%, 95%, 96%, 97%, 98%, 99% and any increment therein) sequence identity to the $V_L$ region of the exemplary anti-galectin 9 antibody.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some specific embodiments, the anti-Galectin-9 antibody comprises a $V_L$ region that has at least 80% (e.g., 85%, 90%, 95%, 96%, 97%, 98%, 99% and any increment therein) sequence identity to the $V_L$ region of G9.1-8m13. Alternatively or in addition, the anti-Galectin-9 antibody comprises a $V_H$ region that has at least 80% (e.g., 85%, 90%, 95%, 96%, 97%, 98%, 99% and any increment therein) sequence identity to the $V_H$ region of G9.1-8m13. In some embodiments, the anti-Galectin-9 antibody comprises a $V_L$ and a $V_H$ region that has at least 80% (e.g., 85%, 90%, 95%, 96%, 97%, 98%, 99% and any increment therein) sequence identity to the $V_L$ or $V_H$ region of G9.1-8m13.

In some specific embodiments, the anti-Galectin-9 antibody comprises a $V_L$ region that has at least 80% (e.g., 85%, 90%, 95%, 96%, 97%, 98%, 99% and any increment therein) sequence identity to the $V_L$ region of G9.2-17. Alternatively or in addition, the anti-Galectin-9 antibody comprises a $V_H$ region that has at least 80% (e.g., 85%, 90%, 95%, 96%, 97%, 98%, 99% and any increment therein) sequence identity to the $V_H$ region of G9.2-17. In some embodiments, the anti-Galectin-9 antibody comprises a $V_L$ and a $V_H$ region that has at least 80% (e.g., 85%, 90%, 95%, 96%, 97%, 98%, 99% and any increment therein) sequence identity to the $V_L$ or $V_H$ region of G9.2-17.

In some specific embodiments, the anti-Galectin-9 antibody comprises a $V_L$ region that has at least 80% (e.g., 85%, 90%, 95%, 96%, 97%, 98%, 99% and any increment therein) sequence identity to the $V_L$ region of G9.2-17m6. Alternatively or in addition, the anti-Galectin-9 antibody comprises a $V_H$ region that has at least 80% (e.g., 85%, 90%, 95%, 96%, 97%, 98%, 99% and any increment therein) sequence identity to the $V_H$ region of G9.2-17m6. In some embodiments, the anti-Galectin-9 antibody comprises a $V_L$ and a $V_H$ region that has at least 80% (e.g., 85%, 90%, 95%, 96%, 97%, 98%, 99% and any increment therein) sequence identity to the $V_L$ or $V_H$ region of G9.2-17m6.

In some embodiments, the heavy chain of any of the anti-Galectin-9 antibodies as described herein may further comprise a heavy chain constant region (CH) or a portion thereof (e.g., CH1, CH2, CH3, or a combination thereof). The heavy chain constant region can be of any suitable origin, e.g., human, mouse, rat, or rabbit. In one specific example, the heavy chain constant region is from a human IgG (a gamma heavy chain) of any IgG subfamily as described herein.

In some embodiments, the heavy chain constant region of the antibodies described herein may comprise a single domain (e.g., CH1, CH2, or CH3) or a combination of any of the single domains, of a constant region, which may be of any subclass of the human immunoglobulin molecule. In some examples, the heavy chain constant region is of a human IgG1 (e.g., any subclasses thereof). In other examples, the heavy chain constant region of a human IgG4 (e.g., any subclasses thereof). In some embodiments, the light chain constant region of the antibodies described herein may comprise a single domain (e.g., CL), of a constant region, for example, a kappa chain or a lamda chain.

In some embodiments, the anti-Galectin-9 antibody comprises a modified constant region. In some embodiments, the anti-Galectin-9 antibody comprise a modified constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in *Eur. J. Immunol.* (1999) 29:2613-2624; PCT 5 Application No. PCT/GB99/01441; and/or UK Patent Application No. 9809951.8. In some embodiments, the IgG4 constant region is a mutant with reduced heavy chain exchange. In some embodiments, the constant region is from a human IgG4 Fab Arm Exchange mutant S228P.

Exemplary light and heavy chain constant region sequences are listed below, including wild-type and mutated human IgG1 and human IgG4. The hIgG1 LALA sequence includes two 10 mutations, L234A and L235A (EU numbering), which suppress FcgR binding, as well as a P329G mutation (EU numbering) to abolish complement C1q binding, thus abolishing all immune effector functions. The hIgG4 Fab Arm Exchange Mutant sequence includes a mutation to suppress Fab Arm Exchange (S228P; EU numbering).

```
hIgG1 constant region
                                                          (SEQ ID NO: 31)
ASTKGPSVFPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK
```

-continued hIgG1 LALA constant region
(SEQ ID NO: 32; mutated residues in boldface and underlined)

ASTKGPSVFPLAPSSKSTSGGTAALGCLVKDYFPEPVTSWNSGALTSGVHTFPAVLQSSGLYSLSSVVT

VPSSSLGTQTYICNVNHKPSNTKVDKKVEPKSCDKTHTCPPCPAPEAAGGPSVFLFPPKPKDTLMISRTP

EVTCVVVDVSHEDPEVKFNWYVDGVEVHNAKTKPREEQYNSTYRVVSVLTVLHQDWLNGKEYKCKVSNKA

LGAPIEKTISKAKGQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

IgG4 constant region
(SEQ ID NO: 33)

ASTKGPSVFP LAPCSRSTSE STAALGCLVK DYFPEPVTVS WNSGALTSGV HTFPAVLQSS

GLYSLSSVVT VPSSSLGTKT YTCNVDHKPS NTKVDKRVES KYGPPCPSCP APEFLGGPSV

FLFPPKPKDT LMISRTPEVT CVVVDVSQED PEVQFNWYVD GVEVHNAKTK PREEQFNSTY

RVVSVLTVLH QDWLNGKEYK CKVSNKGLPS SIEKTISKAK GQPREPQVYT LPPSQEEMTK

NQVSLTCLVK GFYPSDIAVE WESNGQPENN YKTTPPVLDS DGSFFLYSRL TVDKSRWQEG

NVFSCSVMHE ALHNHYTQKS LSLSLGK

IgG4 constant region Mutant 1
(SEQ ID NO: 34; mutated residues in boldface and underlined)

ASTKGPSVFPLAPCSRSTSESTAALGCLVKDYFPEPVTVSWNSGALTSGVHTFPAVLQSSGLYSLSSVVT

VPSSSLGTKTYTCNVDHKPSNTKVDKRVESKYGPPCPSCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSPGK hIgG4 Fab Arm Exchange mut constant region 1
(SEQ ID NO: 35; mutated residues in boldface and underlined)

ASTKGPSVFPLAPCSRSTSESTAALGCLVKDYFPEPVTVSWNSGALTSGVHTFPAVLQSSGLYSLSSVVT

VPSSSLGTKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSPGK hIgG4 Fab Arm Exchange mut constant region 2
(SEQ ID NO: 36; mutated residues in boldface and underlined)

ASTKGPSVFPLAPCSRSTSESTAALGCLVKDYFPEPVTVSWNSGALTSGVHTFPAVLQSSGLYSLSSVVT

VPSSSLGTKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

LC constant region
(SEQ ID NO: 37)

TVAAPSVFIFPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

Any of the anti-galectin-9 antibodies disclosed herein may comprise any of the heavy chain constant regions set forth in SEQ ID NOs: 31-36 linked to the $V_H$ region as disclosed herein. In specific examples, the anti-galectin-9 antibody disclosed herein comprises the same heavy chain and light chain CDRs (i.e., the same HC CDR1, HC CDR2, HC CDR3, LC CDR1, LC CDR2, and LC CDR3) as clone G9.2-17 (e.g., comprises the same $V_H$ and $V_L$ chains as G9.2-17) and a heavy chain constant region comprising SEQ ID NO:36. In other specific examples, the anti-galectin-9 antibody disclosed herein comprises the same heavy chain and light chain (i.e., the same HC CDR1, HC CDR2, HC CDR3, LC CDR1, LC CDR2, and LC CDR3) as clone G9.2-17mut6 (e.g., comprises the same $V_H$ and $V_L$ chains as G9.2-17mut6) and a heavy chain constant region comprising SEQ ID NO:36. In yet other specific examples, In specific examples, the anti-galectin-9 antibody disclosed herein comprises the same heavy chain and light chain (i.e., the same HC CDR1, HC CDR2, HC CDR3, LC CDR1, LC CDR2, and LC CDR3) as clone G9.1-8m13 (e.g., comprises the same $V_H$ and $V_L$ chains as G9.1-8m13) and a heavy chain constant region comprising SEQ ID NO:36.

Alternatively or in addition, any of the anti-galectin-9 antibodies disclosed herein may comprise the light chain constant region set forth in SEQ ID NO: 37 linked to the $V_L$ region as disclosed herein.

Specific examples of full length exemplary anti-galectin 9 antibodies are provided below:

G9.2-17 hIgG1 Heavy Chain (SEQ ID NO: 38)

EVQLVESGGGLVQPGGSLRLSCAASGFTVSSSSIHWVRQAPGKGLEWVAYISSSSGYTYYADSVKGRFTI

SADTSKNTAYLQMNSLRAEDTAVYYCARYWSYPSWWPYRGMDYWGQGTLVTVSSASTKGPSVFPLAPSSK

STSGGTAALGCLVKDYFPEPVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMISRTPEVICVVVDVSHEDPEV

KFNWYVDGVEVHNAKTKPREEQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKTTPPVLDSDGSFFLYSKLTVD

KSRWQQGNVFSCSVMHEALHNHYTQKSLSLSPGK*

G9.2-17 hIgG1 LALA Heavy Chain (SEQ ID NO: 39)

EVQLVESGGGLVQPGGSLRLSCAASGFTVSSSSIHWVRQAPGKGLEWVAYISSSSGYTYYADSVKGRFTI

SADTSKNTAYLQMNSLRAEDTAVYYCARYWSYPSWWPYRGMDYWGQGTLVTVSSASTKGPSVFPLAPSSK

STSGGTAALGCLVKDYFPEPVTVSWNSGALTSGVHTFPAVLQSSGLYSLSSVVTVPSSSLGTQTYICNVN

HKPSNTKVDKKVEPKSCDKTHTCPPCPAPEAAGGPSVFLFPPKPKDTLMISRTPEVICVVVDVSHEDPEV

KFNWYVDGVEVHNAKTKPREEQYNSTYRVVSVLTVLHQDWLNGKEYKCKVSNKALGAPIEKTISKAKGQP

REPQVYTLPPSREEMTKNQVSLTCLVKGFYPSDIAVEWESNGQPENNYKTTPPVLDSDGSFFLYSKLTVD

KSRWQQGNVFSCSVMHEALHNHYTQKSLSLSPGK*

G9.2-17 hIgG4 Heavy Chain (SEQ ID NO: 40)

EVQLVESGGGLVQPGGSLRLSCAASGFTVSSSSIHWVRQAPGKGLEWVAYISSSSGYTYYADSVKGRFTI

SADTSKNTAYLQMNSLRAEDTAVYYCARYWSYPSWWPYRGMDYWGQGTLVTVSSASTKGPSVFPLAPCSR

STSESTAALGCLVKDYFPEPVTVSWNSGALTSGVHTFPAVLQSSGLYSLSSVVTVPSSSLGTKTYTCNVD

HKPSNTKVDKRVESKYGPPCPSCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPPVLDSDGSFFLYSRLTVDKSR

WQEGNVFSCSVMHEALHNHYTQKSLSLSPGK*

G9.2-17 hIgG4 Fab Arm Exchange mut Heavy Chain (SEQ ID NO: 41)

EVQLVESGGGLVQPGGSLRLSCAASGFTVSSSSIHWVRQAPGKGLEWVAYISSSSGYTYYADSVKGRFTI

SADTSKNTAYLQMNSLRAEDTAVYYCARYWSYPSWWPYRGMDYWGQGTLVTVSSASTKGPSVFPLAPCSR

STSESTAALGCLVKDYFPEPVTVSWNSGALTSGVHTFPAVLQSSGLYSLSSVVTVPSSSLGTKTYTCNVD

HKPSNTKVDKRVESKYGPPCPPCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPPVLDSDGSFFLYSRLTVDKSR

WQEGNVFSCSVMHEALHNHYTQKSLSLSPGK*

G9.2-17 hIgG4 Fab Arm Exchange mut Heavy Chain (SEQ ID NO: 42)

EVQLVESGGGLVQPGGSLRLSCAASGFTVSSSSIHWVRQAPGKGLEWVAYISSSSGYTYYADSVKGRFTI

SADTSKNTAYLQMNSLRAEDTAVYYCARYWSYPSWWPYRGMDYWGQGTLVTVSSASTKGPSVFPLAPCSR

STSESTAALGCLVKDYFPEPVTVSWNSGALTSGVHTFPAVLQSSGLYSLSSVVTVPSSSLGTKTYTCNVD

HKPSNTKVDKRVESKYGPPCPPCPAPEFLGGPSVFLFPPKPKDTLMISRTPEVTCVVVDVSQEDPEVQFN

-continued

WYVDGVEVHNAKTKPREEQFNSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPPVLDSDGSFFLYSRLTVDKSR

WQEGNVFSCSVMHEALHNHYTQKSLSLSLGK

G9.1-8m13 hIgG1 Heavy Chain (SEQ ID NO: 61)

EVQLVESGGGLVQPGGSLRLSCAASGFTVSSSSIHWVRQAPGKGLEWVAYIYPYSSSSSYADSVKGRFTI

SADTSKNTAYLQMNSLRAEDTAVYYCARYSTYSSKWVWGMDYWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISRIPEVTCVVVDVSHEDPEVK

FNWYVDGVEVHNAKTKPREEQYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTTPPVLDSDGSFFLYSKLTVDK

SRWQQGNVFSCSVMHEALHNHYTQKSLSLSPGK*

G9.1-8m13 hIgG1 LALA Heavy Chain (SEQ ID NO: 43)

EVQLVESGGGLVQPGGSLRLSCAASGFTVSSSSIHWVRQAPGKGLEWVAYIYPYSSSSSYADSVKGRFTI

SADTSKNTAYLQMNSLRAEDTAVYYCARYSTYSSKWVWGMDYWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICNVNH

KPSNTKVDKKVEPKSCDKTHTCPPCPAPEAAGGPSVFLFPPKPKDTLMISRIPEVTCVVVDVSHEDPEVK

FNWYVDGVEVHNAKTKPREEQYNSTYRVVSVLTVLHQDWLNGKEYKCKVSNKALGAPIEKTISKAKGQPR

EPQVYTLPPSREEMTKNQVSLTCLVKGFYPSDIAVEWESNGQPENNYKTTPPVLDSDGSFFLYSKLTVDK

SRWQQGNVFSCSVMHEALHNHYTQKSLSLSPGK*

G9.1-8m13 hIgG4 Heavy Chain (SEQ ID NO: 44)

EVQLVESGGGLVQPGGSLRLSCAASGFTVSSSSIHWVRQAPGKGLEWVAYIYPYSSSSSYADSVKGRFTI

SADTSKNTAYLQMNSLRAEDTAVYYCARYSTYSSKWVWGMDYWGQGTLVTVSSASTKGPSVFPLAPCSRS

TSESTAALGCLVKDYFPEPVTVSWNSGALTSGVHTFPAVLQSSGLYSLSSVVTVPSSSLGTKTYTCNVDH

KPSNTKVDKRVESKYGPPCPSCPAPEFLGGPSVFLFPPKPKDTLMISRTPEVICVVVDVSQEDPEVQFNW

YVDGVEVHNAKTKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFLYSRLTVDKSRW

QEGNVFSCSVMHEALHNHYTQKSLSLSPGK*

G9.1-8m13 hIgG4 Fab Arm Exchange mut Heavy Chain (SEQ ID NO: 45)

EVQLVESGGGLVQPGGSLRLSCAASGFTVSSSSIHWVRQAPGKGLEWVAYIYPYSSSSSYADSVKGRFTI

SADTSKNTAYLQMNSLRAEDTAVYYCARYSTYSSKWVWGMDYWGQGTLVTVSSASTKGPSVFPLAPCSRS

TSESTAALGCLVKDYFPEPVTVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDILMISRTPEVICVVVDVSQEDPEVQFNW

YVDGVEVHNAKTKPREEQFNSTYRVVSVLTVLHQDWLNGKEYKCKVSNKGLPSSIEKTISKAKGQPREPQ

VYTLPPSQEEMTKNQVSLICLVKGFYPSDIAVEWESNGQPENNYKTIPPVLDSDGSFFLYSRLTVDKSRW

QEGNVFSCSVMHEALHNHYTQKSLSLSPGK*

G9.1-8m13 hIgG4 Fab Arm Exchange mut Heavy Chain (SEQ ID NO: 46)

EVQLVESGGGLVQPGGSLRLSCAASGFTVSSSSIHWVRQAPGKGLEWVAYIYPYSSSSSYADSVKGRFTI

SADTSKNTAYLQMNSLRAEDTAVYYCARYSTYSSKWVWGMDYWGQGTLVTVSSASTKGPSVFPLAPCSRS

TSESTAALGCLVKDYFPEPVTVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDILMISRTPEVICVVVDVSQEDPEVQFNW

-continued

YVDGVEVHNAKTKPREEQFNSTYRVVSVLTVLHQDWLNGKEYKCKVSNKGLPSSIEKTISKAKGQPREPQ

VYTLPPSQEEMTKNQVSLICLVKGFYPSDIAVEWESNGQPENNYKTIPPVLDSDGSFFLYSRLTVDKSRW

QEGNVFSCSVMHEALHNHYTQKSLSLSLGK

An anti-galectin 9 antibody comprising a heavy chain with any of the IgG1 or IgG4 constant regions may be paired with the following light chain G9.2-17 Light Chain (SEQ ID NO: 47)

DIQMTQSPSSLSASVGDRVTITCRASQSVSSAVAWYQQKPGKAPKLLIYSA

SSLYSGVPSRFSGSRSGTDFTLTISSLQPEDFATYYCQQSSTDPITFGQGT

KVEIKRTVAAPSVFIFPPSDEQLKSGTASVVCLLNNFYPREAKVONKVDNA

LQSGNSQESVTEQDSKDSTYSLSSILTLSKADYEKHKVYACEVTHQGLSSP

VTKSENRGEC*

G9.1-8m13 Light chain (SEQ ID NO: 62

DIQMTQSPSSLSASVGDRVTITCRASQSVSSAVAWYQQKPGKAPKLLIYSA

SSLYSGVPSRFSGSRSGTDFTLTISSLQPEDFATYYCQQSYYDSNPITFGQ

GTKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLS

SPVTKSFNRGEC

In any of the above sequences, the regions in boldface are the $V_H$ and $V_L$ regions. In some instances, An IL2 signal sequence (MYRMQLLSCIALSLALVTNS; SEQ ID NO: 48) can be located at the N-terminus of one or both variable regions. It is used in expression vectors, which is cleaved during secretion and thus not in the mature antibody molecule. The mature protein (after secretion) starts with "EVQ" for the heavy chain and "DIM" for the light chain.

In some embodiments, the anti-Galectin-9 antibody comprises a VL CDR1 having the sequence of SEQ ID NO: 19. In some embodiments, the anti-Galectin-9 antibody comprises a VL CDR2 having the sequence of SEQ ID NO: 20. In some embodiments, the anti-Galectin-9 antibody comprises a VL CDR3 having the sequence of SEQ ID NO: 21. In some embodiments, the anti-Galectin-9 antibody comprises a VL CDR1 having the sequence of SEQ ID NO: 19, a VL CDR2 having the sequence of SEQ ID NO: 20, and a VL CDR3 having the sequence of SEQ ID NO: 21. In some embodiments, the anti-Galectin-9 antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 19, 20, and 21, respectively.

In some embodiments, the anti-Galectin-9 antibody comprises a VH CDR1 having the sequence of SEQ ID NO: 22. In some embodiments, the anti-Galectin-9 antibody comprises a VH CDR2 having the sequence of SEQ ID NO: 23. In some embodiments, the anti-Galectin-9 antibody comprises a VH CDR3 having the sequence of SEQ ID NO: 24. In some embodiments, the anti-Galectin-9 antibody comprises a VH CDR1 having a sequence set forth in SEQ ID NO: 22, a VH CDR2 having the sequence of SEQ ID NO: 23, and a VH CDR3 having the sequence of SEQ ID NO:24. Alternatively or in addition, the anti-Galectin-9 antibody comprises a VL CDR1 having the sequence of SEQ ID NO: 19, a VL CDR2 having the sequence of SEQ ID NO: 20, and a VL CDR3 having the sequence of SEQ ID NO: 21. In some embodiments, the anti-Galectin-9 antibody comprises a heavy chain variable domain ($V_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NO: 22 (CDR1), 23 (CDR2), and 24 (CDR3), respectively. Alternatively or in addition, the anti-Galectin-9 antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 19, 20, and 21, respectively.

In some embodiments, the anti-Galectin-9 antibody comprises a VH CDR1 having the sequence of SEQ ID NO: 22, a VH CDR2 having the sequence of SEQ ID NO: 23, and a VH CDR3 having the sequence of SEQ ID NO: 24, and further comprises a VL CDR1 having the sequence of SEQ ID NO: 19, a VL CDR2 having the sequence of SEQ ID NO: 20, and a VL CDR3 having the sequence of SEQ ID NO: 21. In some embodiments, the anti-Galectin-9 antibody comprises a light chain variable domain ($V_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOs: 22, 23, and 24, respectively, and further comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 19, 20, and 21, respectively.

In some embodiments, the anti-Galectin-9 antibody comprises a VH region having the sequence of SEQ ID NO: 10. In some embodiments, the anti-Galectin-9 antibody comprises a VL region having the sequence of SEQ ID NO: 9. In some embodiments, the anti-Galectin-9 antibody comprises a VH region having the sequence of SEQ ID NO: 10 and a VL region having the sequence of SEQ ID NO: 9.

In some embodiments, the anti-Galectin-9 antibody has a $V_H$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 10. In some embodiments, the anti-Galectin-9 antibody has a $V_L$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 9. In some embodiments, the anti-Galectin-9 antibody has a $V_H$ sequence comprising SEQ ID NO: 10. In some embodiments, the anti-Galectin-9 antibody has a $V_L$ sequence comprising SEQ ID NO: 9. In some embodiments, the isolated antibody has a $V_H$ sequence consisting essentially of or consisting of SEQ ID NO: 10. In some embodiments, the isolated antibody has a $V_L$ sequence consisting essentially of or consisting of SEQ ID NO: 9.

In some embodiments, the anti-Galectin-9 antibody has a $V_H$ sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 10 and has a $V_L$ sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 9. In some embodiments, the isolated antibody has a $V_H$ sequence comprising SEQ ID NO: 10 and a $V_L$ sequence comprising SEQ ID NO: 9. In some embodiments, the isolated antibody has a $V_H$ sequence consisting essentially of SEQ ID NO: 10 and a $V_L$ sequence consisting essentially of SEQ ID NO: 9. In some embodiments, the isolated antibody has a $V_H$ sequence consisting of SEQ ID NO: 10 and a $V_L$ sequence consisting of SEQ ID NO: 9.

In some embodiments, the anti-Galectin-9 antibody has a Light Chain (LC) constant region sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 37. In some embodiments, the anti-Galectin-9 antibody has a LC constant region sequence comprising SEQ ID NO: 37. In some embodiments, the isolated antibody has a LC constant region sequence consisting essentially of or consisting of SEQ ID NO: 37.

In some embodiments, the anti-Galectin-9 antibody has a heavy chain (HC) constant region sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 35. In some embodiments, the anti-Galectin-9 antibody has a HC constant region sequence comprising SEQ ID NO: 35. In some embodiments, the isolated antibody has a HC constant region sequence consisting essentially of or consisting of SEQ ID NO: 35.

In some embodiments, the anti-Galectin-9 antibody has a HC constant region sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 35 and has a LC constant region sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 37. In some embodiments, the isolated antibody has a HC constant region sequence comprising SEQ ID NO: 35 and a LC constant region sequence comprising SEQ ID NO: 37. In some embodiments, the isolated antibody has a HC constant region sequence consisting essentially of SEQ ID NO: 35 and a LC constant region sequence consisting essentially of SEQ ID NO: 37. In some embodiments, the isolated antibody has a HC constant region sequence consisting of SEQ ID NO: 35 and a LC constant region sequence consisting of SEQ ID NO: 37.

In some embodiments, the anti-Galectin-9 antibody has a heavy chain (HC) constant region sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 36. In some embodiments, the anti-Galectin-9 antibody has a HC constant region sequence comprising SEQ ID NO: 36. In some embodiments, the isolated antibody has a HC constant region sequence consisting essentially of or consisting of SEQ ID NO: 36.

In some embodiments, the anti-Galectin-9 antibody has a HC constant region sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 36 and has a LC constant region sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 37. In some embodiments, the isolated antibody has a HC constant region sequence comprising SEQ ID NO: 36 and a LC constant region sequence comprising SEQ ID NO: 37. In some embodiments, the isolated antibody has a HC constant region sequence consisting essentially of SEQ ID NO: 36 and a LC constant region sequence consisting essentially of SEQ ID NO: 37. In some embodiments, the isolated antibody has a HC constant region sequence consisting of SEQ ID NO: 36 and a LC constant region sequence consisting of SEQ ID NO: 37.

In some embodiments, the anti-Galectin-9 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 47. In some embodiments, the anti-Galectin-9 antibody has a light chain sequence comprising SEQ ID NO: 47. In some embodiments, the isolated antibody has a light chain sequence consisting essentially of SEQ ID NO: 47 or consisting of SEQ ID NO: 47.

In some embodiments, the anti-Galectin-9 antibody has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 41. In some embodiments, the anti-Galectin-9 antibody has a heavy chain sequence comprising SEQ ID NO: 41. In some embodiments, the isolated antibody has a heavy chain sequence consisting essentially of SEQ ID NO: 41 or consisting of SEQ ID NO: 41.

In some embodiments, the anti-Galectin-9 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 47 and has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 41. In some embodiments, the isolated antibody has a light chain sequence comprising SEQ ID NO: 47 and a heavy chain sequence comprising SEQ ID NO: 41. In some embodiments, the isolated antibody has a light chain sequence consisting essentially of SEQ ID NO: 47 and a heavy chain sequence consisting essentially of SEQ ID NO: 41. In some embodiments, the isolated antibody has a light chain sequence consisting of SEQ ID NO: 47 and a heavy chain sequence consisting of SEQ ID NO: 41.

In some embodiments, the anti-Galectin-9 antibody has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 42. In some embodiments, the anti-Galectin-9 antibody has a heavy chain sequence comprising SEQ ID NO: 42. In some embodiments, the isolated antibody has a heavy chain sequence consisting essentially of SEQ ID NO: 42 or consisting of SEQ ID NO: 42.

In some embodiments, the anti-Galectin-9 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 47 and has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 42. In some embodiments, the isolated antibody has a light chain sequence comprising SEQ ID NO: 47 and a heavy chain sequence comprising SEQ ID NO: 42. In some embodiments, the isolated antibody has a light chain sequence consisting essentially of SEQ ID NO: 47 and a heavy chain sequence consisting essentially of SEQ ID NO: 42. In some embodiments, the isolated antibody has a light chain sequence consisting of SEQ ID NO: 47 and a heavy chain sequence consisting of SEQ ID NO: 42.

In another aspect, the present disclosure provides an isolated nucleic acid or set of nucleic acids which encode or collectively encode any of the anti-Galectin-9 antibodies disclosed herein. In some instances, the heavy chain and light chain of the antibody are encoded by two separate nucleic acid molecules (a set of nucleic acids). In other instances, the heavy chain and light chain of the antibody are encoded by one nucleic acid molecule, which may be in multicistronic format, or under the control of distinct promoters. Accordingly, in one aspect the disclosure provides an isolated nucleic acid molecule comprising one or more nucleic acid sequence(s) encoding a heavy chain variable region (VH) and/or a light chain variable region (VL) of an anti-Galectin-9 antibody described herein. In some embodiments, the nucleic acid molecule comprises one or more nucleic acid sequence(s) encoding a heavy chain variable region (VH) of an anti-Galectin-9 antibody described herein. Alternatively or in addition, in some embodiments, the nucleic acid molecule comprises one or more nucleic acid sequence(s) encoding a Light chain variable region (VL) of an anti-Galectin-9 antibody described herein. In one specific embodiment, the nucleic acid molecule comprises one or more nucleic acid sequences encoding a VH and/or VL (or a heavy chain and/or light chain) of an antibody comprising a heavy chain complementarity determining region 1 (CDR1) set forth as SEQ ID NO: 22, a heavy chain complementary determining region 2 (CDR2) set forth as SEQ ID NO: 23, and a heavy chain complementary determining region 3 (CDR3) set forth as SEQ ID NO: 24 and/or comprises a light chain complementarity determining region 1 (CDR1) set forth as SEQ ID NO: 19, a light chain complementary determining region 2 (CDR2) set forth as SEQ ID NO: 20, and a light chain complementary determining region 3 (CDR3) set forth as SEQ ID NO: 21. Accordingly, in some embodiments, the nucleic acid molecule comprises one or more nucleic acid sequence(s) encoding a VH and/or VL (or a heavy chain and/or light chain) of an antibody comprising a VH set forth as SEQ ID NO: 10 and/or a VL set forth as SEQ ID NO: 9. Accordingly, in some embodiments, the nucleic acid molecule comprises one or more nucleic acid sequence(s) encoding a HC constant region and/or LC constant region (or a heavy chain and/or light chain) of an antibody comprising a HC constant region set forth as SEQ ID NO: 34 and/or a HL constant region set forth as SEQ ID NO: 37.

Accordingly, in some embodiments, the nucleic acid molecule comprises one or more nucleic acid sequence(s) encoding a HC constant region and/or LC constant region (or a heavy chain and/or light chain) of an antibody comprising a HC constant region set forth as SEQ ID NO: 35 and/or a HL constant region set forth as SEQ ID NO: 37.

Accordingly, in some embodiments, the nucleic acid molecule comprises one or more nucleic acid sequence(s) encoding a heavy chain and/or light chain of an antibody comprising a HC set forth as SEQ ID NO: 41 and/or a LC set forth as SEQ ID NO: 47.

Accordingly, in some embodiments, the nucleic acid molecule comprises one or more nucleic acid sequence(s) encoding a a heavy chain and/or light chain of an antibody comprising a HC set forth as SEQ ID NO: 42 and/or a LC set forth as SEQ ID NO: 47.

In one example, the one or more nucleic acid sequences encode a VH and/or VL (or a heavy chain and/or light chain) of G9.2-17.

Preparation of Anti-Galectin-9 Antibodies

Antibodies capable of binding Galectin-9 as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., Galectin-9 or a CRD thereof) are made by conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495-497 or as modified by Buck, D. W., et al., *In Vitro,* 18:377-381 (1982). Available myeloma lines, including, but not limited to, X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-Galectin-9 monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the Galectin-9 activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N═C═NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of Galectin-9. It will be apparent to one of skill in the art that one or more polynucleotide changes can be made to the antibody and still maintain its binding specificity to the target antigen.

In other embodiments, fully human antibodies are obtained using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In other embodiments, antibodies are made recombinantly by phage display or yeast technology. See, for example, U.S. Pat. Nos. 5,565,332; 5,580,717; 5,733,743; and 6,265,150; and Winter et al., (1994) *Annu. Rev. Immunol.* 12:433-455. In alternate embodiments, phage display technology (McCafferty et al., (1990) *Nature* 348: 552-553) is used to produce human antibodies and antibody fragments in vitro, from immunoglobulin variable (V) domain gene repertoires from unimmunized donors.

In alternate embodiments, antibodies capable of binding to the target antigens as described herein are isolated from a suitable antibody library. Antibody libraries, which contain a plurality of antibody components, can be used to identify antibodies that bind to a specific target antigen (e.g., the CRD1 or CRD2 of Galectin-9 in this case) following routine selection processes as known in the art. In the selection process, an antibody library can be probed with the target antigen or a fragment thereof and members of the library that are capable of binding to the target antigen can be isolated, typically by retention on a support. Such screening process may be performed by multiple rounds (e.g., including both positive and negative selections) to enrich the pool of antibodies capable of binding to the target antigen. Individual clones of the enriched pool can then be isolated and further characterized to identify those having desired binding activity and biological activity. Sequences of the heavy chain and light chain variable domains can also be determined via conventional methodology. There are a number of routine methods known in the art to identify and isolate antibodies capable of binding to the target antigens described herein, including phage display, yeast display, ribosomal display, or mammalian display technology.

As an example, phage displays typically use a covalent linkage to bind the protein (e.g., antibody) component to a bacteriophage coat protein. The linkage results from translation of a nucleic acid encoding the antibody component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8 and Hoet et al. (2005) *Nat Biotechnol.* 23(3)344-8. Additional suitable methods are described in Miller et al., *PloS One,* 2012, 7, e43746; Fellouse et al., *J Mol Biol,* 2007, 373, 924-940. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be selected, and then the nucleic acid may be isolated and sequenced.

Other display formats include cell-based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000)*Methods Enzymol.* 328:404-30; and Schaffitzel et al. (1999) *J Immunol Methods.* 231(1-2):119-35), and *E. coli* periplasmic display (*J Immunol Methods.* 2005 Nov. 22; PMID: 16337958).

After display library members are isolated for binding to the target antigen, each isolated library member can be also tested for its ability to bind to a non-target molecule to evaluate its binding specificity. Examples of non-target molecules include streptavidin on magnetic beads, blocking agents such as bovine serum albumin, non-fat bovine milk, soy protein, any capturing or target immobilizing monoclonal antibody, or non-transfected cells which do not express the target. A high-throughput ELISA screen can be used to obtain the data, for example. The ELISA screen can also be used to obtain quantitative data for binding of each library member to the target as well as for cross species reactivity to related targets or subunits of the target antigen and also under different condition such as pH 6 or pH 7.5. The non-target and target binding data are compared (e.g., using a computer and software) to identify library members that specifically bind to the target.

After selecting candidate library members that bind to a target, each candidate library member can be further analyzed, e.g., to further characterize its binding properties for the target, e.g., Galectin-9. Each candidate library member can be subjected to one or more secondary screening assays. The assay can be for a binding property, a catalytic property, an inhibitory property, a physiological property (e.g., cytotoxicity, renal clearance, or immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties are described below.

Binding proteins can also be evaluated using an ELISA assay. For example, each protein is contacted to a microtitre plate whose bottom surface has been coated with the target, e.g., a limiting amount of the target. The plate is washed with buffer to remove non-specifically bound polypeptides. Then the amount of the binding protein bound to the target on the plate is determined by probing the plate with an antibody that can recognize the binding protein, e.g., a tag or constant portion of the binding protein. The antibody is linked to a detection system (e.g., an enzyme such as alkaline phosphatase or horse radish peroxidase (HRP) which produces a colorimetric product when appropriate substrates are provided).

Alternatively, the ability of a binding protein described herein to bind a target antigen can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means, e.g., using a fluorimeter. By titrating the amount of the first or second binding molecule, a binding curve can be generated to estimate the equilibrium binding constant.

Surface plasmon resonance (SPR) can be used to analyze the interaction of a binding protein and a target antigen. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of SPR). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, *Anal. Chem.* 63:2338-2345; Szabo et al., 1995, *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_D$), and kinetic parameters, including $K_{on}$ and $K_{off}$, for the binding of a binding protein to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

As a further example, cellular assays may be used. Binding proteins can be screened for ability to bind to cells which transiently or stably express and display the target of interest on the cell surface. For example, Galectin-9 binding proteins can be fluorescently labeled and binding to Galectin-9 in the presence or absence of antagonistic antibody can be detected by a change in fluorescence intensity using flow cytometry e.g., a FACS machine.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Methods for constructing humanized antibodies are also well known in the art. See, e.g., Queen et al., *Proc. Natl. Acad. Sci. USA,* 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to Galectin-9 can be identified from the library following routine procedures. Positive clones can be subjected to further screening to identify those that inhibit Galectin-9 activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence, to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the Galectin-9 polypeptide have been replaced (swapped) with sequences from a closely related, but antigenically distinct protein (such as another member of the β-galactoside-binding soluble lectin family). By assessing binding of the antibody to the mutant Galectin-9, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

In some examples, an anti-Galectin-9 antibody is prepared by recombinant technology as exemplified below.

Nucleic acids encoding the heavy and light chain of an anti-Galectin-9 antibody as described herein can be cloned into one expression vector, each nucleotide sequence being in operable linkage to a suitable promoter. In one example, each of the nucleotide sequences encoding the heavy chain and light chain is in operable linkage to a distinct promoter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., *Cell,* 49:603-612 (1987)], those using the tetracycline repressor (tetR) [Gossen, M., and Bujard, H., *Proc. Natl. Acad. Sci. USA* 89:5547-5551 (1992); Yao, F. et al., *Human Gene Therapy,* 9:1939-1950 (1998); Shockelt, P., et al., *Proc. Natl. Acad. Sci. USA,* 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters (M. Brown et al., *Cell,* 49:603-612 (1987); Gossen and Bujard (1992); M. Gossen et al., *Natl. Acad. Sci. USA,* 89:5547-5551 (1992)) combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., *Human Gene Therapy,* 10(16):1392-1399 (2003)). One particular advantage of this tetracycline inducible switch is that it does not require the use of a tetracycline repressor-mammalian cells transactivator or repressor fusion protein, which in some instances can be toxic to cells (Gossen et al., *Natl. Acad. Sci. USA,* 89:5547-5551 (1992); Shockett et al., *Proc. Natl. Acad. Sci. USA,* 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-Galectin-9 antibody, as also described herein. The recombinant expression vector can be introduced into a suitable host cell (e.g., a dhfr− CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-Galectin-9 antibody and the other encoding the light chain of the anti-Galectin-9 antibody. Both of the two recombinant expression vectors can be introduced into a suitable host cell (e.g., dhfr− CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-Galectin-9 antibody as described herein, vectors (e.g., expression vectors) containing such; and host cells comprising the vectors are within the scope of the present disclosure.

Anti-Galectin-9 antibodies thus prepared can be can be characterized using methods known in the art, whereby reduction, amelioration, or neutralization of Galectin-9 biological activity is detected and/or measured. For example, an ELISA-type assay may be suitable for qualitative or quantitative measurement of Galectin-9 inhibition of Dectin-1 or TIM-3 signaling.

Once the antibody is produced certain characteristics important for a clinical candidate are evaluated. Such characteristics include, but are not limited to, propensity to aggregate, purity, thermal and chemical stability, solubility, serum stability, and presence of non-specific protein interactions. Stability studies are conducted to ensure that the antibody can be stored and can be safely used. Stability is assessed using methods known in the art (Le Basle et al., *J Pharm Sci.* 2019 Aug. 26). Chemical stability can be assessed by ion-exchange chromatography or capillary electrophoresis, e.g., including methods described herein. Biological stability can be assessed immunological or cytotoxic assays, including but not limited to those described herein.

Propensity to aggregate can negatively impact manufacturing, stability, shelf life, solubility, and administration. Aggregation is assessed using methods known in the art, including but not limited to size exclusion chromatography, which can assess the levels of IgG aggregates and IgG monomeric forms, of the antibody in a sample. Thermal instability is one potential cause of aggregation. In some embodiments, the anti-Galectin-9 antibody described herein, e.g., G9.2-17, is greater than about 90% monomeric under all conditions tested. In some embodiments, the anti-Galectin-9 antibody described herein, e.g., G9.2-17, is greater than about 95% monomeric under all conditions tested. In some embodiments, the anti-Galectin-9 antibody described herein, e.g., G9.2-17, is greater than about 98% monomeric under all conditions tested. In some embodiments, the anti-Galectin-9 antibody described herein, e.g., G9.2-17, is greater than about 99% monomeric under all conditions tested. In one embodiment, the Fab Tm is about 65° C.

Appropriate concentration is necessary to allow administration to the patient of the relevant dose of the therapeutic antibody in a suitable volume. In some embodiments, the antibody is formulated to a concentration of any of about 1-5 mg/ml, 5-10 mg/ml, 10-15 mg/ml, 15-20 mg/ml, 20-25 mg/ml, 25-30 mg/ml, 30-35 mg/ml, or 35-40 mg/ml. In some embodiments, the antibody is formulated to a concentration of about 30 mg/ml (for example 30.42 mg/ml). In some embodiments, the antibody is formulated to a concentration of 30.00 mg/ml. In some embodiments, the antibody is lyophilized. In some embodiments, the antibody is diluted in a suitable solution to a suitable concentration prior to administration.

The bioactivity of an anti-Galectin-9 antibody can verified by incubating a candidate antibody with Dectin-1 and Galectin-9, and monitoring any one or more of the following characteristics: (a) binding between Dectin-1 and Galectin-9 and inhibition of the signaling transduction mediated by the binding; (b) preventing, ameliorating, or treating any aspect of a solid tumor; (c) blocking or decreasing Dectin-1 activation; (d) inhibiting (reducing) synthesis, production or release of Galectin-9. Alternatively, TIM-3 can be used to verify the bioactivity of an anti-Galectin-9 antibody using the protocol described above. Alternatively, CD206 can be used to verify the bioactivity of an anti-Galectin-9 antibody using the protocol described above.

Additional assays to determine bioactivity of an anti-Galectin-9 antibody include measurement of CD8+ and CD4+(conventional) T-cell activation (in an in vitro or in vivo assay, e.g., by measuring inflammatory cytokine levels, e.g., IFNgamma, TNFalpha, CD44, ICOS granzymeB, Perforin, TL2 (upregulation); CD26L and IL-10 (downregulation)); measurement of reprogramming of macrophages (in vitro or in vivo), e.g., from the M2 to the M1 phenotype (e.g., increased MHCII, reduced CD206, increased TNF-alpha and iNOS). Alternatively, levels of ADCC can be assessed, e.g., in an in vitro assay, as described herein.

Methods of Modulating Immune Responses

The present disclosure provides pharmaceutical compositions comprising at least one anti-Galectin-9 antibody described herein (e.g., full-length or an antigen binding fragment thereof) and uses of such for modulating (e.g., increasing) an immune response. for example, increasing production of interferon γ, TNFalpha, or a combination thereof, increasing expression of CD44 in $CD4^+$ cells and/or $CD8^+$ cells, and/or enhancing the level of $CD8^+$ cells. In some embodiments, the overall immune response is increased.

The anti-galectin 9 antibody may be used in combination with a checkpoint inhibitor such as an anti-PD1 or anti-PD-L1 antibody. In some embodiments, the method for increasing immune responses as provided herein may comprise administering to a subject in need thereof (e.g., a human patient disclosed herein) an effective amount of an anti-Galectin-9 antibody (anti-Gal9 antibody, for example, any of the exemplary antibodies disclosed in Table 1 and/or Table 2) that binds a Galectin-9 polypeptide, wherein the subject is on a treatment comprising a checkpoint inhibitor such as an anti-PD1 antibody. In other embodiments, the method for increasing immune responses as provided herein may comprise (i) administering to a subject in need thereof (e.g., a human patient as those described herein) an effective amount of an anti-Galectin-9 antibody (anti-Gal9 antibody, for example, any of the exemplary antibodies disclosed in Table 1 and/or Table 2) that binds a Galectin-9 polypeptide; and (ii) administering to the subject an effective amount of a checkpoint inhibitor such as an anti-PD1 antibody. In yet other embodiments, the method for increasing immune responses as provided herein may comprise administering to a subject in need thereof (e.g., a human patient as those described herein) an effective amount of a checkpoint inhibitor such as an anti-PD1 antibody, wherein the subject is on a treatment comprising an anti-Galectin-9 antibody (anti-Gal9 antibody) that binds a Galectin-9 polypeptide, e.g., any of the exemplary antibodies disclosed in Table 1 and/or Table 2.

Any of the anti-Galectin-9 antibodies described herein can be used in any of the methods described herein. In some embodiments, the anti-Galectin-9 antibody is G9.1-8m13. In some embodiments, the anti-Galectin-9 antibody is G9.2-17. In other embodiments, the anti-Galectin 9 antibody is G9.2-17mut6. As used herein, the terms "G9.1-8m13," "G9.2-17;" and "G9.2-17mut6", unless described otherwise, refer to anti-galectin 9 antibodies having the same $V_H$ and $V_L$ sequences listed in Tables 1 and 2 herein. Such antibodies may be in any suitable form, for example, full-length antibodies, antigen-binding fragments (e.g., Fab), or single chain antibodies. In some examples, any of these anti-Galectin 9 antibodies may be an IgG1 molecule (e.g., comprising the IgG1 constant region as disclosed above). In other embodiments, the anti-galectin 9 antibodies may be an IgG4 molecule, for example, comprising the IgG4 constant region set forth in SEQ ID NO: 33, 34, 35, or 36.

As used herein, the term "immune response" includes T cell-mediated and/or B cell-mediated immune responses that are influenced by modulation of immune cell activity, for example, T cell activation. In one embodiment of the disclosure, an immune response is T cell mediated. As used herein, the term "modulating" means changing or altering, and embraces both upmodulating and downmodulating. For example "modulating an immune response" means changing or altering the status of one or more immune response parameter(s). Exemplary parameters of a T cell mediated immune response include levels of T cells (e.g., an increase or decrease in effector T cells) and levels of T cell activation (e.g., an increase or decrease in the production of certain cytokines). Exemplary parameters of a B cell mediated immune response include an increase in levels of B cells, B cell activation and B cell mediated antibody production.

When an immune response is modulated, some immune response parameters may decrease and others may increase. For example, in some instances, modulating the immune response causes an increase (or upregulation) in one or more immune response parameters and a decrease (or downregulation) in one or more other immune response parameters, and the result is an overall increase in the immune response, e.g., an overall increase in an inflammatory immune response. In another example, modulating the immune response causes an increase (or upregulation) in one or more immune response parameters and a decrease (or downregulation) in one or more other immune response parameters, and the result is an overall decrease in the immune response, e.g., an overall decrease in an inflammatory response. In some embodiments an increase in an overall immune response, i.e., an increase in an overall inflammatory immune response, is determined by a reduction in tumor weight, tumor size or tumor burden. In some embodiments an increase in an overall immune response is determined by increased level(s) of one or more proinflammatory cytokine(s), e.g., including two or more, three or more, etc or a majority of proinflammatory cytokines (one or more, two or more, etc or a majority of anti-inflammatory and/or immune suppressive cytokines and/or one or more of the most potent anti-inflammatory or immune suppressive cytokines either decrease or remain constant). In some embodiments an increase in an overall immune response is determined by increased levels of one or more of the most potent proinflammatory cytokines (one or more anti-inflammatory and/or immune suppressive cytokines including one or more of the most potent cytokines either decrease or remain constant). In some embodiments an increase in an overall immune response is determined by decreased levels of one or more, including a majority of, immune suppressive and/or anti-inflammatory cytokines (the levels of one or more, or a majority of, proinflammatory cytokines, including e.g., the most potent proinflammatory cytokines, either increase or remain constant). In some embodiments, an increase in an overall immune response is determined by increased levels of one or more of the most potent anti-inflammatory and/or immune suppressive cytokines (one or more, or a majority of, proinflammatory cytokines, including, e.g., the most potent proinflammatory cytokines either increase or remain constant). In some embodiments an increase in an overall immune response is determined by a combination of any of the above.

Also, an increase (or upregulation) of one type of immune response parameter can lead to a corresponding decrease (or downregulation) in another type of immune response parameter. For example, an increase in the production of certain proinflammatory cytokines can lead to the downregulation of certain anti-inflammatory and/or immune suppressive cytokines and vice versa.

In some embodiments, the disclosure provides methods for modulating an immune response in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13, wherein modulating the immune response results in a change (upregulation and/or downregulation) in one or more immune parameters in the blood or in a tumor in the subject as compared to the level of the immune parameter(s) prior to administration of the antibody(ies) or as compared to the level of the immune parameter(s) in a control subject. In some embodiments, the methods for modulating an immune response result in an overall increase in the immune response, e.g., an increase in the proinflammatory immune response, e.g., in the blood or in a tumor of a subject.

In some embodiments, the disclosure provides methods for modulating an immune response, e.g., in blood or in a tumor in a subject, e.g., a human subject, having or suspected of having or being at risk of having a tumor, comprising administering to the subject a therapeutically effective amount of one or more of the anti-galectin-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein the immune response is modulated, e.g., in the blood or in a tumor of the subject. In some embodiments, the anti-Galectin-9 antibody is administered to a subject that is being treated with a checkpoint inhibitor. In some embodiments, a checkpoint inhibitor is administered to a subject being treated with an anti-galectin-9 antibody. In some embodiments, the anti-Galectin-9 antibody and the checkpoint inhibitor are administered concurrently. In some embodiments, the anti-Galectin-9 antibody is administered subsequently to the checkpoint inhibitor. In some embodiments, the checkpoint inhibitor is administered subsequently to the anti-Galectin-9 antibody. In some embodiments, the method comprises administering to a subject in need thereof an effective amount of an anti-Galectin-9 antibody, wherein the subject is on a treatment or planning to be on a treatment comprising a checkpoint inhibitor. In some embodiments, the method comprises administering to a subject in need thereof an effective amount of a checkpoint inhibitor, wherein the subject is on a treatment or planning to be on a treatment comprising an anti-Galectin-9 antibody. In some embodiments, the modulation of the immune response is greater than the modulation with a checkpoint inhibitor alone under the same conditions. In some embodiments, the modulation of the immune response is greater than the modulation with an anti-PD-1 antibody alone under the same conditions. In some embodiments, the modulation of the immune response is greater than the modulation with an anti-galectin-9 antibody alone under the same conditions.

In some embodiments, the disclosure provides methods for increasing an immune response (e.g., a proinflammatory immune response) in a subject, e.g., a human subject, having or suspected of having or being at risk of having a tumor, comprising administering to the subject a therapeutically effective amount of one or more of the ant-galectin-9 antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein the immune response, e.g. the pro-inflammatory response, is increased, e.g., in the blood or in a tumor of the subject, as compared to the immune response prior to treatment or as compared with the immune response in a control subject. In some embodiments, the anti-Galectin-9 antibody is administered to a subject that is being treated with a checkpoint inhibitor. In some embodiments, a checkpoint inhibitor is administered to a subject being treated with an anti-galectin-9 antibody. In some embodiments, the anti-Galectin-9 antibody and the checkpoint inhibitor are administered concurrently. In some embodiments, the anti-Galectin-9 antibody is administered subsequently to the checkpoint inhibitor. In some embodiments, the checkpoint inhibitor is administered subsequently to the anti-Galectin-9 antibody. In some embodiments, the method comprises administering to a subject in need thereof an effective amount of an anti-Galectin-9 antibody, wherein the subject is on a treatment or planning to be on a treatment comprising a checkpoint inhibitor. In some embodiments, the method comprises administering to a subject in need thereof an effective amount of a checkpoint inhibitor, wherein the subject is on a treatment or planning to be on a treatment comprising an anti-Galectin-9 antibody. In some embodiments, the increase in the immune response is greater than the increase with a checkpoint inhibitor alone under the same conditions. In some embodiments, the increase in the immune response is greater than the increase with an anti-PD-1 antibody alone under the same conditions. In some embodiments, the increase in the immune response is greater than the increase with an anti-galectin-9 antibody alone under the same conditions.

In some embodiments, the disclosure provides methods for increasing an immune response (e.g., a proinflammatory immune response), e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of the immune response (e.g., the pro-inflammatory immune response) are increased e.g., in the blood or in a tumor of the subject, to a greater extent as compared to a checkpoint inhibitor therapy alone under the same conditions.

In some embodiments, the disclosure provides methods for increasing an immune response (e.g., a proinflammatory immune response), e.g., in blood or in a tumor in a subject, e.g., a human subject, having or suspected of having or being at risk of having a tumor, comprising administering to the subject a therapeutically effective amount of one or more of the anti-galectin-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of the immune response (e.g., the pro-inflammatory immune response) are increased e.g., in the blood or in a tumor of the subject, to a greater extent as compared to anti-galectin-9 antibody therapy alone under the same conditions.

In some embodiments, the disclosure provides methods for increasing an overall immune response in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein the overall immune response, e.g. the overall pro-inflammatory response, is increased, e.g., in the blood or in a tumor of the subject, as compared to the overall immune response prior to treatment or as compared with the overall immune response in a control subject In some embodiments, the disclosure provides methods for increasing an overall immune response (e.g., an overall proinflammatory immune response), e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of the overall immune response (e.g., the overall pro-inflammatory immune response) are increased e.g., in the blood or in a tumor of the subject, to a greater extent as compared to a checkpoint inhibitor therapy alone under the same conditions. In some embodiments, the disclosure provides methods for increasing an overall immune response (e.g., an overall proinflammatory immune response), e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of the overall immune response (e.g., the overall pro-inflammatory immune response) are increased e.g., in the blood or in a tumor of the subject, to a greater extent as compared to a anti-galectin-9 antibody therapy alone under the same conditions.

In some embodiments, the disclosure provides methods for increasing one or more pro-inflammatory cytokines and/or decreasing one or more anti-inflammatory and/or immune suppressor cytokine(s) in a subject, e.g., a human subject, having or suspected of having or being at risk of having a tumor, comprising administering to the subject a therapeutically effective amount of one or more of the anti-galetin-9 antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein the level(s) of one or more proinflammatory cytokine(s) is increased and/or the level(s) of one or more anti-inflammatory and/or immune suppressor cytokine(s) is decreased, e.g., in the blood or in a tumor of the subject, as compared to the level(s) of one or more proinflammatory cytokine(s) and/or the level(s) of one or more anti-inflammatory and/or immune suppressor cytokine(s), respectively, prior to treatment or as compared to the level(s) of one or more proinflammatory cytokine(s) and/or the level(s) of one or more anti-inflammatory and/or immune suppressor cytokine(s), respectively, in a control subject.

In some embodiments, the disclosure provides methods for increasing one or more pro-inflammatory cytokines and/or decreasing one or more anti-inflammatory and/or immune suppressor cytokine(s), e.g., in blood or in a tumor in a subject, e.g., a human subject, having or suspected of having or being at risk of having a tumor, comprising administering to the subject a therapeutically effective amount of one or more of the ant-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein the level(s) of the one or more pro-inflammatory cytokine(s) is increased and/or the level(s) of one or more anti-inflammatory and/or immune suppressor cytokine(s) is decreased, e.g., in the blood or in a tumor of the subject, to a greater extent as compared to a checkpoint inhibitor therapy alone under the same conditions. In some embodiments, the disclosure provides methods for increasing one or more proinflammatory cytokine(s) and/or decreasing one or more anti-inflammatory and/or immune suppressor cytokine(s), e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein the level(s) of the one or more pro-inflammatory cytokine(s) is increased and/or the level(s) of one or more anti-inflammatory and/or immune suppressor cytokine(s) is decreased, e.g., in the blood or in a tumor of the subject, to a greater extent as compared to a anti-galectin-9 antibody therapy alone under the same conditions.

In some embodiments, the disclosure provides methods for modulating one or more immune cell populations, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein the modulation of one or more immune cell populations results in increased levels of one or more immune cell types (populations) and/or in decreased levels of one or more immune cell types (populations) e.g., in the blood or in a tumor of the subject, as compared to the level(s) of said immune cell type(s) in the subject prior to treatment or as compared to the level(s) of said immune cell type(s) in a control subject. In some embodiments, the anti-Galectin-9 antibody is administered to a subject that is being treated with a checkpoint inhibitor. In some embodiments, a checkpoint inhibitor is administered to a subject being treated with an anti-galectin-9 antibody. In some embodiments, the anti-Galectin-9 antibody and the checkpoint inhibitor are administered concurrently. In some embodiments, the anti-Galectin-9 antibody is administered subsequently to the checkpoint inhibitor. In some embodiments, the checkpoint inhibitor is administered subsequently to the anti-Galectin-9 antibody. In some embodiments, the method comprises administering to a subject in need thereof an effective amount of an anti-Galectin-9 antibody, wherein the subject is on a treatment or planning to be on a treatment comprising a checkpoint inhibitor. In some embodiments, the method comprises administering to a subject in need thereof an effective amount of a checkpoint inhibitor, wherein the subject is on a treatment or planning to be on a treatment comprising an anti-Galectin-9 antibody. In some embodiments, the increased levels of one or more immune cell types (populations) and/or the decreased levels of one or more immune cell types (populations) is greater than the increase or decrease with a checkpoint inhibitor alone under the same conditions. In some embodiments, the increased levels of one or more immune cell types (populations) and/or the decreased levels of one or more immune cell types (populations) is greater than the increase or decrease with an anti-PD-1 antibody alone under the same conditions. In some embodiments, the increased levels of one or more immune cell types (populations) and/or the decreased levels of one or more immune cell types (populations) is greater than the increase or decrease with an anti-galectin-9 antibody alone under the same conditions.

In some embodiments, the disclosure provides methods for modulating immune cell levels, e.g., in blood or in a tumor in a subject, e.g., a human subject, having or suspected of having or being at risk of having a tumor, comprising administering to the subject a therapeutically effective amount of one or more of the ant-galectin-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of immune cells are modulated e.g., in the blood or in a tumor of the subject, to a greater extent as compared to a checkpoint inhibitor therapy alone under the same conditions.

In some embodiments, the disclosure provides methods for modulating immune cell levels, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of immune cells are modulated e.g., in the blood or in a tumor of the subject, to a greater extent as compared to a anti-galectin-9 antibody therapy alone under the same conditions.

In some embodiments, the disclosure provides methods for modulating immune cell activation, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein the modulating immune cell activation results in increased or decreased activation levels of one or more immune cell types e.g., in the blood or in a tumor of the subject, as compared to the levels of said immune cell types in the subject prior to treatment or levels in a control subject.

In some embodiments, the disclosure provides methods for modulating immune cell activation, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein activation of immune cells is modulated e.g., in the blood or in a tumor of the subject, to a greater extent as compared to a checkpoint inhibitor therapy alone under the same conditions.

In some embodiments, the disclosure provides methods for modulating immune cell activation, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein activation of immune cells is modulated e.g., in the blood or in a tumor of the subject, to a greater extent as compared to an anti-galectin-9 antibody therapy alone under the same conditions.

In some embodiments, modulation of immune responses may be determined by modulation of the level of one or more immune cell markers, which, for example, may be examined in PBMCs of a subject. Exemplary immune cell markers include, but are not limited to,
CD4, CD3, CD45, CD45RA, CCR7, CD8, CD137 (4-1BB), Ki-67, PD-1, FoxP3, CD25, LAG3, TIGIT, PD-L1, CD19, CD56, NKG2D, CD11b, CD16, NKp30, CD14. CD69, CD86, CD169, CD123, CD11c, Granzyme B, CD20, CD10, CD20, CD34, CD38, CD1, CD2, CTLA-4, CD62L, and HLADR.

In some embodiments, the disclosure provides methods for increasing levels of CD8+ cells, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint 20 inhibitor, e.g., an anti-PD1 or anti-PD-L1 antibody, wherein levels of CD8+ cells are increased e.g., in the blood or in a tumor of the subject, as compared to levels in the subject prior to treatment or levels in a control subject. In some embodiments, the disclosure provides methods for increasing levels of CD8+ cells, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of CD8+ cells are increased e.g., in the blood or in a tumor of the subject, to a greater extent as compared to a checkpoint inhibitor therapy alone under the same conditions.

In some embodiments, the disclosure provides methods for increasing levels of CD8+ cells, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of CD8+ cells are increased e.g., in the blood or in a tumor of the subject, to a greater extent as compared to an anti-galectin-9 antibody therapy alone under the same conditions.

In some embodiments, the disclosure provides methods for inducing CD8+ cell proliferation, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein CD8+ cell proliferation is induced (e.g., results in increased levels of CD8+ cells) e.g., in the blood or in a tumor of the subject, as compared to CD8+ cell proliferation in the subject prior to treatment or CD8+ cell proliferation in a control subject.

In some embodiments, the disclosure provides methods for for inducing CD8+ cell proliferation, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein CD8+ cell proliferation is induced e.g., in the blood or in a tumor of the subject, to a greater extent as compared to a checkpoint inhibitor therapy alone under the same conditions.

In some embodiments, the disclosure provides methods for for inducing CD8+ cell proliferation, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein CD8+ cell proliferation is induced e.g., in the blood or in a tumor of the subject, to a greater extent as compared to an anti-galectin-9 antibody therapy alone under the same conditions.

In some embodiments, the disclosure provides methods for inducing of CD4+ cell proliferation, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein wherein CD4+ cell proliferation is induced (e.g., results in increased levels of CD4+ cells) e.g., in the blood or in a tumor of the subject, as compared to CD4+ cell proliferation in the subject prior to treatment or CD4+ cell proliferation in a control subject.

In some embodiments, the disclosure provides methods for inducing CD4+ cell proliferation, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein CD4+ cell proliferation is induced e.g., in the blood or in a tumor of the subject, to a greater extent as compared to a checkpoint inhibitor therapy alone under the same conditions.

In some embodiments, the disclosure provides methods for inducing CD4+ cell proliferation, e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein CD4+ cell proliferation is induced e.g., in the blood or in a tumor of the subject, to a greater extent as compared to an anti-galectin-9 antibody therapy alone under the same conditions.

In some embodiments, the disclosure provides methods for modulating the level(s) of one or more cytokine(s), e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein the modulating of the level(s) of one or more cytokine(s) results in a change, e.g., decrease or increase in the level(s) of one or more cytokine(s) e.g., in the blood or in a tumor of the subject, as compared to the level(s) prior to treatment or the level(s) in a control subject. Non-limiting examples of cytokines which are modulated according to the methods described herein include but are not limited to TNFa, IL-10, MCP-1, IL-2, IL-6, IL-17a, IL-8, IL-5, IL-1b, IL-4, IL-12, TNFa, and IFN-g.

In some embodiments, the disclosure provides methods for modulating the level(s) of one or more cytokine(s), e.g., in blood or in a tumor in a subject, e.g., a human subject, having or suspected of having or being at risk of having a tumor, comprising administering to the subject a therapeutically effective amount of one or more of the anti-gal-9 antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein the level(s) of one or more cytokine(s) are modulated, e.g., increased and/or decreased e.g., in the blood or in a tumor of the subject, to a greater extent as compared to a checkpoint inhibitor therapy alone under the same conditions. In some embodiments, the disclosure provides methods for modulating levels of one or more cytokines, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein the level(s) of one or more cytokine(s) are modulated, e.g., increased and/or decreased e.g., in the blood or in a tumor of the subject, to a greater extent as compared to an anti-galectin-9 antibody therapy alone under the same conditions. Non-limiting examples of cytokines which are modulated according to the methods described herein include but are not limited to TNFa, IL-10, MCP-1, IL-2, IL-6, IL-17a, IL-8, IL-5, IL-1b, IL-4, IL-12, TNFa, and IFN-g.

In some embodiments, the disclosure provides methods for increasing levels of TNFalpha, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of TNFalpha are increased e.g., in the blood or in a tumor of the subject, as compared to levels of TNFalpha prior to treatment or levels in a control subject.

In some embodiments, the disclosure provides methods for for increasing levels of TNFalpha, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of TNFalpha levels are increased e.g., in the blood or in a tumor of the subject, to a greater extent as compared to a checkpoint inhibitor therapy alone under the same conditions.

In some embodiments, the disclosure provides methods for for increasing levels of TNFalpha, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of TNFalpha levels are increased e.g., in the blood or in a tumor of the subject, to a greater extent as compared to an anti-galectin-9 antibody therapy alone under the same conditions.

In some embodiments, the disclosure provides methods for inducing TNFalpha expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of TNFalpha produced by CD3+ cells are increased e.g., in the blood or in a tumor of the subject, as compared to levels of TNFalpha prior to treatment or levels in a control subject.

In some embodiments, the disclosure provides methods for inducing TNFalpha expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for TNFalpha expression in CD3+ cells is induced e.g., in the blood or in a tumor of the subject, to a greater extent as compared to a checkpoint inhibitor therapy alone under the same conditions.

In some embodiments, the disclosure provides methods for inducing TNFalpha expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for TNFalpha expression in CD3+ cells is induced e.g., in the blood or in a tumor of the subject, to a greater extent as compared to an anti-galectin-9 antibody therapy alone under the same conditions.

In some embodiments, the disclosure provides methods for inducing TNFalpha expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of TNFalpha produced by CD8+ cells are increased e.g., in the blood or in a tumor of the subject, as compared to levels of TNFalpha prior to treatment or levels in a control subject.

In some embodiments, the disclosure provides methods for inducing TNFalpha expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for TNFalpha expression in CD8+ cells is induced e.g., in the blood or in a tumor of the subject, to a greater extent as compared to a checkpoint inhibitor therapy alone under the same conditions.

In some embodiments, the disclosure provides methods for inducing TNFalpha expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for TNFalpha expression in CD8+ cells is induced e.g., in the blood or in a tumor of the subject, to a greater extent as compared to an anti-galectin-9 antibody therapy alone under the same conditions.

In some embodiments, the disclosure provides methods for inducing TNFalpha expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of TNFalpha produced by CD4+ cells are increased e.g., in the blood or in a tumor of the subject, as compared to levels of TNFalpha prior to treatment or levels in a control subject.

In some embodiments, the disclosure provides methods for inducing TNFalpha expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for TNFalpha expression in CD4+ cells is induced e.g., in the blood or in a tumor of the subject, to a greater extent as compared to a checkpoint inhibitor therapy alone under the same conditions.

In some embodiments, the disclosure provides methods for inducing TNFalpha expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for TNFalpha expression in CD4+ cells is induced e.g., in the blood or in a tumor of the subject, to a greater extent as compared to an anti-galectin-9 antibody therapy alone under the same conditions.

In some embodiments, the disclosure provides methods for increasing levels of CD44, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of CD44 are increased e.g., in the blood or in a tumor of the subject, as compared to levels of CD44 prior to treatment or levels in a control subject.

In some embodiments, the disclosure provides methods for for increasing levels of CD44, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or 30 anti-PD-L1 antibody, wherein levels of CD44 levels are increased e.g., in the blood or in a tumor of the subject, to a greater extent as compared to a checkpoint inhibitor therapy alone under the same conditions.

In some embodiments, the disclosure provides methods for for increasing levels of CD44, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of CD44 levels are increased e.g., in the blood or in a tumor of the subject, to a greater extent as compared to an anti-galectin-9 antibody therapy alone under the same conditions.

In some embodiments, the disclosure provides methods for inducing CD44 expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of CD44 produced by CD3+ cells are increased e.g., in the blood or in a tumor of the subject, as compared to levels of CD44 prior to treatment or levels in a control subject.

In some embodiments, the disclosure provides methods for inducing CD44 expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for CD44 expression in CD3+ cells is induced e.g., in the blood or in a tumor of the subject, to a greater extent as compared to a checkpoint inhibitor therapy alone under the same conditions.

In some embodiments, the disclosure provides methods for inducing CD44 expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for CD44 expression in CD3+ cells is induced e.g., in the blood or in a tumor of the subject, to a greater extent as compared to an anti-galectin-9 antibody therapy alone under the same conditions.

In some embodiments, the disclosure provides methods for inducing CD44 expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of CD44 produced by CD8+ cells are increased e.g., in the blood or in a tumor of the subject, as compared to levels of CD44 prior to treatment or levels in a control subject.

In some embodiments, the disclosure provides methods for inducing CD44 expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for CD44 expression in CD8+ cells is induced e.g., in the blood or in a tumor of the subject, to a greater extent as compared to a checkpoint inhibitor therapy alone under the same conditions.

In some embodiments, the disclosure provides methods for inducing CD44 expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for CD44 expression in CD8+ cells is induced e.g., in the blood or in a tumor of the subject, to a greater extent as compared to an anti-galectin-9 antibody therapy alone under the same conditions.

In some embodiments, the disclosure provides methods for inducing CD44 expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of CD44 produced by CD4+ cells are increased e.g., in the blood or in a tumor of the subject, as compared to levels of CD44 prior to treatment or levels in a control subject.

In some embodiments, the disclosure provides methods for inducing CD44 expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for CD44 expression in CD4+ cells is induced e.g., in the blood or in a tumor of the subject, to a greater extent as compared to a checkpoint inhibitor therapy alone under the same conditions.

In some embodiments, the disclosure provides methods for inducing CD44 expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein for CD44 expression in CD4+ cells is induced e.g., in the blood or in a tumor of the subject, to a greater extent as compared to an anti-galectin-9 antibody therapy alone under the same conditions.

In some embodiments, the disclosure provides methods for increasing levels of IFNgamma, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of IFNgamma are increased e.g., in the blood or in a tumor of the subject, as compared to levels of IFNgamma prior to treatment or levels in a control subject.

In some embodiments, the disclosure provides methods for increasing levels of IFNgamma, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein levels of IFNgamma are increased e.g., in the blood or in a tumor of the subject, to a greater extent as compared to a checkpoint inhibitor therapy alone under the same conditions.

In some embodiments, the disclosure provides methods for increasing levels of IFNgamma, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or 20 anti-PD-L1 antibody, wherein levels of IFNgamma are increased e.g., in the blood or in a tumor of the subject, to a greater extent as compared to an anti-galectin-9 antibody therapy alone under the same conditions.

In some embodiments, the disclosure provides methods for inducing IFNgamma expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., an anti-PD1 or anti-PD-L1 antibody, wherein levels of IFNgamma produced by CD3+ cells are increased e.g., in the blood or in a tumor of the subject, as compared to levels of IFNgamma prior to treatment or levels in a control subject.

In some embodiments, the disclosure provides methods for inducing IFNgamma expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein IFNgamma expression in CD3+ cells is induced e.g., in the blood or in a tumor of the subject, to a greater extent as compared to a checkpoint inhibitor therapy alone under the same conditions.

In some embodiments, the disclosure provides methods for inducing IFNgamma expression in CD3+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein IFNgamma expression in CD3+ cells is induced e.g., in the blood or in a tumor of the subject, to a greater extent as compared to an anti-galectin-9 antibody therapy alone under the same conditions.

In some embodiments, the disclosure provides methods for inducing IFNgamma expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., 25 an anti-PD1 or anti-PD-L1 antibody, wherein levels of IFNgamma expressed by CD4+ cells are increased e.g., in the blood or in a tumor of the subject, as compared to levels of IFNgamma prior to treatment or levels in a control subject.

In some embodiments, the disclosure provides methods for inducing IFNgamma expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein IFNgamma expression in CD4+ cells is induced e.g., in the blood or in a tumor of the subject, to a greater extent as compared to a checkpoint inhibitor therapy alone under the same conditions.

In some embodiments, the disclosure provides methods for inducing IFNgamma expression in CD4+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein IFNgamma expression in CD4+ cells is induced e.g., in the blood or in a tumor of the subject, to a greater extent as compared to an anti-galectin-9 antibody therapy alone under the same conditions.

In some embodiments, the disclosure provides methods for inducing IFNgamma expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) alone or in combination with a checkpoint inhibitor, e.g., 20 an anti-PD1 or anti-PD-L1 antibody, wherein levels of IFNgamma produced by CD8+ cells are increased e.g., in the blood or in a tumor of the subject, as compared to levels of IFNgamma prior to treatment or levels in a control subject.

In some embodiments, the disclosure provides methods for for inducing IFNgamma expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein IFNgamma expression in CD8+ cells is induced e.g., in the blood or in a tumor of the subject, to a greater extent as compared to a checkpoint inhibitor therapy alone under the same conditions.

In some embodiments, the disclosure provides methods for for inducing IFNgamma expression in CD8+ cells, e.g., in blood or in a tumor in a subject, e.g., a human subject, having or suspected of having or being at risk of having a tumor, comprising administering to the subject a therapeutically effective amount of one or more of the antibodies described herein, e.g., in Table 1 and/or Table 2, including, but not limited to, 9.2-17 and 9.1-8mut13 (e.g., in IgG1 form or IgG4 form as disclosed herein) in combination with a checkpoint inhibitor, e.g., an anti-PD1 or anti-PD-L1 antibody, wherein IFNgamma expression in CD8+ cells is induced e.g., in the blood or in a tumor of the subject, to a greater extent as compared to an anti-galectin-9 antibody therapy alone under the same conditions.

In any of these embodiments, the anti-Galectin-9 antibody is administered to a subject that is being treated with a checkpoint inhibitor. In any of these embodiments, a checkpoint inhibitor is administered to a subject being treated with an anti-galectin-9 antibody. In any of these embodiments, the anti-Galectin-9 antibody and the checkpoint inhibitor are administered concurrently. In any of these embodiments, the anti-Galectin-9 antibody is administered subsequently to the checkpoint inhibitor. In any of these embodiments, the checkpoint inhibitor is administered subsequently to the anti-Galectin-9 antibody. In any of these embodiments, the method comprises administering to a subject in need thereof an effective amount of an anti-Galectin-9 antibody, wherein the subject is on a treatment or planning to be on a treatment comprising a checkpoint inhibitor. In any of these embodiments, the method comprises administering to a subject in need thereof an effective amount of a checkpoint inhibitor, wherein the subject is on a treatment or planning to be on a treatment comprising an anti-Galectin-9 antibody. In any of these embodiments, the effect on the immune response is greater than the effect with a checkpoint inhibitor alone under the same conditions. In any of these embodiments, the effect on the immune response is greater than the effect with an anti-PD-1 antibody alone under the same conditions. In any of these embodiments, the effect on the immune response is greater than the effect with an anti-galectin-9 antibody alone under the same conditions.

Pharmaceutical Compositions

Any of the anti-Galectin-9 antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). In some examples, the pharmaceutical composition described herein comprises liposomes containing the antibodies (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-Galectin-9 antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid 15 copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation. For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0.im, particularly 0.1 and 0.5.im, and have a pH in the range of 5.5 to 8.0.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Therapeutic Applications

To practice the methods disclosed herein, an effective amount of the pharmaceutical composition described herein can be administered to a subject (e.g., a human) in need of the treatment via a suitable route, systemically or locally. In some embodiments, the anti-Galectin-9 antibodies are administered by intravenous administration, e.g., as a bolus or by continuous infusion over a period of time, by intramuscular, intraperitoneal, intracerebrospinal, subcutaneous, intra-arterial, intra-articular, intrasynovial, intrathecal, intratumoral, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

In some embodiments, the anti-Galectin-9 antibody is G9.1-8m13. In some embodiments, the anti-Galectin-9 antibody is G9.2-17. In other embodiments, the anti-Galectin 9 antibody is G9.2-17mut6. Non-limiting examples of such antibodies include for example antibody 9.2-17 or 9.1-8mut13. Any of these anti-Galectin 9 antibodies may be an IgG1 molecule (e.g., comprising the IgG1 constant region as disclosed above). In other embodiments, the anti-galectin 9 antibodies may be an IgG4 molecule, for example, comprising the IgG4 constant region set forth in SEQ ID NO: 33, 34, or 35.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as a solid tumor, hematological malignancy, autoimmune disease (such as an allergic disorder), microbial disease, and fibrotic condition.

In some embodiments, the subject is a human patient who is in need of enhancing immunity. For example, the human patient may have a solid tumor. Examples of solid tumor cancers include pancreatic duct adenocarcinoma (PDA), colorectal cancer (CRC), melanoma, cholangiocarcinoma, breast cancer, lung cancer (for example, non-small cell lung cancer, NSCLC, and small cell lung cancer, SCLC), upper and lower gastrointestinal malignancies (including, but not limited to, esophageal, gastric, and hepatobiliary cancer), squamous cell head and neck cancer, genitourinary cancers, ovarian cancer, and sarcomas. Hematological malignancies include acute lymphoblastic leukemia, chronic lymphocytic leukemia, lymphomas, multiple myeloma, acute myelogenous leukemia, chronic myelogenous leukemia, myelodysplastic syndromes and the myeloproliferative neoplasms, such as essential thrombocythemia, polycythemia vera and myelofibrosis. A subject having a solid tumor or a hematological malignancy can be identified by routine medical examination, e.g., laboratory tests, organ functional tests, CT scans, or ultrasounds. In some embodiments, the subject to be treated by the method described herein may be a human cancer patient who has undergone or is subjecting to an anti-cancer therapy, for example, chemotherapy, radiotherapy, immunotherapy, or surgery.

In other embodiments, the human patient may have an autoimmune disease. Examples of autoimmune diseases include rheumatoid conditions, metabolic and endocrine conditions, as well as respiratory and allergic conditions. A subject having an autoimmune disease can be identified by routine medical examination, e.g., with laboratory tests, such as antinuclear antibodies, anti-mitochondrial autoantibodies, anti-neutrophil cytoplasmic antibody, anti-phospholipid antibodies, anti-citrullinated peptide (anti-CCP), anti-rheumatoid factor, immunoglobulin A, C-reactive protein test, complement test, erythrocyte sedimentation rate (ESR) test, blood clotting profile, and protein electrophoresis/immunofixation electrophoresis, among others. In some embodiments, the subject to be treated by the method described herein may be a human subject with an autoimmune disease who has undergone or is subjecting to an autoimmune disease treatment, for example, immunosuppressive mediation, hormone replacement therapy, blood transfusions, anti-inflammatory medication, and/or pain medication.

In other embodiments, the human patient may have a microbial diseases, which may be caused by a variety of pathogens, including bacteria, fungi, protozoa and viruses. Exemplary infectious bacteria include *Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococcus aureus, Vibrio colerae, Escherichia coli, Pseudomonas aeruginosa, Campylobacter* (*Vibrio*) *fetus, Aeromonas hydrophila, Bacillus aereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi*, and *Chlamydia* spp. Examples of pathologic fungi include *Coccidioides immitis*, Aspergillus-fumigatus, *Candida albicans, Blastomyces dermatitidis, Cryptococcus neoformans*, and *Histoplasma capsulatum*. Pathologic protozoa include *Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum*, and *Plasmodium malaria*. Examples of helminiths include *Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms. Viral infectious diseases include those caused by Adenovirus, Lassa fever virus (Arenavirus), Astrovirus, Hantavirus, Rift Valley Fever virus (Phlebovirus), Calicivirus, Ebola virus, Marburg Virus, Japanese encephalitis virus, Dengue virus, Yellow fever virus, Hepatitis C virus, Hepatitis G virus, Hepatitis B virus, Hepatitis D virus, Herpes simplex virus 1, Herpes simplex virus 2, Cytomegalovirus, Epstein Barr virus, Varicella Zoster Virus, Human Herpesvirus 7, Human Herpesvirus 8, Influenza virus, Parainfluenza virus, Rubella virus, Mumps virus, Morbillivirus, Measles virus, Respiratory Syncytial virus, Papillomaviruses, JC virus (Polyomavirus), BK virus (Polyomavirus), Parvovirus, Coxsackie virus (A and B), Hepatitis A virus, Polioviruses, Rhinoviruses, Reovirus, Rabies Virus (Lyssavirus), Human Immunodeficiency virus 1 and 2, and Human T-cell Leukemia virus. A subject having a microbial disease can be identified by routine medical examination, e.g., laboratory tests. For example, microscopy (e.g., Gram-positive and/or Gram-negative staining), sample culturing, biochemical tests (e.g., tests for metabolic and/or enzymatic products, such as fermentation products, acids, alcohol, or gases), and molecular diagnostics (e.g., PCR) may be used. In some embodiments, the subject to be treated by the method described herein may be a human infectious disease patient who has undergone or is subjecting to an antimicrobial therapy, for example, immunotherapy.

In yet other embodiments, the human patient may have a fibrotic condition. Examples of fibrotic conditions include pulmonary fibrosis (e.g., cystic fibrosis, idiopathic pulmonary fibrosis), cirrhosis, biliary atresia, atrial fibrosis, endomyocardial fibrosis, glial scar, arthrofibrosis, Crohn's disease, Dupuytren's contracture, keloid, mediastinal fibrosis, myelofibrosis, nephrogenic systemic fibrosis, progressive massive fibrosis, retroperitoneal fibrosis, and scleroderma/systemic sclerosis. A subject having a fibrotic condition can be identified by routine medical examination, e.g., laboratory tests, CT scans, X-rays, echocardiograms, or ultrasounds. In some embodiments, the subject to be treated by the method described herein may be a human fibrotic patient who has undergone or is subjecting to an anti-fibrotic therapy, for example medication, physical therapy, oxygen therapy, or surgery.

A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. In some embodiments, the therapeutic effect is reduced Galectin-9 activity and/or amount/expression, reduced Dectin-1 signaling, reduced TIM-3 signaling, reduced CD206 signaling, or increased anti-tumor immune responses in the tumor microenvironment. Non-limiting examples of increased anti-tumor responses include increased activation levels of effector T cells, or switching of the TAMs from the M2 to the M1 phenotype, and increased ADCC responses. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, such as those described in Table 1 or Table 2 herein, such as for example, antibody 9.2-17 and antibody 9.1-8mut13, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. In some examples, the dosage of the anti-Galectin-9 antibody described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically, the clinician will administer an antibody, until a dosage is reached that achieves the desired result. In some embodiments, the desired result is an increase in anti-tumor immune response in the tumor microenvironment. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, methods are provided herein, wherein the antibodies described herein, e.g., in Table 1 and/or Table 2, including, but not limited to, 9.2-17 and 9.1-8mut13, are administered to a subject in need of the treatment at an amount sufficient to increase and/or induce CD8+ and/or CD4+ cell proliferation, e.g., in blood or in a tumor. In some embodiments, the antibodies described herein, e.g., in Table 1 and/or Table 2, including, but not limited to, 9.2-17 and 9.1-8mut13, are administered to a subject in need of the treatment at an amount sufficient to increase and/or induce CD8+ and/or CD4+ cell proliferation e.g., in blood or in a tumor. In some embodiments, the antibodies described herein, e.g., in Table 1 and/or Table 2, including, but not limited to, 9.2-17 and 9.1-8mut13, are administered to a subject in need of the treatment at an amount sufficient to increase and/or induce CD8+ and/or CD4+ cell proliferation, e.g., in blood or in a tumor of the subject. in a tumor by at least 20% (e.g., 20%, 30%, 40%, 50%, 60%, 70%, 80%, 90% or greater) in vivo (as compared to levels prior to treatment or in a control subject).

In some embodiments, the antibodies described herein, e.g., in Table 1 and/or Table 2, including, but not limited to, 9.2-17 and 9.1-8mut13 (e.g., in IgG1 form or IgG4 form as disclosed herein), are administered to a subject in need of the treatment at an amount sufficient to modulate cytokine levels, e.g., in a tumor. In some embodiments, the antibodies described herein, e.g., in Table 1 and/or Table 2, including, but not limited to, 9.2-17 and 9.1-8mut13, are administered to a subject in need of the treatment at an amount sufficient to modulate cytokine levels, e.g., in blood or in a tumor of the subject by at least 20% (e.g., 20%, 30%, 40%, 50%, 60%, 70%, 80%, 90% or greater) in vivo (as compared to levels prior to treatment or in a control subject). In some embodiments, the antibodies described herein, e.g., in Table 1 and/or Table 2, including, but not limited to, 9.2-17 and 9.1-8mut13 (e.g., in IgG1 form or IgG4 form as disclosed herein), are administered to a subject in need of the treatment at an amount sufficient to increase and/or induce TNFalpha expression in CD8+ cells, e.g., in the blood or in a tumor of the subject. In some embodiments, the antibodies described herein, e.g., in Table 1 and/or Table 2, including, but not limited to, 9.2-17 and 9.1-8mut13, are administered to a subject in need of the treatment at an amount sufficient to increase and/or induce TNFalpha expression in CD8+ cells, e.g., in the blood or in a tumor of the subject by at least 20% (e.g., 20%, 30%, 40%, 50%, 60%, 70%, 80%, 90% or greater) in vivo (as compared to levels prior to treatment or in a control subject).

In some embodiments, methods are provided herein, wherein the antibodies described herein, e.g., in Table 1 and/or Table 2, including, but not limited to, 9.2-17 and 9.1-8mut13 (e.g., in IgG1 form or IgG4 form), are administered to a subject in need of the treatment at an amount sufficient to increase and/or induce IFNgamma expression in CD4+ cells, e.g., in the blood or in a tumor of the subject. In some embodiments, the antibodies described herein, e.g., in Table 1 and/or Table 2, including, but not limited to, 9.2-17 and 9.1-8mut13, are administered to a subject in need of the treatment at an amount sufficient to increase and/or induce IFNgamma expression in CD4+ cells, e.g., in the blood or in a tumor of the subject. In some embodiments, the antibodies described herein, e.g., in Table 1 and/or Table 2, including, but not limited to, 9.2-17 and 9.1-8mut13, are administered to a subject in need of the treatment at an amount sufficient to increase and/or induce IFNgamma expression in CD4+ cells, e.g., in the blood or in a tumor of the subject by at least 20% (e.g., 20%, 30%, 40%, 50%, 60%, 70%, 80%, 90% or greater) in vivo (as compared to levels prior to treatment or in a control subject).

In some embodiments, methods are provided herein, wherein the antibodies described herein, e.g., in Table 1 and/or Table 2, including, but not limited to, 9.2-17 and 9.1-8mut13, are administered to a subject in need of the treatment at an amount sufficient to increase and/or induce IFNgamma expression in CD8+ cells, e.g., in the blood or in a tumor of the subject. In some embodiments, the antibodies described herein, e.g., in Table 1 and/or Table 2, including, but not limited to, 9.2-17 and 9.1-8mut13, are administered to a subject in need of the treatment at an amount sufficient to increase and/or induce IFNgamma expression in CD8+ cells in a tumor. In some embodiments, the antibodies described herein, e.g., in Table 1 and/or Table 2, including, but not limited to, 9.2-17 and 9.1-8mut13, are administered to a subject in need of the treatment at an amount sufficient to increase and/or induce IFNgamma expression in CD8+ cells, e.g., in the blood or in a tumor of the subject by at least 20% (e.g., 20%, 30%, 40%, 50%, 60%, 70%, 80%, 90% or greater) in vivo (as compared to levels prior to treatment or in a control subject).

In some embodiments, methods are provided herein, wherein immune cell populations in tumor samples are analyzed in vitro or ex vivo. Accordingly methods are provided herein, wherein the antibodies described herein, e.g., in Table 1 and/or Table 2, including, but not limited to, 9.2-17 and 9.1-8mut13, are provided in vitro or ex vivo at an amount sufficient to increase and/or induce IFNgamma expression in effector T cells in a tumor. In some embodiments, the antibodies described herein, e.g., in Table 1 and/or Table 2, including, but not limited to, 9.2-17 and 9.1-8mut13, are provided in vitro or ex vivo at an amount sufficient to increase and/or induce IFNgamma expression in effector T cells in a tumor. In some embodiments, the antibodies described herein, e.g., in Table 1 and/or Table 2, including, but not limited to, 9.2-17 and 9.1-8mut13, increase and/or induce IFNgamma expression in effector T cells in a tumor by at least 20% (e.g., 20%, 30%, 40%, 50%, 60%, 70%, 80%, 90% or greater) in vitro or ex vivo.

In some embodiments, administration of one or more of the antibodies described herein results in a reduction in tumor size, reduction in tumor growth, elimination of the tumor, reduction in number of metastatic lesions over time, complete response, partial response, or stable disease. Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, intratumoral, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol*. (1993) 11:202; Chiou et al., Gene Therapeutics: Methods And Applications Of Direct Gene Transfer (J. A. Wolff, ed.) (1994); Wu et al., *J. Biol. Chem*. (1988) 263:621; Wu et al., *J. Biol. Chem*. (1994) 269:542; Zenke et al., *Proc. Natl. Acad. Sci. USA* (1990) 87:3655; Wu et al., *J. Biol. Chem*. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther*. (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther*. (1992) 3:147); ligand-linked DNA (see, e.g., Wu, *J. Biol. Chem*. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell. Biol*. (1994) 14:2411, and in Woffendin, *Proc. Natl. Acad. Sci*. (1994) 91:1581.

In some embodiments, messenger RNAs (mRNAs) coding for any of the anti-galectin 9 antibodies disclosed herein may be used for delivering the antibody to a subject. The mRNAs may comprise naturally-occurring nucleotide and/or nucleoside residues. Alternatively, the mRNAs may comprise one or more modified nucleotide and/or nucleoside residues. Any modified nucleosides and/or nucleotides may be used for making the modified mRNA as disclosed herein. Examples include those described in US20160256573, the relevant disclosures are incorporated by reference for the purpose and subject matter referenced herein. In other examples, the mRNA molecule may be modified to have reduced uracil content. See, e.g., US20160237134, the relevant disclosures are incorporated by reference for the purpose and subject matter referenced herein.

The particular dosage regimen, i.e., dose, timing and repetition, used in the method described herein will depend on the particular subject and that subject's medical history.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents. Treatment efficacy for a target disease/disorder can be assessed by methods well-known in the art.

In some embodiments, the disclosure provides a method for promoting (increasing and/or inducing) T cell activation, e.g., in tumor infiltrating T cells, i.e., suppress Galectin-9 mediated inhibition of T cell activation, either directly or indirectly, the method comprising providing or administering an anti-Galectin-9 antibody described herein, e.g., in Table 1 and/or Table 2, to a subject. In some embodiments, the anti-Galectin-9 antibody is a 9.1-8mut13 antibody and/or a 9.2-17 antibody. In some embodiments, the method promotes T cell activation by at least 20% (e.g., 20%, 30%, 35%, 40%, 50%, 60%, 70%, 80%, 90%, 95% or greater, including any increment therein).

In some embodiments, the disclosure provides a method for promoting (increasing and/or inducing) CD4+ cell activation, the method comprising providing or administering an anti-Galectin-9 antibody described herein, e.g., in Table 1 and/or Table 2, to a subject. In some embodiments, the anti-Galectin-9 antibody is a 9.1-8mut13 antibody and/or a 9.2-17 antibody. In some embodiments, the method promotes CD4+ cell activation by at least 20% (e.g., 20%, 30%, 40%, 50%, 60%, 70%, 80%, 90%, 95% or greater, including any increment therein).

In some embodiments, the disclosure provides a method for increasing and/or inducing CD44 expression in CD4+ cells, the method comprising providing or administering an anti-Galectin-9 antibody described herein, e.g., in Table 1 and/or Table 2, or to a subject. In some embodiments, the anti-Galectin-9 antibody is a 9.1-8mut13 antibody and/or a 9.2-17 antibody. In some embodiments, the method increases and/or induces CD44 expression in CD4+ cells by at least 20% (e.g., 20%, 30%, 40%, 50%, 60%, 70%, 80%, 90%, 95% or greater, including any increment therein). In some embodiments, the anti-gal-9 antibody is administered with a checkpoint inhibitor.

In some embodiments, the disclosure provides a method for increasing and/or inducing IFNgamma expression in CD4+ cells, the method comprising providing or administering an anti-Galectin-9 antibody described herein, e.g., in Table 1 and/or Table 2, or to a subject. In some embodiments, the anti-Galectin-9 antibody is a 9.1-8mut13 antibody and/or a 9.2-17 antibody. In some embodiments, the method increases and/or induced IFNgamma expression in CD4+ cells by at least 20% (e.g., 20%, 30%, 40%, 50%, 60%, 70%, 80%, 90%, 95% or greater, including any increment therein). In some embodiments, the anti-gal-9 antibody is administered with a checkpoint inhibitor.

In some embodiments, the disclosure provides a method for increasing and/or inducing TNFalpha expression in CD4+ cells, the method comprising providing or administering an anti-Galectin-9 antibody described herein, e.g., in Table 1 and/or Table 2, or to a subject. In some embodiments, the anti-Galectin-9 antibody is a 9.1-8mut13 antibody and/or a 9.2-17 antibody. In some embodiments, the method increases and/or induces TNFalpha expression in CD4+ cells by at least 20% (e.g., 20%, 30%, 40%, 50%, 60%, 70%, 80%, 90%, 95% or greater, including any increment therein). In some embodiments, the anti-gal-9 antibody is administered with a checkpoint inhibitor.

In some embodiments, the disclosure provides a method for increasing and/or inducing CD44 expression in CD8+ cells, the method comprising providing or administering an anti-Galectin-9 antibody described herein, e.g., in Table 1 and/or Table 2, to a subject. In some embodiments, the anti-Galectin-9 antibody is a 9.1-8mut13 antibody and/or a 9.2-17 antibody. In some embodiments, the method increases and/or induces CD44 expression in CD8+ cells by at least 20% (e.g., 20%, 30%, 40%, 50%, 60%, 70%, 80%, 90%, 95% or greater, including any increment therein). In some embodiments, the anti-gal-9 antibody is administered with a checkpoint inhibitor.

In some embodiments, the disclosure provides a method for increasing and/or inducing IFNgamma expression in CD8+ cells, the method comprising providing or administering an effective amount of an anti-Galectin-9 antibody described herein, e.g., in Table 1 and/or Table 2, to a subject. In some embodiments, the anti-Galectin-9 antibody is a 9.1-8mut13 antibody and/or a 9.2-17 antibody. In some embodiments, the method increases and/or induces IFNgamma expression in CD8+ cells by at least 20% (e.g., 20%, 30%, 40%, 50%, 60%, 70%, 80%, 90%, 95% or greater, including any increment therein). In some embodiments, the anti-gal-9 antibody is administered with a checkpoint inhibitor.

In some embodiments, the disclosure provides a method for increasing and/or inducing TNFalpha expression in CD8+ cells, the method comprising providing or administering an effective amount of an anti-Galectin-9 antibody described herein, e.g., in Table 1 and/or Table 2, to a subject. In some embodiments, the anti-Galectin-9 antibody is a 9.1-8mut13 antibody and/or a 9.2-17 antibody. In some embodiments, the method increases and/or induces TNFalpha expression in CD8+ cells by at least 20% (e.g., 20%, 30%, 40%, 50%, 60%, 70%, 80%, 90%, 95% or greater, including any increment therein). In some embodiments, the anti-gal-9 antibody is administered with a checkpoint inhibitor.

In some of these embodiments, the methods comprising providing or administering an effective amount of an anti-Galectin-9 antibody described herein, increase and/or induce CD44, IFNgamma, and/or TNFalpha in CD4+ and CD8+ cells. The method embodiments described supra, for suppressing Dectin-1 signaling, for suppressing TIM-3 signaling, for suppressing CD206 signaling, for inducing ADCC against target cells, for inducing CDC against target cell, for inducing ADCP against target cells, for inducing T cell activation, for promoting CD4+ cell activation, for inducing CD44 expression in CD4+ cells, for inducing IFNgamma expression in CD4+ cells, for inducing TNFalpha expression in CD4+ cells, for inducing CD44 expression in CD8+ cells, for inducing IFNgamma expression in CD8+ cells, method for inducing TNFalpha expression in CD8+ cells, wherein the method includes administering to a subject in need thereof an effective amount of an anti-Galectin-9 antibody described herein, e.g., in Table 1 and/or Table 2. In some embodiments, the anti-gal-9 antibody is administered with a checkpoint inhibitor.

Any of the anti-Galectin-9 antibodies described herein may be utilized in conjunction with an immune checkpoint inhibitor and/or other types of therapy for cancer or autoimmune diseases, such as chemotherapy, surgery, radiation, gene therapy, or in conjunction with other types of therapy for autoimmune diseases, such as immunosuppressive mediation, hormone replacement therapy, blood transfusions, anti-inflammatory medication, and/or pain medication and so forth. Such therapies can be administered simultaneously or sequentially (in any order) with the immunotherapy according to the present disclosure.

In some embodiments, methods are provided herein, wherein the anti-Galectin-9 antibodies described herein are utilized in conjunction with other types of therapy for cancer or autoimmune diseases, such as chemotherapy, surgery, radiation, gene therapy, or in conjunction with other types of therapy for autoimmune diseases, such as immunosuppressive mediation, hormone replacement therapy, blood transfusions, anti-inflammatory medication, and/or pain medication and so forth. In some embodiments, the methods include the steps of administering the anti-Galectin-9 antibodies, such as any of the anti-Galectin-9 antibodies described herein, e.g., in Table 1 and/or Table 2, simultaneously or sequentially (in any order) with the immunotherapy according to the present disclosure. When co-administered with an additional therapeutic agent, suitable therapeutically effective dosages for each agent may be lowered due to the additive action or synergy.

In some embodiments, the methods are provided herein, wherein the anti-Galectin-9 antibody, for example antibody 9.2-17 or 9.1-8mut13, is combined with other immunomodulatory treatments such as, e.g., inhibitors of a checkpoint molecule (e.g., PD-1, PD-L1, PD-L2, CTLA-4, LAG3, TIM3, or A2aR), activators of a co-stimulatory receptor (e.g., DX40, GITR, CD137, CD40, CD27, and ICOS), and/or inhibitors of an innate immune cell target (e.g., KIR, NKG2A, CD96, TLR, and IDO). Without being bound by theory, it is thought that anti-Galectin-9 antibodies, through their inhibition of Dectin-1, can reprogram immune responses against tumor cells via, e.g., inhibiting the activity of γδ T cells infiltrated into tumor microenvironment, and/or enhancing immune surveillance against tumor cells by, e.g., activating CD4+ and/or CD8+ T cells. Thus, combined use of an anti-Galectin-9 antibody and an immunomodulatory agent such as those described herein would be expected to significantly enhance anti-tumor efficacy.

In some embodiments, the methods are provided, wherein the anti-Galectin-9 antibody is administered concurrently with a checkpoint inhibitor. In some embodiments, wherein the anti-Galectin-9 antibody is administered before or after a checkpoint inhibitor. In some embodiments, the checkpoint inhibitor is administered systemically. In some embodiments, the checkpoint inhibitor is administered locally.

In some embodiments, the methods are provided, wherein the administered anti-Galectin-9 antibody, such as any of the Galectin-9 antibodies described herein in Table 1 and/or Table 2, such as 9.2-17 or 9.1-8mut13, is capable of improving anti-tumor activity (e.g., reduced tumor proliferation, size, volume, weight, burden or load, reduction in number of metastatic lesions over time) of the co-administered checkpoint inhibitors (e.g., PD-1, PD-L1 and/or CTLA-4 or others listed herein or known in the art), e.g., by 10%, 20%, 25%, 30%, 40%, 50%, 60%, 70%, 75%, 80%, 85%, 90%, 95%, or more as compared to a checkpoint inhibitor therapy alone under the same conditions. In some embodiments, the administered anti-Galectin-9 antibody, such as any of the Galectin-9 antibodies described herein in Table 1 and/or Table 2, for example antibody 9.2-17 or antibody 9.1-8mut13, is capable of improving antitumor activity (e.g., tumor proliferation, size, volume, weight, load or burden, or reduction in number of metastatic lesions over time) of the co-administered checkpoint inhibitors (e.g., PD-land/or CTLA-4 e.g., PD-1, PD-L1 and/or CTLA-4 or others listed herein or known in the art), e.g., 1.0-1.2-fold, 1.2-1.4-fold, 1.4-1.6-fold, 1.6-1.8-fold, 1.8-2-fold, or two-fold more or more as compared to a checkpoint inhibitor therapy alone under the same conditions. In some embodiments, the administered anti-Galectin-9 antibody, such as any of the Galectin-9 antibodies described herein in Table 1 and/or Table 2, including but not limited to antibody 9.1-8m13 and/or antibody 9.2-17, is capable of improving antitumor activity (e.g., tumor proliferation, size, volume, weight, load or burden or reduction in number of metastatic lesions over time) of the co-administered checkpoint inhibitor (e.g., PD-1, PD-L1 and/or CTLA-4 or others listed herein or known in the art), e.g., about three-fold, four-fold, about threefold, four-fold, five-fold, six-fold, seven-fold, eight-fold, nine-fold, ten-fold, or more as compared to a checkpoint inhibitor therapy alone under the same conditions. In some embodiments, the co-administered checkpoint inhibitors (e.g., PD-1, PD-L1 and/or CTLA-4 or others listed herein or known in the art) are capable of improving anti-tumor activity of the administered anti-Galectin-9 antibody, such as any of the Galectin-9 antibodies described herein in Table 1 and/or Table 2, including but not limited to antibody 9.1-8m13 and/or antibody 9.2-17, (e.g., tumor proliferation, size, volume, weight, burden or load or reduction in number of metastatic lesions), e.g., by 10%, 20%, 25%, 30%, 40%, 50%, 60%, 70%, 75%, 80%, 85%, 90%, 95%, or more as compared to anti-Galectin-9 therapy alone under the same conditions. In some embodiments, the co-administered checkpoint inhibitors (e.g., PD-1, PD-L1 and/or CTLA-4 or others listed herein or known in the art) are capable of improving antitumor activity (e.g., tumor proliferation, size, volume, weight, load or burden or reduction in number of metastatic lesions over time) of the administered anti-Galectin-9 antibody, such as any of the Galectin-9 antibodies described herein in Table 1 and/or Table 2, including but not limited to antibody 9.1-8m13 and/or antibody 9.2-17, e.g., 1.0-1.2-fold, 1.2-1.4-fold, 1.4-1.6-fold, 1.6-1.8-fold, 1.8-2-fold, or two-fold more or more as compared to an anti-Galectin-9 therapy alone under the same conditions. In some embodiments, the co-administered checkpoint inhibitors (e.g., PD-1, PD-L1 and/or CTLA-4 or others described herein or known in the art) are capable of improving antitumor activity (e.g., tumor proliferation, size, volume, weight, load or burden or reduction in number of metastatic lesions over time) of the anti-Galectin-9 antibody, such as any of the Galectin-9 antibodies described herein in Table 1 and/or Table 2, including but not limited to, antibody 9.1-8m13 and/or antibody 9.2-17, e.g., about three-fold, four-fold, about threefold, four-fold, five-fold, six-fold, seven-fold, eight-fold, nine-fold, ten-fold, or more as compared to a anti-Galectin-9 therapy alone under the same conditions.

In some embodiments, the methods are provided, wherein the administered anti-Galectin-9 antibody, such as any of the Galectin-9 antibodies described herein in Table 1 and/or Table 2, including but not limited to, antibody 9.1-8m13 and/or antibody 9.2-17, is capable of improving the ability of the immunotherapy to activate T cells (e.g., as measured by cytokine markers described herein) (e.g., as described herein or known in the art), e.g., by 10%, 20%, 25%, 30%, 40%, 50%, 60%, 70%, 75%, 80%, 85%, 90%, 95%, or more as compared to a immunotherapy therapy alone under the same conditions. In some embodiments, the administered anti-Galectin-9 antibody is capable of improving the ability of the immunotherapy to activate T cells (e.g., as measured by cytokine markers described herein) (e.g., as described herein or known in the art), e.g., 1.0-1.2-fold, 1.2-1.4-fold, 1.4-1.6-fold, 1.6-1.8-fold, 1.8-2-fold, or two-fold more or more as compared to a immunotherapy therapy alone under the same conditions. In some embodiments, the administered anti-Galectin-9 antibody, such as any of the Galectin-9 antibodies described herein in Table 1 and/or Table 2, including but not limited to, antibody 9.1-8m13 and/or antibody 9.2-17, is capable of improving the ability of the immunotherapy to activate T cells (e.g., as measured by cytokine markers described herein) (e.g., as described herein or known in the art), e.g., about three-fold, four-fold, about threefold, four-fold, five-fold, six-fold, seven-fold, eight-fold, nine-fold, ten-fold, or more as compared to a immunotherapy therapy alone under the same conditions.

In some embodiments, the methods are provided, wherein the co-administered immunotherapies (e.g., as described herein or known in the art) are capable of improving the ability of the anti-Galectin-9 antibody, such as any of the Galectin-9 antibodies described herein in Table 1 and/or Table 2, including but not limited to, antibody 9.1-8m13 and/or antibody 9.2-17, to activate T cells (e.g., as measured by cytokine markers described herein), e.g., by 10%, 20%, 25%, 30%, 40%, 50%, 60%, 70%, 75%, 80%, 85%, 90%, 95%, or more as compared to an anti-Galectin-9 therapy alone under the same conditions. In some embodiments, the co-administered immunotherapies (e.g., as described herein or known in the art) are capable of improving the ability of the anti-Galectin-9 antibody to activate T cells (e.g., as measured by cytokine markers described herein), e.g., 1.0-1.2-fold, 1.2-1.4-fold, 1.4-1.6-fold, 1.6-1.8-fold, 1.8-2-fold, or two-fold more or more as compared to an anti-Galectin-9 therapy alone under the same conditions. In some embodiments, the co-administered immunotherapies (e.g., as described herein or known in the art) are capable of improving the ability of the anti-Galectin-9 antibody to activate T cells (e.g., as measured by cytokine markers described herein), e.g., about three-fold, four-fold, about threefold, four-fold, five-fold, six-fold, seven-fold, eight-fold, nine-fold, ten-fold, or more as compared to an anti-Galectin-9 therapy alone under the same conditions.

In other embodiments, the methods are provided herein, wherein the anti-Galectin-9 antibody, such as any of the Galectin-9 antibodies described herein in Table 1 and/or Table 2, including but not limited to, antibody 9.1-8m13 and/or antibody 9.2-17, is administered in combination with one or more of the existing modalities for treating autoimmune disorders including, but not limited to: intravenous Ig therapy, nonsteroidal anti-inflammatory drugs (NSAID), and corticosteroids; and anti-inflammatory treatments such as cyclosporins, rapamycins or ascomycins, or their immunosuppressive analogs, e.g., cyclosporin A, cyclosporin G, FK-506, rapamycin, 40-O-(2-hydroxy)ethyl-rapamycin etc.; cyclophosphamide; azathioprene; methotrexate; brequinar; FTY 720; leflunomide; mnizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; or other immunomodulatory compounds, e.g., CTLA4Ig, or other adhesion molecule inhibitors, e.g. mAbs or low molecular weight inhibitors including selectin antagonists and VLA-4 antagonists. These combination therapies can be part of an immunomodulating regimens or a regimen for the treatment or prevention of inflammatory disorders or autoimmune disorders.

In some embodiments, the methods are provided, wherein the anti-Galectin-9 antibody, such as any of the Galectin-9 antibodies described herein in Table 1 and/or Table 2, including but not limited to, antibody 9.1-8m13 and/or antibody 9.2-17, can also be co-used with a chemotherapeutic agent, including alkylating agents, anthracyclines, cytoskeletal disruptors (Taxanes), epothilones, histone deacetylase inhibitors, inhibitors of topoisomerase I, inhibitors of topoisomerase II, kinase inhibitors, nucleotide analogs and precursor analogs, peptide antibiotics, platinum-based agents, retinoids, vinca alkaloids and derivatives thereof.

Non-limiting examples include: (i) anti-angiogenic agents (e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000)); (ii) a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof, and (iii) chemotherapeutic compounds such as, e.g., pyrimidine analogs (5-fluorouracil, floxuridine, capecitabine, gemcitabine and cytarabine), purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones, and navelbine, epidipodophyllotoxins (etoposide and teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycin, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, mitoxantrone, topotecan, and irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

In some embodiments, methods are provided herein wherein the anti-Galectin-9 antibody, such as any of the Galectin-9 antibodies described herein in Table 1 and/or Table 2, including but not limited to, antibody 9.1-8m13 and/or antibody 9.2-17, is administered concurrently with a chemotherapeutic agent. In some embodiments, methods are provided herein, wherein the anti-Galectin-9 antibody is administered before or after a chemotherapeutic agent. In some embodiments, methods are provided herein, wherein the chemotherapeutic agent is administered systemically. In some embodiments, methods are provided herein, wherein the chemotherapeutic agent is administered locally.

In some embodiments, the methods are provided, wherein the anti-Galectin-9 antibody, such as any of the antibodies described herein in Table 1 and/or Table 2, for example antibody 9.2-17 or antibody 9.1-8mut13, is capable of improving anti-tumor activity (e.g., tumor proliferation, size, volume, weight, burden load or reduction in number of metastatic lesions over time) of the co-administered chemotherapeutic agents (e.g., as described herein or known in the art), e.g., by 10%, 20%, 25%, 30%, 40%, 50%, 60%, 70%, 75%, 80%, 85%, 90%, 95%, or more as compared to a chemotherapeutic agent therapy alone under the same conditions. In some embodiments, the anti-Galectin-9 antibody is capable of improving antitumor activity (e.g., tumor proliferation, size, volume, weight, load or burden or reduction in number of metastatic lesions over time) of the co-administered chemotherapeutic agents (e.g., as described herein or known in the art), e.g., 1.0-1.2-fold, 1.2-1.4-fold, 1.4-1.6-fold, 1.6-1.8-fold, 1.8-2-fold, or two-fold more or more as compared to a chemotherapeutic agent therapy alone under the same conditions. In some embodiments, the anti-Galectin-9 antibody is capable of improving antitumor activity (e.g., tumor proliferation, size, volume, weight, load or burden or reduction in number of metastatic lesions over time) of the co-administered chemotherapeutic agent (e.g., as described herein or known in the art), e.g., about three-fold, four-fold, about threefold, four-fold, five-fold, six-fold, seven-fold, eight-fold, nine-fold, ten-fold, or more as compared to a chemotherapeutic agent therapy alone under the same conditions.

In some embodiments, the methods are provided, wherein the co-administered chemotherapeutic agents (e.g., as described herein or known in the art) are capable of improving anti-tumor activity of the anti-Galectin-9 antibody, such as any of the antibodies described herein in Table 1 and/or Table 2, for example antibody 9.2-17 or antibody 9.1-8mut13, (e.g., tumor proliferation, size, volume, weight, burden or load or reduction in number of metastatic lesions over time) of, e.g., by 10%, 20%, 25%, 30%, 40%, 50%, 60%, 70%, 75%, 80%, 85%, 90%, 95%, or more as compared to an anti-Galectin-9 therapy alone under the same conditions. In some embodiments, the co-administered chemotherapeutic agents (e.g., as described herein or known in the art) are capable of improving anti-tumor activity (e.g., tumor proliferation, size, volume, weight, burden or load or reduction in number of metastatic lesions over time) of the anti-Galectin-9 antibody, e.g., 1.0-1.2-fold, 1.2-1.4-fold, 1.4-1.6-fold, 1.6-1.8-fold, 1.8-2-fold, or two-fold more or more as compared to an anti-Galectin-9 therapy alone under the same conditions. In some embodiments, the co-administered chemotherapeutic agents (e.g., as described herein or known in the art) are capable of improving antitumor activity (e.g., tumor proliferation, size, volume, weight, load or burden or reduction in number of metastatic lesions over time) of the anti-Galectin-9 antibody, e.g., about three-fold, four-fold, about threefold, four-fold, five-fold, six-fold, seven-fold, eight-fold, nine-fold, ten-fold, or more as compared to an anti-Galectin-9 therapy alone under the same conditions.

In some embodiments methods are provided herein, wherein the anti-Galectin-9 antibody, such as any of the antibodies described herein in Table 1 and/or Table 2, for example antibody 9.2-17 or antibody 9.1-8mut13, is capable of improving the ability of the chemotherapeutic agent to activate T cells (e.g., as measured by cytokine markers described herein) (e.g., as described herein or known in the art), e.g., by 10%, 20%, 25%, 30%, 40%, 50%, 60%, 70%, 75%, 80%, 85%, 90%, 95%, or more as compared to a chemotherapeutic agent therapy alone under the same conditions. In some embodiments, the anti-Galectin-9 antibody is capable of improving the ability of the chemotherapeutic agent to activate T cells (e.g., as measured by cytokine markers described herein) (e.g., as described herein or known in the art), e.g., 1.0-1.2-fold, 1.2-1.4-fold, 1.4-1.6-fold, 1.6-1.8-fold, 1.8-2-fold, or two-fold more or more as compared to a chemotherapeutic agent therapy alone under the same conditions. In some embodiments, the anti-Galectin-9 antibody is capable of improving the ability of the chemotherapeutic agent to activate T cells (e.g., as measured by cytokine markers described herein) (e.g., as described herein or known in the art), e.g., about three-fold, four-fold, about threefold, four-fold, five-fold, six-fold, seven-fold, eight-fold, nine-fold, ten-fold, or more as compared to a chemotherapeutic agent therapy alone under the same conditions.

In some embodiments, methods are provided herein, wherein the co-administered chemotherapeutic agents (e.g., as described herein or known in the art) are capable of improving the ability of the anti-Galectin-9 antibody, such as any of the antibodies described herein in Table 1 and/or Table 2, for example antibody 9.2-17 or antibody 9.1-8mut13, to activate T cells (e.g., as measured by cytokine markers described herein), e.g., by 10%, 20%, 25%, 30%, 40%, 50%, 60%, 70%, 75%, 80%, 85%, 90%, 95%, or more as compared to an anti-Galectin-9 therapy alone under the same conditions. In some embodiments, the co-administered chemotherapeutic agents (e.g., as described herein or known in the art) are capable of improving the ability of the anti-Galectin-9 antibody to activate T cells (e.g., as measured by cytokine markers described herein), e.g., 1.0-1.2-fold, 1.2-1.4-fold, 1.4-1.6-fold, 1.6-1.8-fold, 1.8-2-fold, or two-fold more or more as compared to an anti-Galectin-9 therapy alone under the same conditions. In some embodiments, the co-administered chemotherapeutic agents (e.g., as described herein or known in the art) are capable of improving the ability of the anti-Galectin-9 antibody to activate T cells (e.g., as measured by cytokine markers described herein), e.g., about three-fold, four-fold, about threefold, four-fold, five-fold, six-fold, seven-fold, eight-fold, nine-fold, ten-fold, or more as compared to an anti-Galectin-9 therapy alone under the same conditions.

Kits for Use in Modulating Immune Responses

The present disclosure also provides kits for use in modulating (e.g., enhancing immune responses) in a subject, e.g., a human patient having a solid tumor, an autoimmune disease, or a disease caused by microbial infection. Such kits can include one or more containers comprising an anti-Galectin-9 antibody, e.g., any of those described herein, and optionally a second therapeutic agent to be co-used with the anti-Galectin-9 antibody, which is also described herein. In some embodiments, the second therapeutic agent is a checkpoint inhibitor such as an anti-PD-1 antibody.

In some embodiments, the kit can comprise instructions for use in accordance with any of the methods described herein. The included instructions can comprise a description of administration of the anti-Galectin-9 antibody, and optionally the second therapeutic agent, to modulate (e.g., increase) immune responses in a subject as described herein. The kit may further comprise a description of selecting an individual suitable for treatment based on identifying whether that individual has the target disease, e.g., applying the diagnostic method as described herein. In still other embodiments, the instructions comprise a description of administering an antibody to an individual at risk of the target disease.

The instructions relating to the use of an anti-Galectin-9 antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for modulating (e.g., increasing) one or more immune responses in the subject, e.g., those described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-Galectin-9 antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Generation of Anti-Galectin-9 Antibodies

Codon-optimized genes encoding human Galectin-9 CRD1 (residues 1-148; SEQ ID NO: 3) and mouse Galectin-9 CRD1 (residues 1-147; SEQ ID NO: 5) were cloned as GST fusions using the pGEX vector including thrombin cleavage site and Avitag upstream of the cloned gene. Human Galectin-9 CRD2 (residues 218-355; SEQ ID NO: 4) and mouse Galectin-9 CRD2 (residues 226-353; SEQ ID NO: 6) were cloned into the pHBT vector, an IPTG inducible expression vector that contains a hexahistadine tag, Avitag and TEV cleavage site upstream of the cloned gene (Sha et al., *Proc Natl Acad Sci USA,* 2013, 110: 14924-14929). Human and mouse Galectin-9 CRD2 samples were then purified via Ni-Sepharose columns followed by gel filtration to apparent homogeneity and biotinylated in vitro using recombinant BirA. Human and mouse Galectin-9 CRD1 samples were purified via GST affinity chromatography followed by thrombin cleavage. Samples were further purified using gel filtration chromatography and biotinylated in a similar manner to Galectin-9 CRD2. Recombinant full-length mouse Galectin-9 (R&D Systems) was used as a control where necessary.

Antibody clones capable of binding to the human or mouse Galectin-9 fragments as noted above were isolated from a phage-display Fab library. The library follows the design of highly successful "Library E" (Miller et al., *PloS One,* 2012, 7, e43746) with improvements. A total of four rounds of phage library sorting were performed using CRD1 and CRD2 samples as the targets, essentially following published procedures (Miller et al., *PloS One,* 2012, 7, e43746; Fellouse et al., *J Mol Biol,* 2007, 373, 924-940). For CRD2, selection campaigns were performed using (a) only either mouse or human CRD2 as the target or (b) using human and mouse CRD2 samples alternately in successive rounds of library sorting. For CRD1, only human CRD1 samples were used.

Binding to Galectin-9 CRDs was determined by phage ELISA (Sidhu et al., *Methods Enzymol,* 2000, 328, 333-363). Biotinylated CRD samples were immobilized to neutravidin-coated wells and blocked with an excess of biotin. The wells were incubated with phage displaying single Fab clones and then bound phages were detected with HRP-conjugated anti-M13 phage antibody.

Then, phage-displayed Fab clones were pre-incubated with 50 nM non-biotinylated Galectin-9 CRD2 or CRD1 prior to addition to ELISA plates. Reduction in the ELISA signal of clones with competitor compared to those without competitor indicated a high affinity and high specificity for Galectin-9 CRD1 or CRD2.

The genes for a subset of identified antibody clones were transferred into an *E. coli* expression vector that has previously been described (Zhang et al., *Proc Natl Acad Sci USA,* 2012, 109, 8534-8539). Fab proteins were expressed in *E. coli* BL21 (EMD Millipore) and purified using HiTrap Protein G HP column (GE Healthcare) as described (Hattori et al., *Nat Methods,* 2013, 10, 992-995) followed by Superdex S200 or ResourceS column (GE Healthcare). When required, purified Fab was biotinylated via the Avitag attached to the C-terminus of the heavy chain using BirA.

Antibodies in the human IgG1, human IgG4, mouse IgG1 and mouse IgG2a formats were produced by cloning the genes for the $V_H$ and $V_L$ regions into mammalian expression vectors for IgG production (Invivogen). Accordingly, mIgG1 and mIgG2a are human/mouse hybrids, because the Fc (i.e. CH2 and CH2) is mouse IgG1, whereas CH1 and CL are human. The proteins were produced by transient transfection of ExpiCHO cells (ThermoFisher) and purified using Protein G Sepharose chromatography followed by Superdex S200 or ResourceS chromatography (GE Healthcare).

For further characterization, one clone, G9.2-1 (a human IgG4 molecule) was screened for CRD specificity. Biotinylated Galectin-9 CRD1 or CRD2 was immobilized onto streptavidin-coated magnetic beads. The beads were blocked with excess biotin, followed by titration of the G9.2-17 human IgG4 antibody. The beads were then stained and quantified via flow cytometry. The results are presented in FIG. 14, and show that the antibody is specific for CRD2 relative to CRD1, and does not bind CRD1 to a significant extent.

Example 2: Characterization of Anti-Galectin-9 Antibody Clones

Epitope Binning

Whether the antibody clones bind to distinct (non-overlapping) epitopes in Galectin-9 was examined using competition phage ELISA. The binding of all the CRD2-binding clones were significantly inhibited by pre-incubation of the purified G9.2-1, G9.2-3, G9.2-15 or G9.2-17 Fab clone (FIGS. 13A and 13B), indicating that the isolated clones bind to an overlapping epitope within CRD2. Clones G9.2-15 and G9.2-17 were selected as representative clones for further characterization because of their strong binding activity and good cross-reactivity between human and mouse Galectin-9.

Epitope Mapping

Figure 2A:
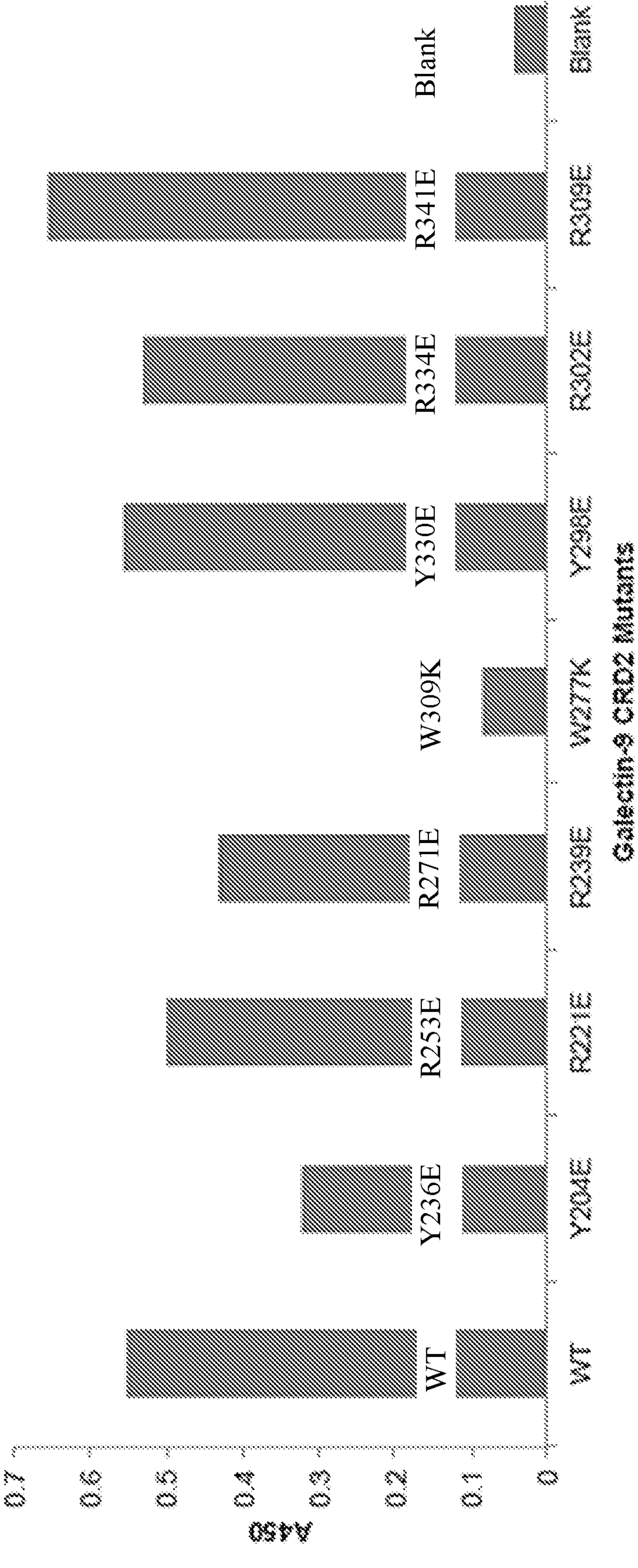
FIGS. 2A-2B include diagrams showing epitope mapping of G.9-2.17 on human Galectin-9 CRD2 by systematic mutagenesis.
Figure 2B:
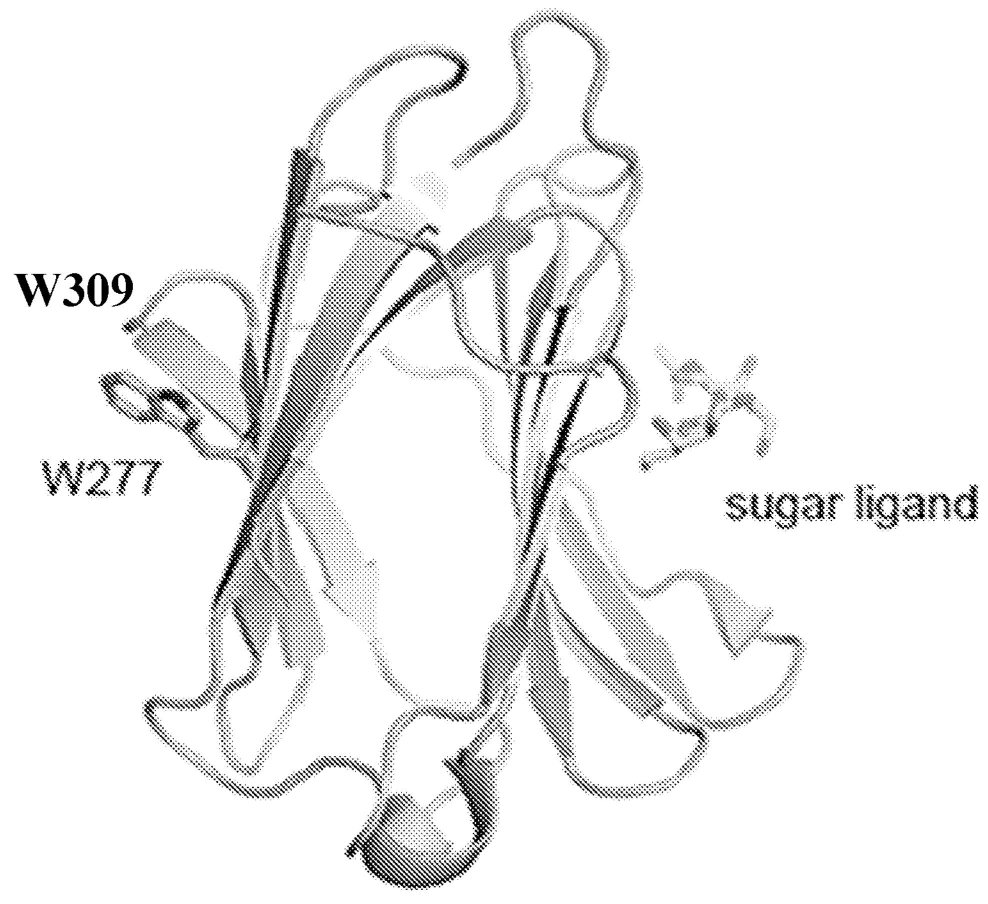

The G9.2-17 clone was selected for further epitope analysis. To determine its epitope on Galectin-9 CRD2, a series of point mutants were constructed. Their ability to bind to G9.2-17 was assayed using phage ELISA, as shown in FIG. 2A. Reductions in ELISA signal indicates sites on Galectin-9 CRD2 that are critical to G9.2-17 binding. Notably, the W309K mutation (residue numbering is according to isoform 1, NCBI GenBank Accession No. BAB83625.1) dramatically reduced the binding, while the other mutations had marginal effects, suggesting that G9.2-17 binds to a region including W309. Crystal structure analysis of the region showed that it is located opposite the sugar-binding site (FIG. 2B). The term “W309” or “residue W309” refers to the tryptophan residue found at position 309 in SEQ ID NO: 1 (Galectin-9) or to the tryptophan residue located at position 277 in the sequence of Galectin-9 isoform 2, UniProt ID 000182-2 or to a residue in CRD2 of Galectin-9 that corresponds to the residue found at position 309 in SEQ ID NO: 1 or at position 277 in the sequence of the isoform of UniProt ID 000182-2. The terms “R253”, “R271”, “R334”, and “R341” refer to the arginine residue found at positions 253, 271, 334, and 341, respectively, in SEQ ID NO: 1 or the arginine residue found at positions 221, 239, 302, 309, respectively, in the sequence of Galectin-9 isoform 2, UniProt ID 000182-2. The terms “Y330” and “Y236” refer to the tyrosine residue found at positions 330 and 236, respectively, in SEQ ID NO: 1 or the tyrosine residue found at positions 298 and 204, respectively, in the sequence of Galectin-9 isoform 2, UniProt ID 000182-2.

Antibodies that Bind to a Distinct Epitope within CRD2

Figure 3:
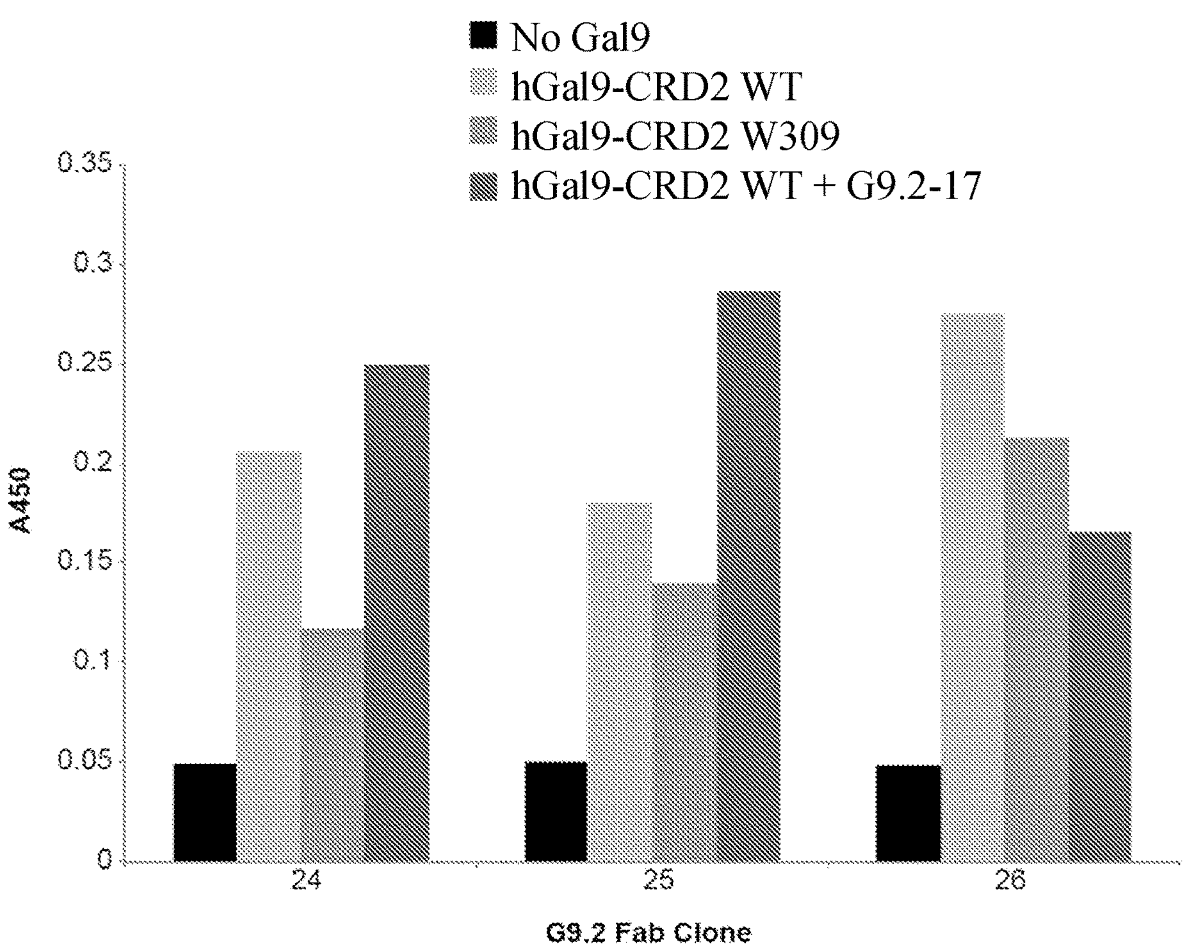
FIG. 3 is a graph showing a binding characterization of G9.2 Fab clone for wild-type Galectin-9 CRD2 or the W3039K mutant using phage ELISA. Binding of Fab clones to human Galectin-9 CRD2 assayed using phage ELISA. Either biotinylated wild type human Galectin-9 CRD2, the W309K Galectin-9 CRD2 mutant, or Galectin-9 CRD2 pre-incubated with G9.2-17 IgG was immobilized to neutravidin-coated wells and incubated with individual phage-displayed Fab clones.

Potential additional epitopes were explored using additional clones that bind to Galectin-9 CRD2. A phage display library selection using a modified scheme so as to enrich clones that bind to an epitope that is distinct from that of G9.2-17 was performed. Wild type human biotinylated Galectin-9 CRD2, the W309K Galectin-9 CRD2 mutant, or Galectin-9 CRD2 preincubated with G9.2-17 IgG was immobilized to neutravidin-coated wells and incubated with individual phage-displayed Fab clones. The results are shown in FIG. 3. Three clones (G9.2-24, G9.2-25, and G9.2-26) exhibited similar levels of binding to the three targets tested, wild-type Galectin-9 CRD2, the W309K mutant, and wild-type CRD2 in complex with G9.2-17. Their binding profiles suggest that they bind to an epitope that is distinct from that of G9.2-17.

Affinity Measurements

The affinities of the antibodies were assessed using a bead-based assay as previously described (Nishikori et al., *J Mol Biol,* 2012, 424, 391-399) and surface plasmon resonance (SPR). In the bead-based assay, a biotinylated protein (either a Galectin-9 sample or a Fab sample) was immobilized on streptavidin-coated Dynabeads M280 via the biotin-streptavidin interaction. After blocking the excess biotin-binding sites on the beads using unconjugated biotin, binding titration was performed by incubating the second component (i.e., Fab for immobilized Galectin-9 or vice versa), followed by quantification using a dye-labeled neutravidin (ThermoFisher) and flow cytometry analysis. In experiments where the second component is an IgG, a dye-labeled anti-human IgG or anti-mouse IgG antibody was used for detection.

Figure 1:
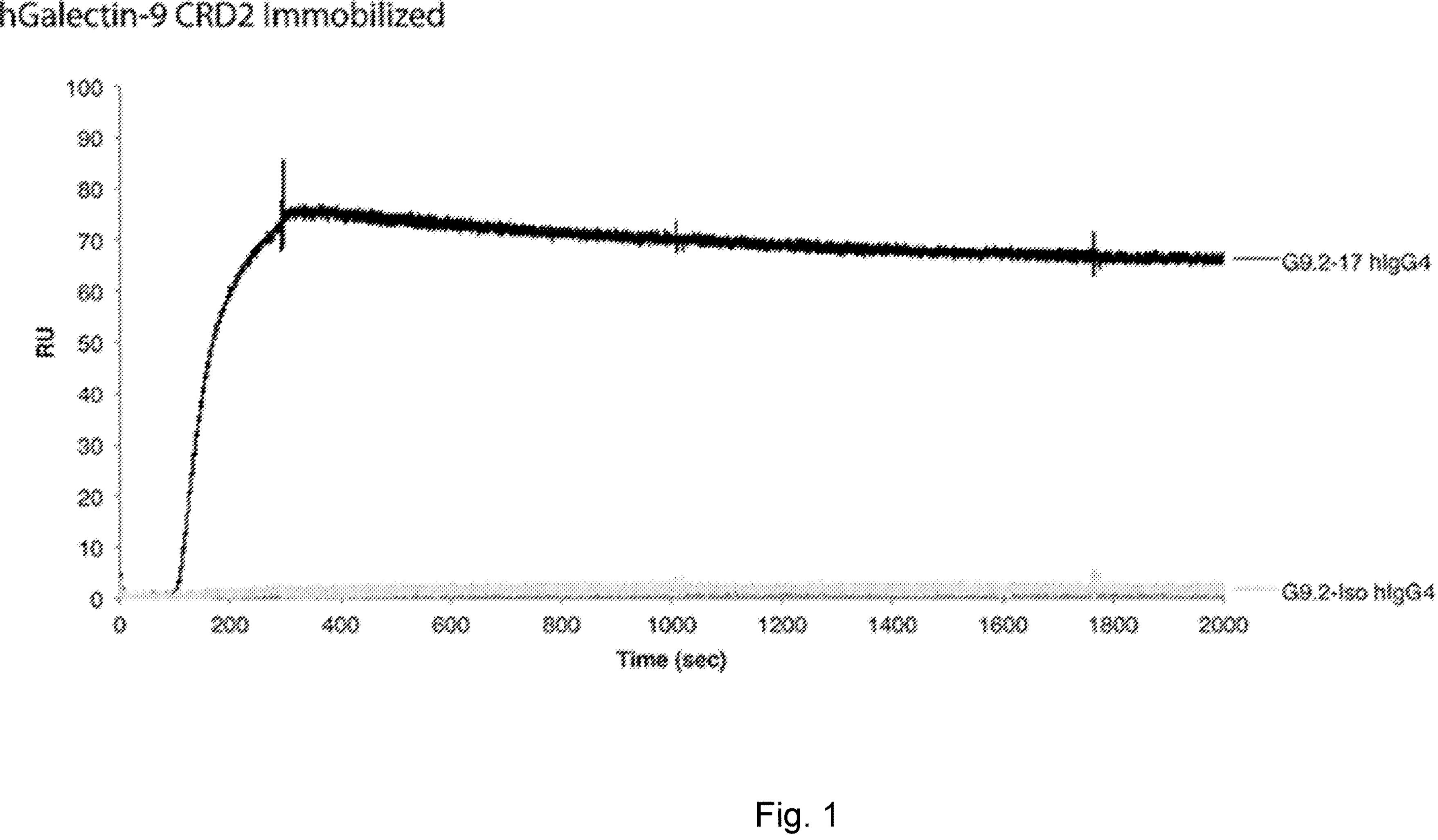
FIG. 1 includes diagrams showing an SPR analysis of G9.2-17 human IgG4 binding to CRD2 of human (top) and mouse (bottom) Galectin-9. The gray lines show the sensorgrams for the non-binding negative control, G9.2-iso human IgG4.
Figure 1:
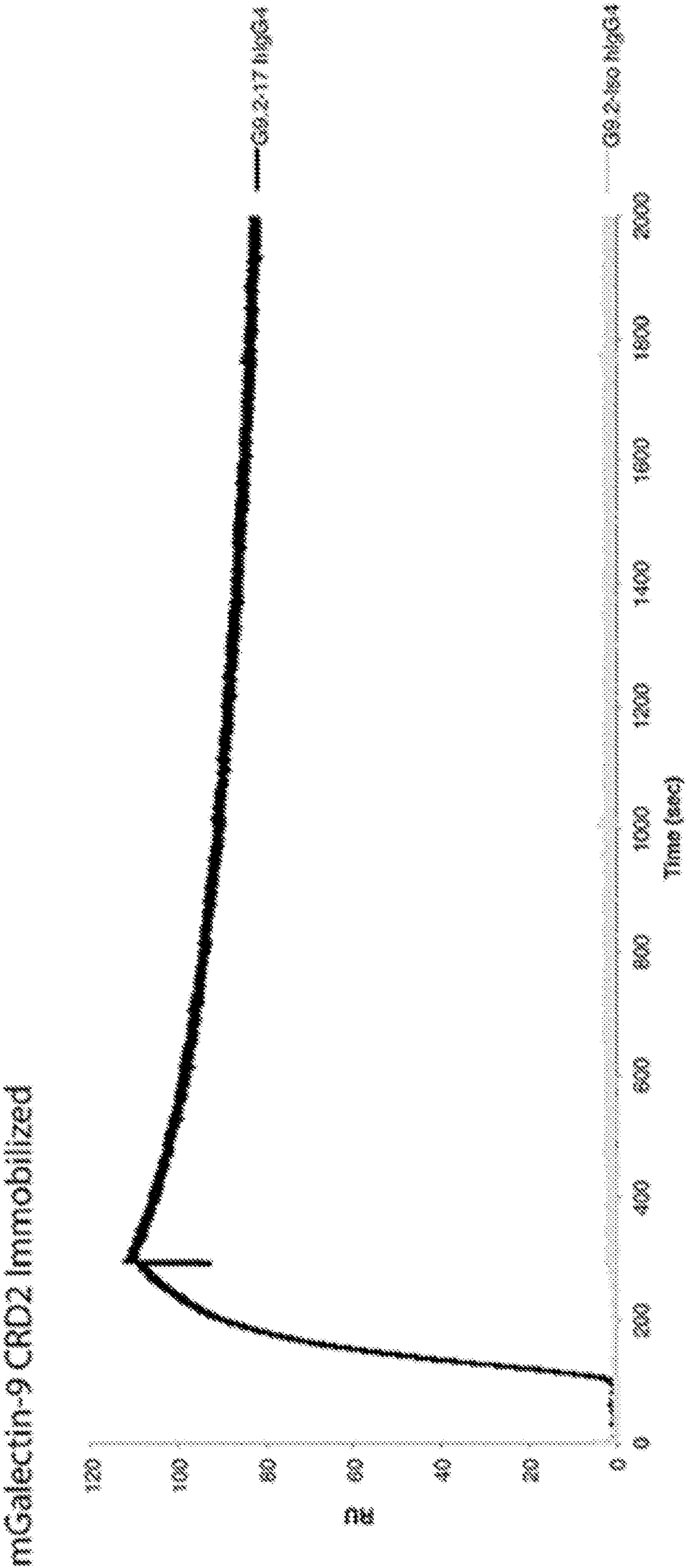

Conversion of G9.2-17 into the human IgG4 format substantially reduced the dissociation rate, as expected from the bivalent nature of IgG4 (FIG. 1). This was demonstrated using the OneStep method described above.

Example 3: Characterization of Clone 9.1-8m13

The binding activity of clone G9.1-8m13 is evaluated using conventional methods. Using a bead-based binding assay, it was determined that the purified G9.1-8m13 Fab has a KD value of 20.7±0.8 nM. Using the same assay, it was determined that the purified G9.1-8m13 mIgG2a molecule has a KD value of 0.30±0.04 nM. These results show that conversion of G9.1-8 mutant clones from the Fab into the IgG2A format can reduce the dissociation rate, as expected from the bivalent nature of IgG.

Example 4: Evaluation of Gal-9 Antibodies Alone or in Combination with Checkpoint Inhibition in a Mouse Model of Pancreatic Cancer and Tumor Mass and Immune Profile of Mice Treated with G9.2-17 mIgG1

The effect of G9.2-17 mIgG1 on tumor weight and on immune profile was assessed in a mouse model of pancreatic cancer. 8-week old C57BL/6 male (Jackson Laboratory, Bar Harbor, ME) mice were administered intra-pancreatic injections of FC1242 PDA cells derived from Pdx1Cre; KrasG12D; Trp53R172H (KPC) mice (Zambirinis C P, et al., TLR9 ligation in pancreatic stellate cells promotes tumorigenesis. J Exp Med. 2015; 212:2077-94). Tumor cells were suspended in PBS with 50% Matrigel (BD Biosciences, Franklin Lakes, NJ) and $1\times10^5$ tumor cells were injected into the body of the pancreas via laparotomy. Mice (n=10/group) received one pre-treatment dose i.p. followed by 3 doses (q.w.) of commercial αGalectin 9 mAb (RG9-1, 200 μg, BioXcell, Lebanon, NH) or G9.2-17 mIgG1 (200 μg), or paired isotype, either G9.2-Iso or rat IgG2a (LTF-2, BioXcell, Lebanon, NH) (200 μg) (one dose per week for three weeks). Mice were sacrificed 3 weeks later and tumors were harvested for analyses by flow cytometry.

Tumor Mass of Mice Treated with G9.2-17 mIgG1

The effect of G9.2-17 mIgG1 on tumor weight was assessed in a mouse model of pancreatic cancer. 8 to 10 week-old C57BL/6 mice were orthotopically implanted with KPC ($Pdx1^{Cre}$; $Kras^{G12D}$; $Tp53^{R172H}$)-derived FC1242 pancreatic cancer cells. On day 0, one day prior to treatment, the mice were administered an isotype antibody (100 μg) or G9.2-17 mIgG1 antibody (20 μg, 50 μg, or 100 μg) intraperitoneally. Mice were then administered the same treatment on days 4, 8, 12, 16, and 20. On day 21, the mice were sacrificed and tumor mass was determined. Administration of the G9.2-17 mIgG1 antibody reduced tumor mass relative to the untreated and isotype groups (n=10 mice/group). At the higher doses of G9.2-17 mIgG1 antibody, 50 μg and 100 μg, the reduction was statistically significant ($p<0.05$ and $p<0.0001$, respectively).

Figure 4:
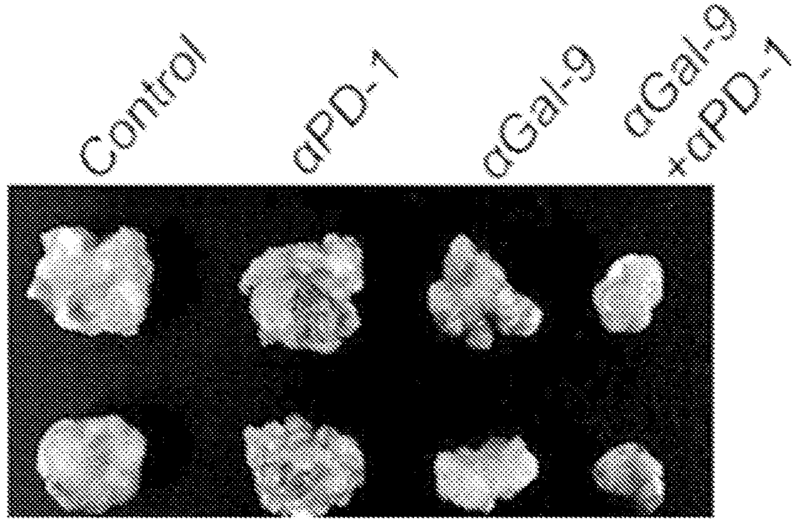
FIG. 4 is a photograph of mouse tumors showing that blocking galectin-9 and anti-PD1 generates a superior response.
Figure 5A:
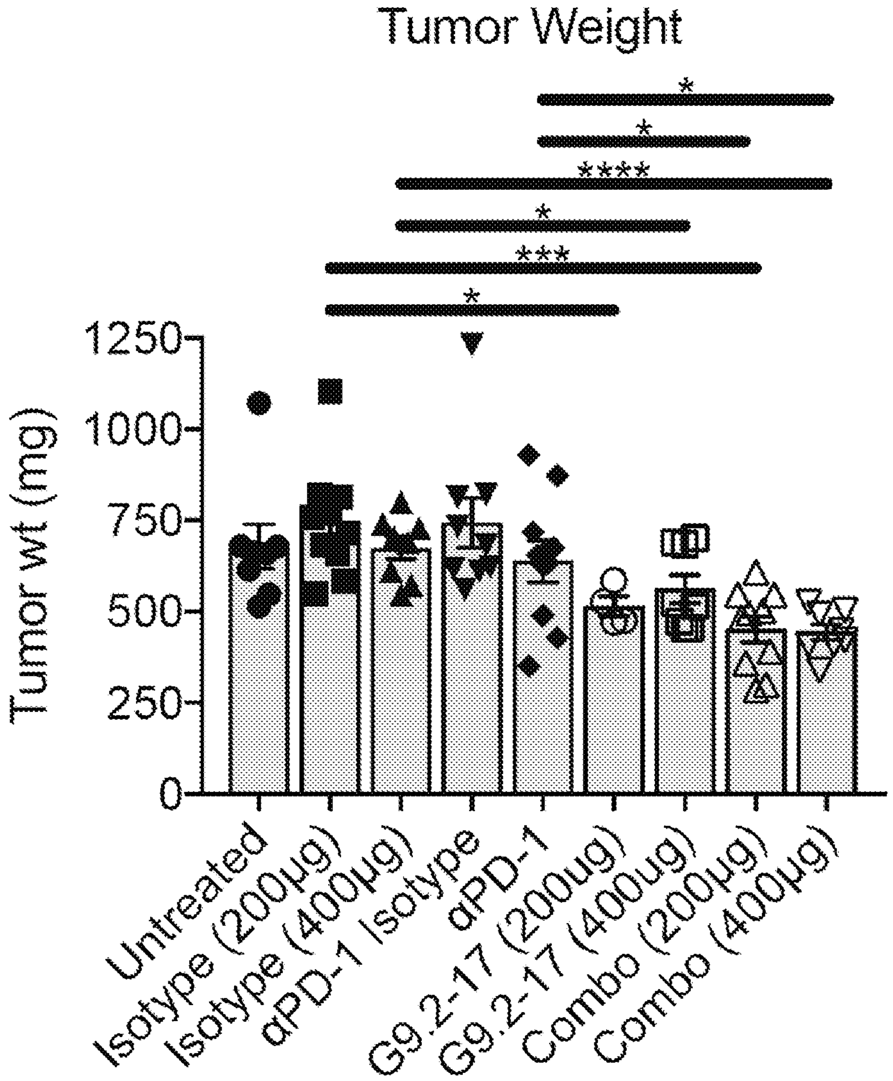
FIGS. 5A-5C depicts a bar graph showing tumor weight of mice treated with G9.2-17 mIgG2a alone or in combination with αPD1 mAb. Mice (n=10/group) with orthotopically implanted KPC tumors were treated with commercial αPD-1 (200 μg) mAb or G9.2-17 mIg2a (200 μg), or a combination of G9.2-17 and αPD-1, or matched isotype once weekly for three weeks. Tumors were removed and weighed and subsequently processed and stained for flow cytometry. Each point represents one mouse; *p<0.05; p<0.01; *p<0.001; ****p<0.0001; by unpaired Student's t-test.
Figure 5B:
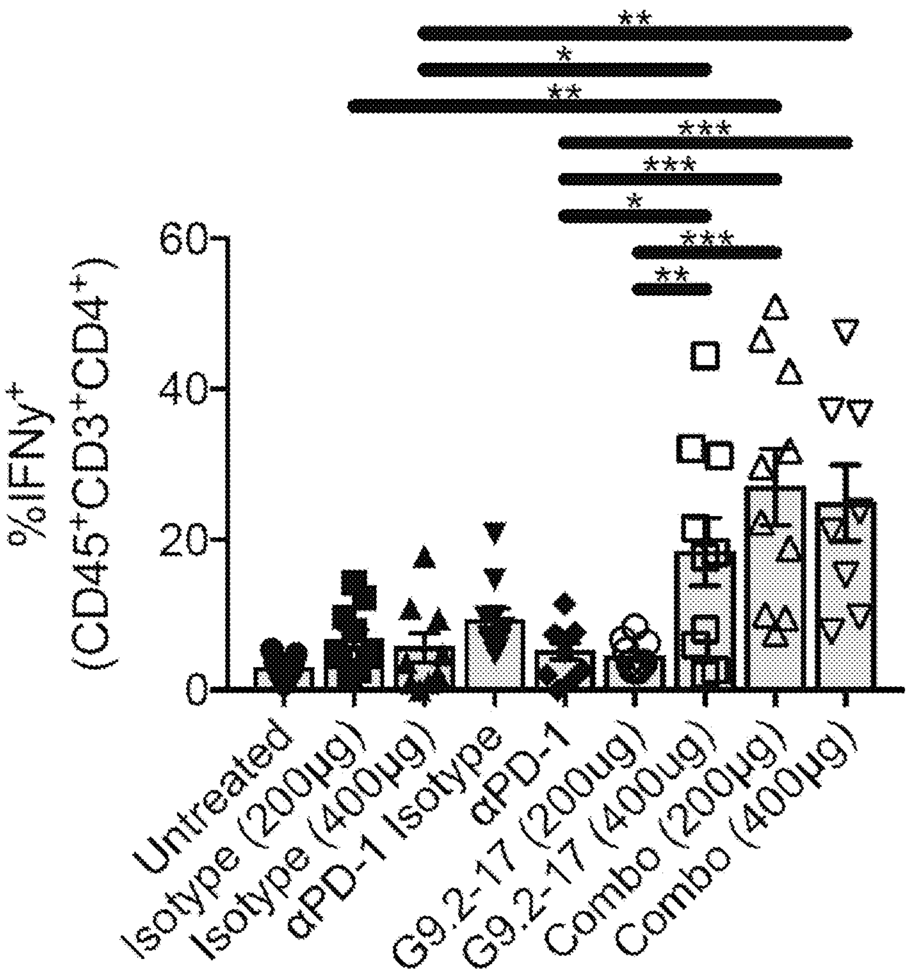
Figure 5C:
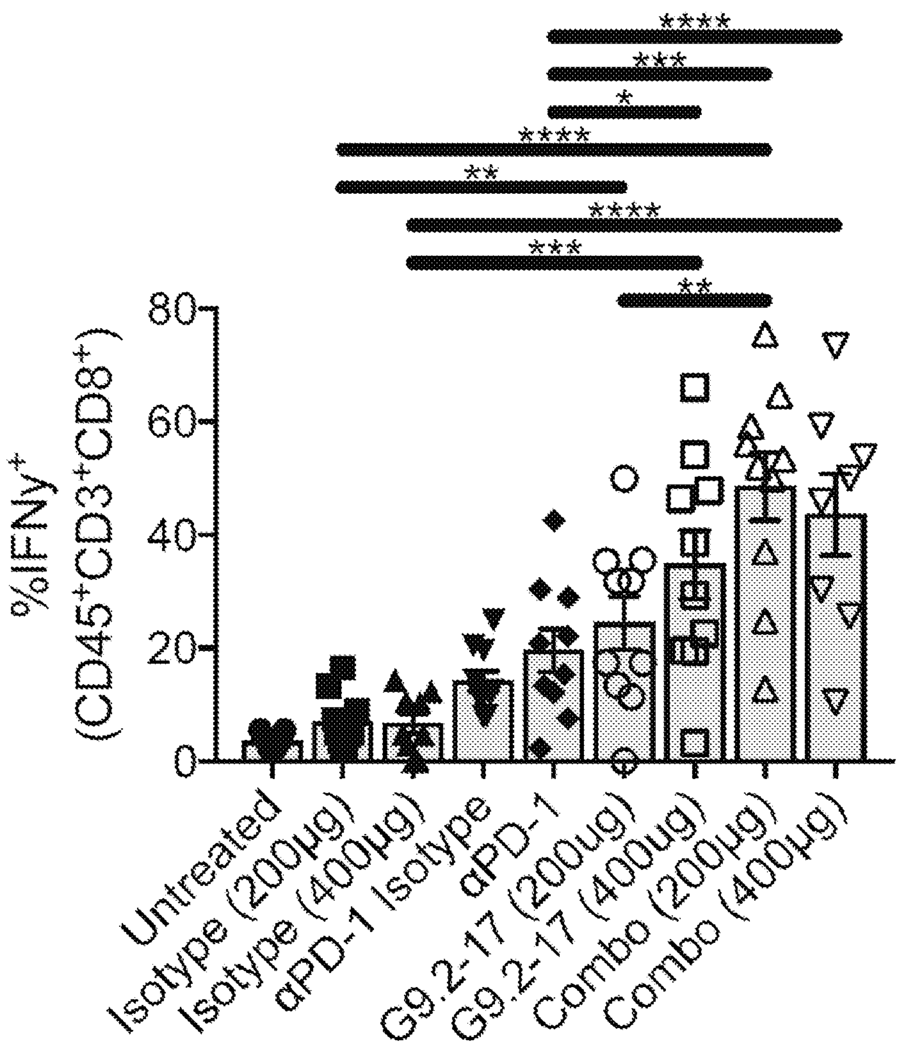
Figure 6A:
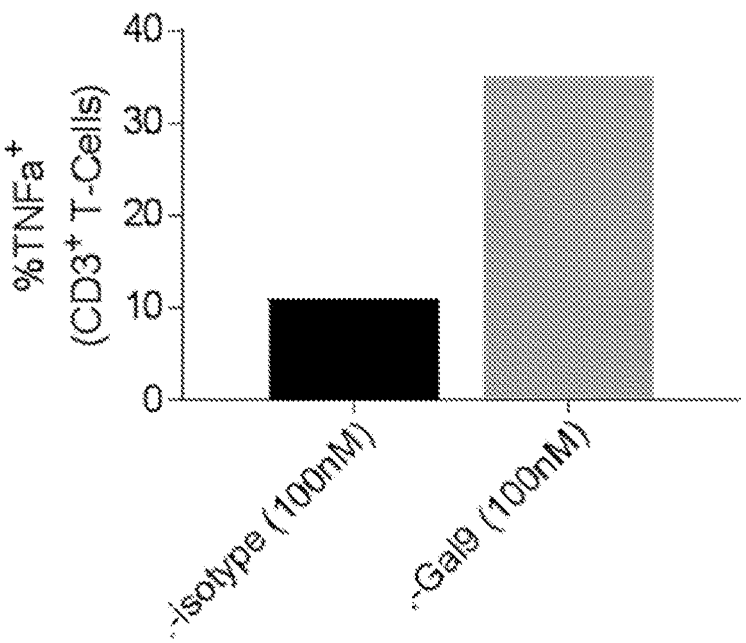
FIGS. 6A and 6B depict bar graphs showing TNF-alpha (FIG. 6A) and IFN-gamma (FIG. 6B) expression in CD3+ T cells in pancreatic adenocarcinoma primary tumor sample patient-derived organotypic tumor spheroids (PDOTs) treated with 9.2-17 IgG4 (100 nM) as compared to isotype control (100 nM).
Figure 6B:
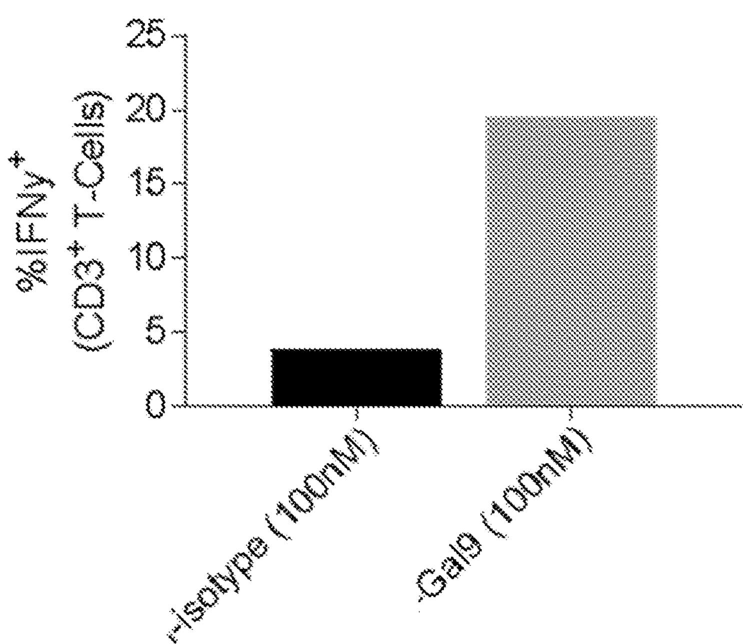
Figure 7A:
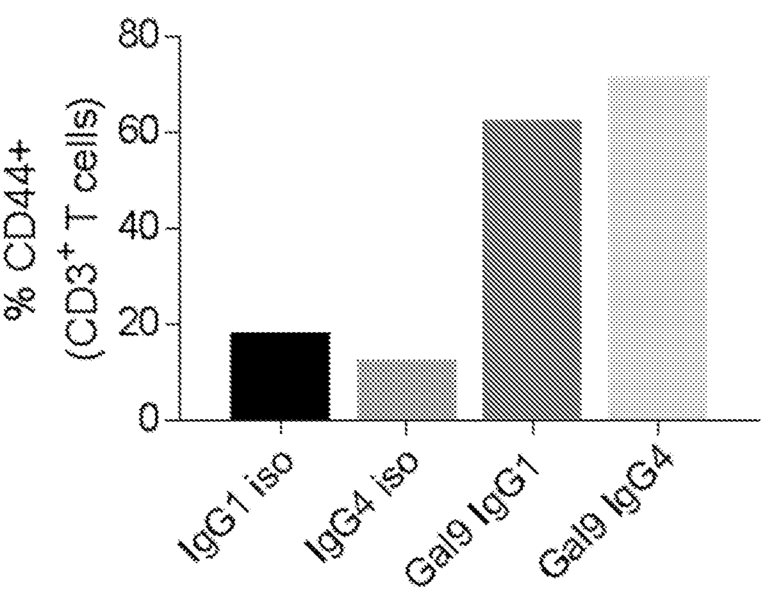
FIGS. 7A-7C depict bar graphs showing CD44 (FIG. 7A), TNF-alpha (FIG. 7B) and IFN-gamma (FIG. 7C) expression in CD3+ T cells in pancreatic adenocarcinoma primary tumor sample patient-derived organotypic tumor spheroids (PDOTS) treated with 9.2-17 IgG1 (100 nM) or 9.2-17 IgG4 (100 nM) as compared to IgG1 or IgG4 isotype control (100 nM).
Figure 7B:
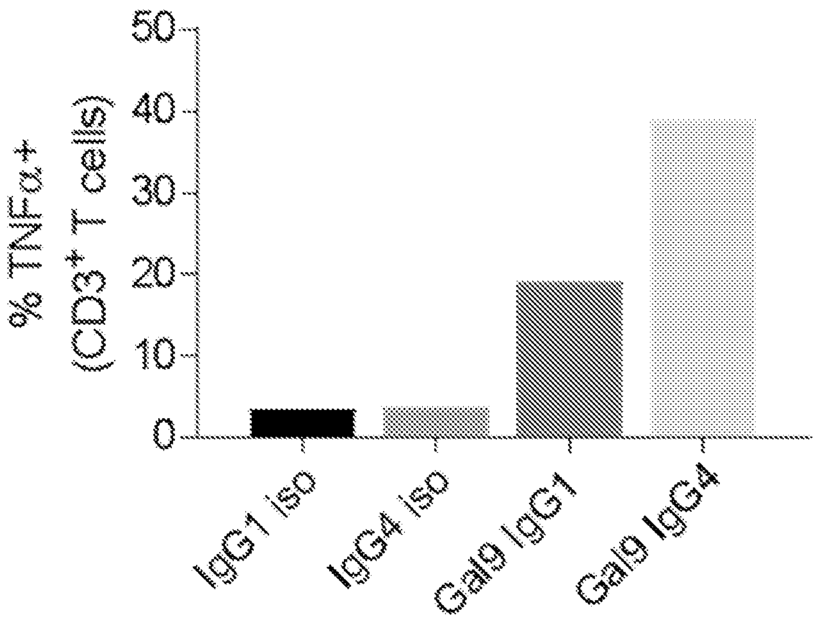
Figure 7C:
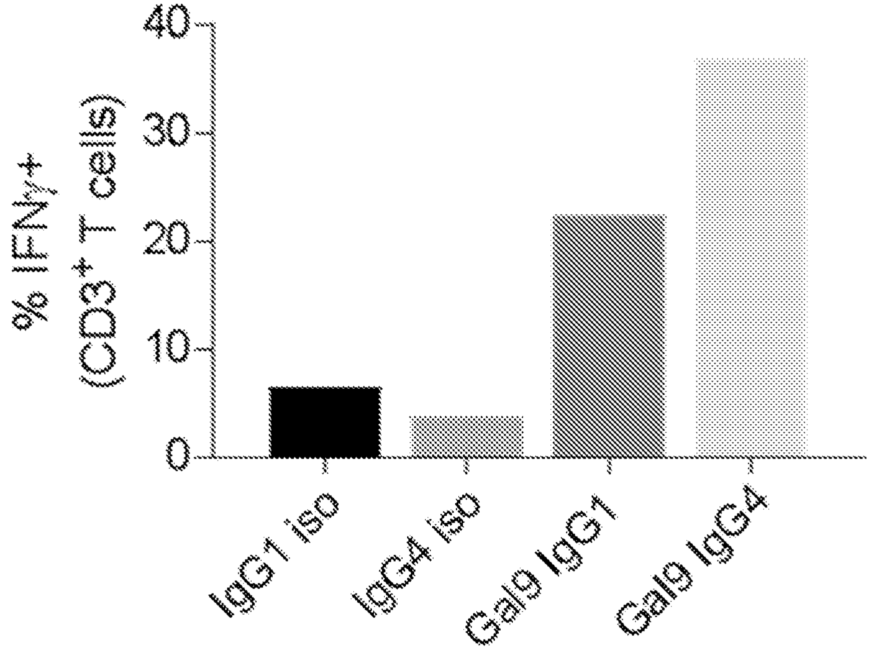
Figure 8A:
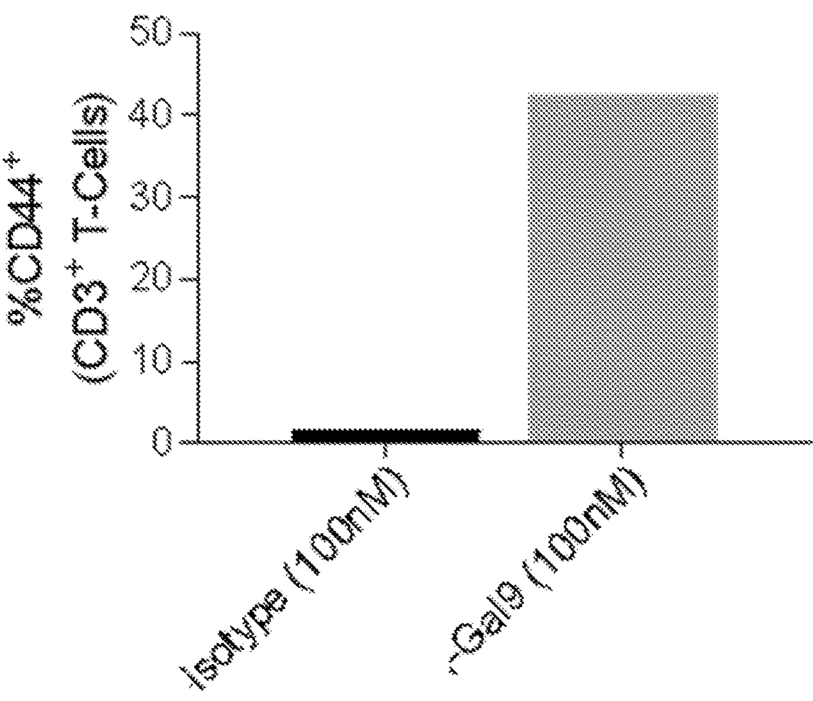
FIGS. 8A-8F depict bar graphs showing immune profile expression in a Gall Bladder Cancer tumor sample (PDOTS) treated with G9.2-17 IgG4 (100 nM) as compared to IgG4 isotype control (100 nM) for CD44 in CD3+ T cells (FIG. 8A), TNF-alpha in CD3+ T cells (FIG. 8B), CD44 in CD4+ T cells (FIG. 8C), TNF-alpha in CD4+ T cells (FIG. 8D), CD44 in CD8+ T cells (FIG. 8E), and TNF-alpha in CD8+ T cells (FIG. 8F).
Figure 8B:
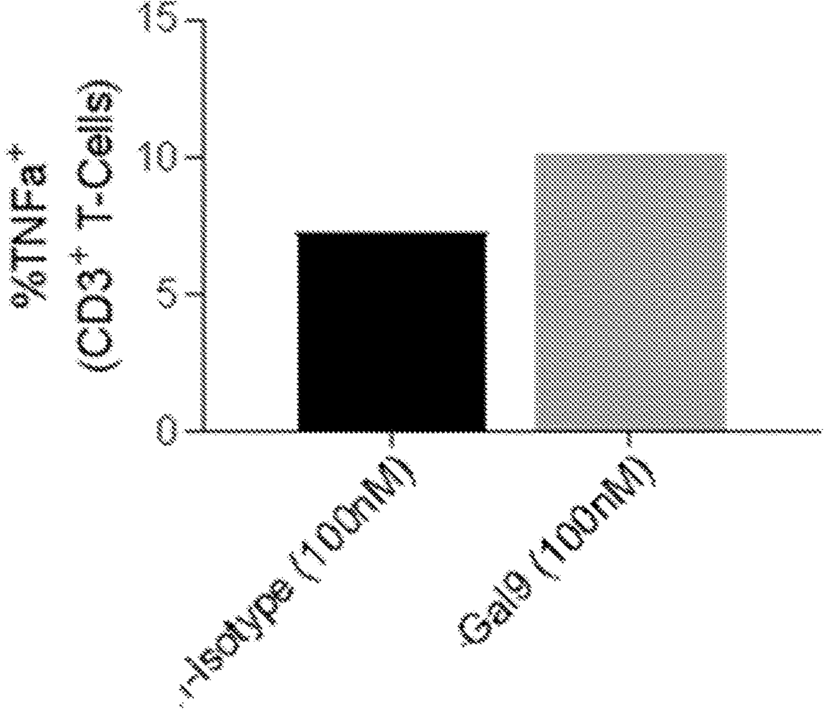
Figure 8C:
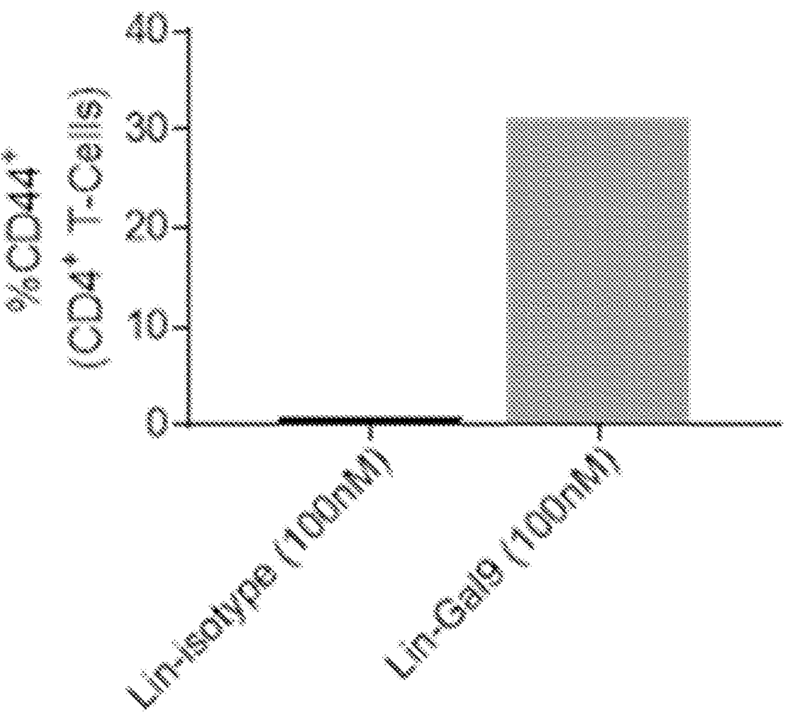
Figure 8D:
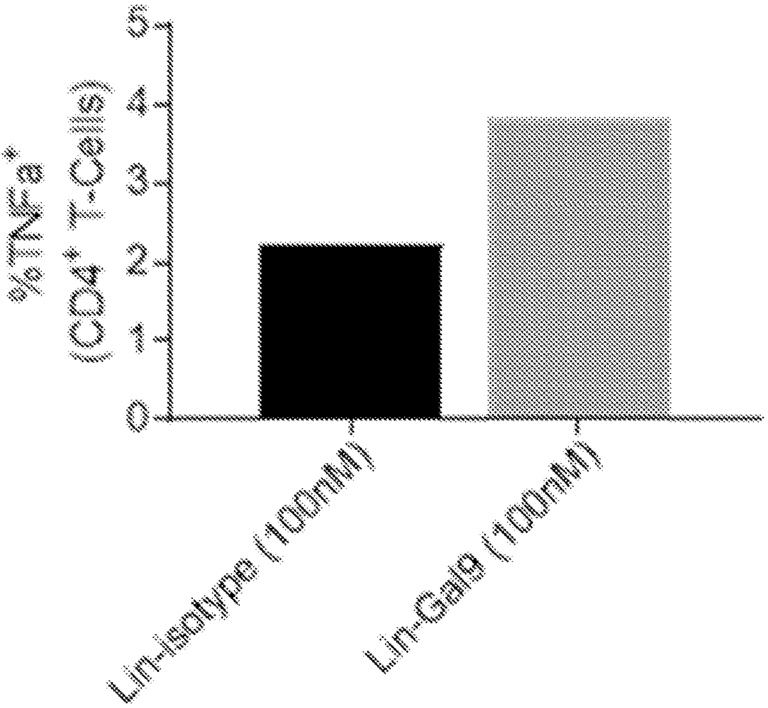
Figure 8E:
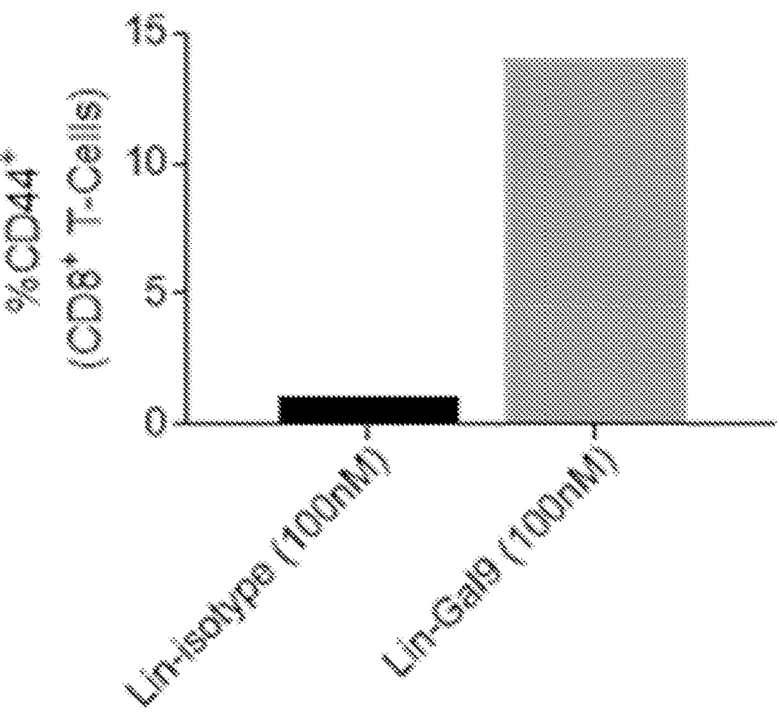
Figure 8F:
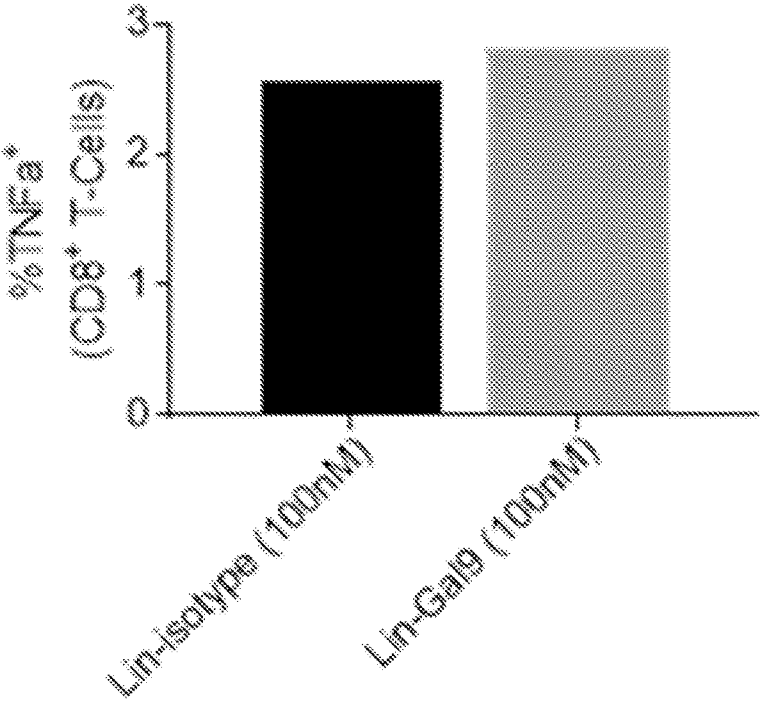

Tumor Mass and Immune Profile of Mice Treated with G9.2-17 mIgG2a Alone or in Combination with αPD1 mAb The effect of G9.2-17 mIgG2a on tumor weight and on immune profile was assessed in a mouse model of pancreatic cancer, alone or in combination with immunotherapy. 8-week old C57BL/6 male mice (Jackson Laboratory, Bar Harbor, ME) were administered intra-pancreatic injections of FC1242 PDA cells derived from Pdx1Cre; KrasG12D; Trp53R172H (KPC) mice. Tumor cells were suspended in PBS with 50% Matrigel (BD Biosciences, Franklin Lakes, NJ) and 1×105 tumor cells were injected into the body of the pancreas via laparotomy. Mice received one pre-treatment dose i.p. followed by 3 doses (q.w.) of G9.2-17 mIgG2a (200 μg) or a neutralizing αPD-1 mAb (29F.1A12, 200 μg, BioXcell, Lebanon, NH), separately or in combination, or paired isotype (LTF-2 and C1.18.4, BioXcell, Lebanon, NH) as indicated. Mice were sacrificed on day 26 and tumors were harvested for analyses as shown in FIG. 4. Tissue was processed and prepared and flow cytometry analysis was performed as described in Example 5. Results are shown in FIGS. 5A-5C. Each point represents one mouse; $*p<0.05$; $p<0.01$; $*p<0.001$; $****p<0.0001$; by unpaired Student's t-test. These results show single-agent treatment with G9.2-17 mIgG2a reduces tumor growth at both of the dose levels, whereas anti-PD-1 alone had no effect on tumor size.

Example 5: Spheroid Preparation and Analysis of Effect of Anti-Gal9 Antibody in Tumor Spheroids Derived from Patient Samples Patient-derived organotypic tumor spheroids (PDOTS) were prepared from fresh patient tumor specimens (pancreatic adenocarcinoma, gall bladder cancer, and liver metastasis from a colorectal cancer). Briefly, specimens were received in media on ice and minced in 10 cm dishes and resuspended in DMEM+10% FBS+100 U/mL collagenase type IV. Partially digested samples were pelleted, re-suspended, and strained over both 100 μm and 40 μm filters to generate S1 (>100 μm), S2 (40-100 μm), and S3 (<40 μm) spheroid fractions, which were subsequently maintained in low-attachment tissue culture plates. An aliquot of the S2 fraction was pelleted and resuspended in type I rat tail collagen at a concentration of 2.5 mg/mL following addition of 10×PBS with phenol red with pH adjusted using NaOH. The spheroid-collagen mixture was injected into the center gel region of the DAX-1 3D microfluidic cell culture chip. After 30 minutes at 37° C., collagen hydrogels containing PDOTS were hydrated with media and treated with Gal9 antibody (G9.2-17). Three days later, PDOTS were harvested and were flowed for immune changes. Representative results on single patient samples are shown in FIGS. 6A, 6B, 7A-7C, 8A-F, and 9A-9C. If more than 100 cells were obtained, then cells were sorted for CD3+, CD4+ and CD8+, otherwise cells were only sorted for CD3+. As shown in Table 4 below and in FIG. 20, 16 PDOTS were treated. "Responders" were PDOTS that showed an increase of greater than 20% in response compared to the isotype control in two out of three markers (CD44, TNFα, and IFNγ).

TABLE 4

| Summary of PDOTS Data | | |
|---|---|---|
| Cancer Type | Cases | Responders |
| Colorectal Carcinoma | 4 | 2 |
| Gall Bladder | 1 | 1 |
| CRC Liver Metastasis | 8 | 5 |
| Pancreatic | 3 | 2 |
| Total | 16 | 10 |

Example 6: Evaluation of CRD2 Clone 17 IgG1 and IgG4 Human Galectin 9 Monoclonal Antibodies in a Model of Acute Myeloid Leukemia (AML) in Humanized Mice A study is conducted to evaluate CRD2 clone 17 IgG1 and IgG4 human Galectin 9 monoclonal antibodies in a model of Acute Myeloid Leukemia in humanized mice (CTG-2243, Champions). The study protocol is depicted in Table 5.

TABLE 5

| AML Efficacy Study Design: | | | | |
|---|---|---|---|---|
| Group | -n- | Agent | Dose (μg/dose) | ROA/Schedule |
| 1 | 10 | Vehicle Control | — | p.o./qwx4 |
| 2 | 10 | Control IgG1/4 | 100 | p.o./qwx4 |
| 3 | 10 | Control IgG1/4 | 200 | p.o./qwx4 |
| 4 | 10 | Control IgG1/4 | 400 | p.o./qwx4 |
| 5 | 10 | Anti-Gal9 1/4 | 100 | p.o./qwx4 |
| 6 | 10 | Anti-Gal9 1/4 | 200 | p.o./qwx4 |
| 7 | 10 | Anti-Gal9 1/4 | 400 | p.o./qwx4 |
| 8 | 10 | Cytarabine | 50 | QDx5 |
| 9 | 10 | Cytarabine vehicle | — | QDx5 |

Study Animal Preparation

Animals are sublethally irradiated and reconstituted with 1-5 million primary AML cells via tail vein injection. In-life blood collection is performed once monthly and flow cytometry is conducted using the following flow panel: huCD45/muCD45/huCD3/huCD33 for determination of engraftment. Once human CD33+ levels reach 20-1000 counts/μl, 6 surrogate animals are euthanized for comprehensive immunophenotyping and spleen, bone marrow and peripheral blood is analyzed by the flow panel above. Animals are randomized into treatment groups based on peripheral blood counts. Disseminated Tumor growth/burden analysis is conducted up to 42 days dosing and observation. Terminal half whole blood is processed and analyzed for immune parameters and serum is used for Gal9 ELISA.

Terminal blood and bone marrow is collected for flow cytometry. 8-color cell surface flow cytometry is performed from terminal bone marrow and peripheral blood from all animals: The flow panels are: LD/huCD45/huCD3/huCD33/huGalectin9/huTim9/huPD1/huCD34/huCD38/huCD117.

Fresh fecal samples are collected from all animals (1 pellet/mouse) in a polypropylene tube at baseline (prior to treatment initiation), at the end of Week 1 of treatment, and at study endpoint. The collected samples are snap frozen and stored at −80° C. A terminal blood sample and tissues described is collected to assess drug toxicity.

Data Analysis

To assess animal toxicity, beginning on Day 0, animals are observed daily and weighed 3× weekly using a digital scale; data including individual and mean gram weights (Mean We±SEM), mean percent weight change versus Day 0 (% $vD_0$) are recorded for each group and % $vD_0$ is plotted at study completion. Any animal deaths are recorded daily and designated as drug-related (D), technical (T), tumor-related (B), or unknown (U) based on weight loss and gross observation; single agent or combination groups reporting a mean % $vD_0$>20% and/or >10% mortality are considered above the maximum tolerated dose (MTD) for that treatment on the evaluated regimen. Maximum mean % $vD_0$ (weight nadir) for each treatment group is reported at study completion. To assess efficacy of the Gal-9 antibody, tumor growth inhibition is measured. Beginning on Day 0, tumor dimensions are measured 3× weekly by digital caliper and data, including individual and mean estimated tumor volumes (Mean TV±SEM), are recorded for each group; tumor volume (TV) is calculated using the formula $$TV = \text{width}^2 \times \text{length} \times 0.52.$$

At study completion, percent tumor growth inhibition (% TGI) values are calculated and reported for each treatment group (T) versus control (C) using initial (i) and final (f) tumor measurements by the formula $$\%TGI = 1 - (T_f - T_i)/(C_f - C_i).$$

Individual mice reporting a tumor volume ≤30% of the Day 0 measurement for two consecutive measurements are considered partial responders (PR). Individual mice lacking palpable tumors (0.00 $mm^3$ for two consecutive measurements) are classified as complete responders (CR); a CR that persists until study completion is considered a tumor-free survivor (TFS). Tumor doubling time (DT) is determined for the vehicle treated groups using the formula $$DT = (D_f - D_i) * \log^2/(\log TV_f - \log TV_i) \text{ where } D = \text{Day and } TV = \text{Tumor Volume.}$$

All data collected in this study is managed electronically and stored on a redundant server system.

Example 7: Evaluation of Gal-9 Antibody in a B16F10 Melanoma Syngeneic Tumor Model in Immunocompetent Mice Gal-9 antibody G9.2-17 was evaluated in the B16F10 syngeneic mouse model of melanoma immunocompetent mice. Pre-study animals (female C57BL/6, 6-8 weeks of age (Charles River Labs)) were unilaterally implanted subcutaneously on the left flank with 5e5 B16.F10 in 100 µl PBS. Pre-study tumor volumes were recorded for each experiment beginning 2-3 days after implantation. When tumors reached an average tumor volume of 50-100 $mm^3$ (preferably 50-75 $mm^3$) animals were matched by tumor volume into treatment or control groups (n=8) to be used for dosing and dosing was initiated on Day 0. Animals were dosed on day 0 and day 4 i.v. The study design for testing of Anti-Gal9 G9.2-17 IgG1 and Anti-Gal9 G9.2-17 IgG2 is summarized in Table 6 and Table 7.

TABLE 6

| Anti-Gal9 IgG1 | | | | | |
|---|---|---|---|---|---|
| Group | -n- | Test Agent | Dose (µg/mouse) | Dose Volume | Route of Administration (ROA) |
| 1 | 8 | Control Untreated | — | — | — |
| 2 | 8 | Control mIgG1 | 200 µg | 200 µl | IV |
| 7 | 8 | Anti-Gal9 mIgG1 (G9.2-17) | 200 µg | 200 µl | IV |

TABLE 7

| Anti-Gal9 IgG2 | | | | | | | |
|---|---|---|---|---|---|---|---|
| Group | -n- | Test Agent | Dose (ng/mouse) | Dose Volume | Route of Administration (ROA) | Schedule | Total Number of Doses |
| 1 | 10 | Control Untreated | — | — | — | — | — |
| 2 | 10 | Control mIgG2 | 200 µg | 200 µl | IV | Q4Dx6 | 6 |
| 3 | 10 | Control mIgG2 | 200 µg | 200 µl | IP | BIWx4 | 8 |
| 4 | 10 | Anti-Gal9 mIgG2 (G9.2-17) | 200 µg | 200 µl | IV | Q4Dx6 | 6 |

Tumor volumes were taken and animals were weighed three times weekly. The study endpoint was set when the mean tumor volume of the control group (uncensored) reached 1500 mm3. A final tumor volume was taken on the day the study reached endpoint. A final weight was taken on the day the study reached end point (day 10). Tumor volume is shown in FIG. 10 and FIG. 11. See also FIG. 23A. Flow cytometry was conducted as described in Example 8 and % CD8+ T cells, % CD44 and % TNFalpha in CD3+ cells is shown in FIGS. 23B, 24A, and 24B.

Example 8: Evaluation of Gal-9 Antibody in Two Syngeneic Models of Colorectal and Melanoma Cancer in Immunocompetent Mice Gal-9 antibodies G9.2-17 and G9.1-8m13 are evaluated in syngeneic models of colorectal and melanoma cancer in immunocompetent mice. Test articles are formulated and prepared on a weekly basis for the duration of the study according to Table 8.

TABLE 8

| Test articles | | | | | |
|---|---|---|---|---|---|
| Agent | Master Stock Storage | Master Stock Stability | State | Working Stock Storage | Working Stock Stability |
| Control mIgG1 | 4° C., Dark | For the duration of study | Liquid | 4° C., Dark | For the duration of study |
| Control mIgG2 | 4° C., Dark | For the duration of study | Liquid | 4° C., Dark | For the duration of study |
| Gal9-IgG1 (G9.2-17) | −80° C. | For the duration of study | Liquid | −20° C. | For the duration of study |
| Gal9-IgG2 (G9.2-17) | −80° C. | For the duration of study | Liquid | −20° C. | For the duration of study |
| Gal9-IgG1 (G9.1-8m13) | −80° C. | For the duration of study | Liquid | −20° C. | For the duration of study |
| mGal9-IgG2 (G9.1-8m13) | −80° C. | For the duration of study | Liquid | −20° C. | For the duration of study |
| anti-mPD-1 | 4° C., Dark | For the duration of study | Liquid | 4° C., Dark | For the duration of study |

Vehicle Control: mGal9-IgG1, and mGal9-IgG2; Control mIgG1, Control mIgG2, and anti-mPD-1: Sterile PBS Vehicle Control: mGal9-IgG1, and mGal9-IgG2; Control mIgG1, Control mIgG2, and anti-mPD-1: Sterile PBS Experimental Design Pre-study animals (female C57BL/6, 6-8 weeks of age (Charles River Labs) are acclimatized for 3 days and then are unilaterally implanted subcutaneously on the left flank with 5e5 B16.F10 (melanoma cell line) or MC38 cells (colorectal cancer cell line) resuspended in 100 μl PBS. Pre-study tumor volumes are recorded for each experiment beginning 2-3 days after implantation. When tumors reach an average tumor volume of 50-100 $m^{m3}$ (preferably 50-75 $mm^3$) animals are matched by tumor volume into treatment or control groups to be used for dosing and dosing initiated on Day 0. The study design for testing of Anti-Gal9 IgG1 and Anti-Gal9 IgG2 is summarized in Table 9 and Table 10.

TABLE 9

| Anti-Gal9 IgG1 (B16F10 and MC38) | | | | | | | |
|---|---|---|---|---|---|---|---|
| Group | -n- | Test Agent | Dose (μg/mouse) | Dose Volume | Route of Adminitrations (ROA) | Schedule | Total Number of Doses |
| 1 | 8 | Control Untreated | — | — | — | — | — |
| 2 | 8 | Control mIgG1 | 200 μg | 200 μl | IV | Q4Dx6 | 6 |
| 3 | 8 | Control mIgG1 | 400 μg | 200 μl | IV | Q4Dx6 | 6 |
| 4 | 8 | Control mIgG2 | 200 μg | 200 μl | IP | BIWx4 | 8 |
| 5 | 8 | Anti-Ga19 mIgG1 | 200 μg | 200 μl | IV | Q4Dx6 | 6 |
| 6 | 8 | Anti-Ga19 mIgG1 | 400 μg | 200 μl | IV | Q4Dx6 | 6 |
| 7 | 8 | Anti-Ga19 mIgG1 (G9.1-8m13) | 200 μg | 200 μl | IV | Q4Dx6 | 6 |
| 8 | 8 | Anti-Ga19 mIgG1 (G9.1-8m13) | 400 μg | 200 μl | IV | Q4Dx6 | 6 |
| 9 | 8 | Anti-Gal9 mIgG1 + mAnti-PD1 | 200 pg 200 μg | 200 μl 200 μl | IV IP | Q4Dx6 BIWx4 | 6 8 |
| 10 | 8 | Anti-Gal9 mIgG1 + mAnti-PD1 | 400 pg 200 μg | 200 μl 200 μl | IV IP | Q4Dx6 BIWx4 | 6 8 |
| 11 | 8 | Anti-Ga19 mIgG1 (G9.1-8m13) + mAnti-PD1 | 200 pg 200 μg | 200 μl 200 μl | IV IP | Q4Dx6 BIWx4 | 6 8 |
| 12 | 8 | Anti-Ga19 mIgG1 (G9.1-8m13) + mAnti-PD1 | 400 pg 200 μg | 200 μl 200 μl | IV IP | Q4Dx6 BIWx4 | 6 8 |
| 13 | 8 | mAnti-PD1 | 200 μg | 200 μl | IP | BIWx4 | 8 |

TABLE 10

| Anti-Gal9 IgG2 (B16F10 and MC38) | | | | | | | |
|---|---|---|---|---|---|---|---|
| Group | -n- | Test Agent | Dose (μg/mouse) | Dose Volume | Route of Adminitrations (ROA) | Schedule | Total Number of Doses |
| 1 | 10 | Control Untreated | — | — | — | — | — |
| 2 | 10 | Control mIgG2 | 200 μg | 200 μl | IV | Q4Dx6 | 6 |
| 3 | 10 | Control mIgG2 | 400 μg | 200 μl | IV | Q4Dx6 | 6 |
| 4 | 10 | Control mIgG2 | 200 μg | 200 μl | IP | BIWx4 | 8 |
| 5 | 10 | Anti-Ga19 mIgG2 | 200 μg | 200 μl | IV | Q4Dx6 | 6 |
| 6 | 10 | Anti-Ga19 mIgG2 | 400 μg | 200 μl | IV | Q4Dx6 | 6 |
| 5 | 10 | Anti-Ga19 mIgG2 (G9.1-8m13) | 200 μg | 200 μl | IV | Q4Dx6 | 6 |
| 6 | 10 | Anti-Ga19 mIgG2 (G9.1-8m13) | 400 μg | 200 μl | IV | Q4Dx6 | 6 |
| 7 | 10 | Anti-Ga19 mIgG2 +<br>mAnti-PD1 | 200 μg<br>200 μg | 200 μl<br>200 μl | IV<br>IP | Q4Dx6<br>BIWx4 | 6 8 |
| 8 | 10 | Anti-Ga19 mIgG2 +<br>mAnti-PD1 | 400 μg<br>200 μg | 200 μl<br>200 μl | IV IP | Q4Dx6<br>BIWx4 | 6 8 |
| 7 | 10 | Anti-Ga19 mIgG2 (G9.1-8m13) + mAnti-PD1 | 200 μg<br>200 μg | 200 μl<br>200 μl | IV<br>IP | Q4Dx6<br>BIWx4 | 6 8 |
| 8 | 10 | Anti-Ga19 mIgG2 (G9.1-8m13) + mAnti-PD1 | 400 μg<br>200 μg | 200 μl<br>200 μl | IV IP | Q4Dx6<br>BIWx4 | 6 8 |
| 9 | 10 | mAnti-PD1 | 200 μg | 200 μl | IP | BIWx4 | 8 |

Tumor volumes are taken three times weekly. A final tumor volume is taken on the day the study reaches end-point. A final tumor volume is taken if an animal is found moribund. Animals are weighed three times weekly. A final weight is taken on the day the study reaches end point or if animal is found moribund. Animals exhibiting ≥10% weight loss when compared to Day 0 are provided DietGel® ad libitum. Any animal exhibiting >20% net weight loss for a period lasting 7 days or if mice display >30% net weight loss when compared to Day 0 is considered moribund and is euthanized. The study endpoint is set when the mean tumor volume of the control group (uncensored) reaches 1500 mm3. If this occurs before Day 28, treatment groups and individual mice are dosed and measured up to Day 28. If the mean tumor volume of the control group (uncensored) does not reach 1500 mm3 by Day 28, then the endpoint for all animals is the day when the mean tumor volume of the control group (uncensored) reaches 1500 mm3 up to a maximum of Day 60. Blood is collected from all animals from each group. For blood collection, as much blood as possible is collected via a cardiac puncture into $K_2$EDTA tubes (400 l) and serum separator tubes (remaining) under deep anesthesia induced by isoflurane inhalation. The blood collected into $K_2$EDTA tubes is placed on wet ice until used for performing immune panel flow as shown in Table 11.

TABLE 11

| Flow Cytometry Panel 1 | | | |
|---|---|---|---|
| Antibody | Conjugate | Clone | Supplier |
| mCD3 | FITC | 17A2 | BioLegend |
| mCD4 | APC-Fire | RM4-4 | BioLegend |
| mGamma | BV605 | GL3 | BioLegend |
| mCD8 | APC-R700 | 53-6.7 | BioLegend |
| mCD44 | BV786 | IM7 | BioLegend |
| mCD11b | APC | M1/70 | BioLegend |
| mCD45 | BV510 | 30-F11 | BioLegend |
| Live Dead | 7AAD | — | BioLegend |
| mCD62L | PE-Cy7 | MEL-14 | BioLegend |
| mPD-1 | BV711 | 29F.1A12 | BioLegend |

TABLE 11-continued

| Flow Cytometry Panel 1 | | | |
|---|---|---|---|
| Antibody | Conjugate | Clone | Supplier |
| mCTLA4 | PE | UC10-4B9 | BioLegend |
| mCD27 | BV421 | LG.3A10 | BioLegend |

Blood collected into serum separator tubes is allowed to clot at room temperature for at least 15 minutes. Samples are centrifuged at 3500 for 10 minutes at room temperature. The resultant serum is separated, transferred to uniquely labeled clear polypropylene tubes, and frozen immediately over dry ice or in a freezer set to maintain −80° C. until shipment for the bridging ADA assay (shipped within one week).

Tumors from all animals are collected as follows. Tumors less than 400 $mm^3$ in size are snap frozen, placed on dry ice, and stored at −80° C. until used for RT-qPCR analysis. For tumors of 400-500 $mm^3$ in size, whole tumors are collected into MACS media for use in the Flow Panel 10 (shown in Table 12 below). For tumors greater than 500 $mm^3$ in size, a small piece (about 50 $mm^3$) is snap frozen placed on dry ice, and stored at −80° C. for RT-qPCR, and the remaining tumor is collected in MACS media for flow cytometry (as shown in Table 12). For flow cytometry, tumors are placed in MACS media and stored on wet ice until processed. A summary of the flow cytometry analysis performed is shown in Table 12

TABLE 12

| Flow cytometry Panel 2 | | | |
|---|---|---|---|
| Antibody Description | Conjugate | Clone | Supplier |
| mCD3 | FITC | 17A2 | BioLegend |
| mCD4 | APC-Fire | RM4-4 | BioLegend |
| mGamma | BV605 | GL3 | BioLegend |
| mCD8 | APC-R700 | 53-6.7 | BioLegend |
| mCD69 | BV421 | H1.2F3 | BioLegend |

TABLE 12-continued

| Flow cytometry Panel 2 | | | |
|---|---|---|---|
| Antibody Description | Conjugate | Clone | Supplier |
| mCD11b | APC | M1/70 | BioLegend |
| mCD45 | BV510 | 30-F11 | BioLegend |
| Live Dead | 7AAD | — | BioLegend |
| mCD62L | PE-Cy7 | MEL-14 | BioLegend |
| mPD-1 | BV711 | 29F.1A12 | BioLegend |
| mCTLA4 | PE | UC10-4B9 | BioLegend |
| mNk1.1 | BV786 | PK136 | BioLegend |

Spleen, liver, colon, lungs, heart, and kidneys from all animals are retained in 10% neutral buffered formalin (NBF) for 18-24 hours, transferred to 70% ethanol and stored at room temperature. Formalin fixed samples are paraffin embedded.

Example 9: Evaluation of Gal-9 Antibody in a Models of Cholangiocarcinoma

The efficacy of Gal-9 antibody is assessed in a mouse model of cholangiocarcinoma as described in S. Rizvi, et al. (YAP-associated chromosomal instability and cholangiocarcinoma in mice, Oncotarget, 9 (2018) 5892-5905), the contents of which is herein incorporated by reference in its entirety. In this transduction model, in which oncogenes (AKT/YAP) are instilled directly into the biliary tree, tumors arise from the biliary tract in immunocompetent hosts with species-matched tumor microenvironment. Dosing is described in Table 13.

TABLE 13

| Dosing | | | | | | | |
|---|---|---|---|---|---|---|---|
| Group | -n- | Test Agent | Dose (μg/mouse) | Dose Volume | Route of Adminitrations (ROA) | Schedule | Total Number of Doses |
| 1 | 10 | Control Untreated | — | — | — | — | — |
| 2 | 10 | Control mIgG2 | 200 μg | 200 μg | IV | Q4Dx6 | 6 |
| 3 | 10 | Control mIgG2 | 400 μg | 200 μg | IV | Q4Dx6 | 6 |
| 4 | 10 | Control mIgG2 | 200 μg | 200 μg | IP | BIWx4 | 8 |
| 5 | 10 | Anti-Ga19 mIgG2 (G9.2-17) | 200 μg | 200 μg | IV | Q4Dx6 | 6 |
| 6 | 10 | Anti-Ga19 mIgG2 (G9.2-17) | 400 μg | 200 μg | IV | Q4Dx6 | 6 |
| 7 | 10 | Anti-Ga19 mIgG2 (G9.1.8-m13) | 200 μg | 200 μg | IV | Q4Dx6 | 6 |
| 8 | 10 | Anti-Ga19 mIgG2 (G9.1.8-m13) | 400 μg | 200 μg | IV | Q4Dx6 | 6 |

In brief, murine CCA cells (described in S. Rizvi, et al) are harvested and washed in DMEM. Male C57BL/6 mice from Jackson Labs are anesthetized using 1.5-3% isoflurane. Under deep anesthesia, the abdominal cavity is opened by a 1 cm incision below the xiphoid process. A sterile cotton tipped applicator is used to expose the superolateral aspect of the medial lobe of the liver. Using a 27-gauge needle, 40 μL of standard media containing 1×10^6 cells is injected into the lateral aspect of the medial lobe. Cotton tipped applicator is held over the injection site to prevent cell leakage and blood loss. Subsequently, the abdominal wall and skin are closed in separate layers with absorbable chromic 3-0 gut suture material.

Two weeks post implantation, animals are matched by tumor volume into treatment or control groups to be used for dosing and dosing initiated on Day 0. Tumor volumes are measured and animals weighed three times weekly. A final tumor volume and weight is taken on the day the study reaches endpoint (4 weeks or when tumor burden of control becomes 1500 $mm^3$). Blood is collected from all animals from each group.

Example 10: Anti-Galectin-9 Antibody Protects T Cells from Galectin-9 Mediated Apoptosis To investigate actions of anti-Galectin-9 antibody G9.2-17, an apoptosis assay was performed to determine if T cells are dying by the process of apoptosis or by other mechanisms.

In brief, MOLM-13 (human leukemia) cells were cultured in RPMI media supplemented with 10% FBS, 2 mM L-glutamine, 10 mM HEPES, 1 mM sodium pyruvate, 4.5 g/L glucose and 1.5 g/L sodium bicarbonate at 37° C. in 5% $CO_2$. Cells were then transferred into serum-free RPMI media and suspended at a concentration of 2.5e6 cells/mL in serum-free media. Cells were seeded into the wells of a tissue culture grade 96-well plate at a density of 2e5 cells/well (80 μL of cell suspension per well). Monoclonal anti-Galectin-9 antibody or matched isotype was added to each well and incubated at 37° C., 5% $CO_2$ for 30 min. Following this incubation, recombinant, full length human Galectin-9 (R&D Systems 2045-GA, diluted in PBS) was added to a final concentration of 200 nM. Cells were incubated at 37° C., 5% $CO_2$ for 16 hours. Cells were then stained with Annexin V-488 and propidium iodide (PI) prior to analysis by flow cytometry. Each condition was performed in triplicate. PI is impermeant to live cells and apoptotic cells, but stains dead cells with red fluorescence, binding tightly to the nucleic acids in the cell. After staining a cell population with Alexa Fluor® 488 annexin V and PI in buffer, apoptotic cells showed green fluorescence, dead cells showed red and green fluorescence, and live cells showed little or no fluorescence. The cells were distinguished using a flow cytometer with the 488 nm line of an argon-ion laser for excitation. Analysis was then performed on FlowJo software. The fraction of annexin V- and propidium iodide (PI)-positive cells is plotted as a function of antibody concentration used in FIG. 15. As shown in FIG. 15, the level of apoptotic T cells treated with the anti-Gal9 antibody was much lower than T cells treated with a human IgG4 isotype control antibody, indicating that the anti-Galectin-9 antibody G9.2-17 protects T cells against galectin-9 mediated cell apoptosis.

Example 11: Epitope Mapping of Anti-Gal9 Antibody G9.2-17

To determine the epitope of G9.2-17 on galectin-9 CRD2, we first mutated residues in several positions throughout CRD2 including R239, which is crucial for carbohydrate binding (Zhu et al., 2005). Only one mutation, W277K, decreased G9.2-17 binding. Interestingly the R239E mutation had no effect. To further map the binding patch of G9.2-17, residues that are spatially adjacent to W277 were mutated to alanine and their binding was assessed. W277A and L279A result in complete abrogation of G9.2-17 binding in our assay. S208A, L210A and A288S resulted in detectable reduction (FIG. 17). These residues are located adjacent in space in the beta-sheet, and form a patch on the back side of CRD2 relative to its carbohydrate recognition site. These results suggest that the identified residues directly interact with G9.2-17.

The identified residues are highly conserved among galectin-9 from different species (SEQ ID NOs: 49-52), which rationalizes the broad species cross-reactivity of G9.2-17.

| | | |
|---|---|---|
| Human | PSKSILLSGTV | SFSVWILCEAHCLKVAVDGQH |
| Macaque | PSKSITLSGTV | SFSVWILCDAHCLKVAVDGQH |
| Rat | PSKSINISGVV | SFSVWILCEGHCFKVAVDGQH |
| Mouse | PSKSIMISGNV | SFSVWIICEGHCFKVAVNGQH |

(bold: mapped residues; black, identical residues; underline: different residues)

In contrast, these residues are not conserved among human galectins, rationalizing the high specificity of G9.2-17 toward galectin-9 (SEQ ID NOs: 53-60).

| | | |
|---|---|---|
| Gal9 | PSKSILLSGTV | SFSVWILCEAHCLKVAVDGQH |
| Gal1 | PGECLRVRGEV | VAEVCITFDQANLTVKLPDGY |
| Gal2 | PGSTLKITGSI | EVKFTVTFESDKFKVKLPDGH |
| Gal3 | PRMLITILGTV | PFKIQVLVEPDHFKVAVNDAH |
| Gal4 | ARRTIIIKGYV | FFDLSIRCGLDRFKVYANGQH |
| Gal7 | PGTVLRIRGLV | PFEVLIIASDDGFKAVVGDAQ |
| Gal8 | PGRTVVVKGEV | YFEMIIYCDVREFKVAVNGVH |
| Gal10 | TGSTVTIKGRP | EFELSISVLPDKYQVMVNGQS |

Table 14 lists residues in isoform 1 and corresponding residues in isoform 2.

TABLE 14

Residues in isoform 1 and corresponding residues in isoform 2

| Gal-9 Isoform 1 (SEQ ID NO: 1; NCBI GenBank Accession No. BAB83625.1) | Gal-9 Isoform 2 (SEQ ID NO: 2; UniProt ID O00182-2) |
|---|---|
| W309 | W277 |
| R253 | R221 |
| R271 | R239 |
| R334 | R302 |
| R341 | R309 |
| L311 | L279 |
| S240 | S208 |
| L242 | L210 |
| A320 | A288 |
| L242 | L210 |
| S244 | S212 |
| S307 | S275 |
| K318 | K286 |
| A320 | A288 |
| V321 | V289 |

The epitope mapping results described above suggest that the binding of G9.2-17 may not directly interfere with the carbohydrate recognition of galectin-9. To further functionally validate the position of the epitope, the interaction between galectin-9 CRD2 and human muscle-specific kinase (MuSK) extracellular region (ECR) was examined (Cantor et al. PMID 29460776) in an in vitro binding assay using CRD2 monomers. MuSK ECR is not known as a specific binding partner of galectin-9 and thus it serves as a model for non-specific interaction between galectin-9 and glycoproteins.

MuSK ECR was immobilized on beads and binding of galectin-9 CRD2 was detected. Briefly, Dynabeads M-280 Streptavidin (Thermofisher 11205D) were diluted 1:100 into TBS-B, placed on magnetic rack, supernatant removed and resuspended with fresh TBS-B to the original diluted volume. 1.5 bead volumes of biotinylated glycoprotein at 10 nM in TBS-B were prepared, and the beads were incubated with protein solution at 4° C., rotating, for 30 min. Beads were placed on magnetic stand and washed with TBS-B, resuspended and 50 μM biotin was added, then beads were incubated at 4° C., rotating, for 15 min. 3-fold dilutions of G9.2-17 starting with 1000 nM in 200 nM of human Galectin-9 CRD2 in either TBS-B or TBS-B+25 mM Lactose were prepared. Beads were placed on magnetic stand and washed with TBS-B, and resuspended to 2× original diluted bead volume. 20 μL of bead solution was added to each well. Liquid was removed with vacuum manifold and 100 μL of corresponding IgG-Galectin-9 sample was added to each well. Plates were incubated for 30 min on shaker and then washed 3× with TBS-B using vacuum manifold. 20 μL of neutravidin-650 conjugate, diluted 1:100 in TBS-B was added to each well, and plates were incubated at 4° C. in the dark for 30 min and washed 3× with TBS-B using the vacuum manifold. Note: Galectin-9 CRD2 concentration remains fixed in all antibody dilutions. Samples were run on flow cytometer. Each data point was performed in triplicate.

In this assay, weak but significant binding of galectin-9 CRD2 monomer to MuSK. This interaction was abrogated with the addition of lactose, indicating that the interaction is carbohydrate dependent (FIG. 18). In contrast, at relatively high concentrations, the addition of G9.2-17 antibody increased, rather than inhibited, the binding of galectin-9 CRD2 to immobilized MuSK ECD (FIG. 18). As G9.2-17 was added, the binding was reduced. The increase observed at higher concentrations is likely to be due to the antibody capturing two galectin-9 CRD2 molecules, producing a bivalent galectin-9 CRD2 molecule and increasing effective affinity ("avidity effect") (FIG. 19). Indeed, the binding signal is the greatest when the stoichiometric ratio between galectin-9 CRD2 and G9.2-17 approaches 2:1. Again, galectin-9 CRD2 binding in the presence of G9.2-17 can be abrogated with the addition of lactose. These results confirm the prediction from epitope mapping that G9.2-17 does not interfere directly with the carbohydrate-binding function of galectin-9 CRD2, as shown in this in vitro setting.

Example 12: Anti-Galectin-9 Antibody Stability Study

The candidate IgG4 antibody underwent stability analysis after storage under several different conditions and at different concentrations. Stability analysis was performed via size exclusion chromatography (SEC) using a TOSOH TSKgel Super SW mAb column. SEC profiles before and after storage were compared to identify any issues with protein stability (e.g., aggregation or degradation).

Materials and Methods

Sample Preparations

The anti-Galectin-9 antibody was stored at −80° C. until use. Prior to analysis, samples were thawed in a room temperature water bath and stored on ice until analysis. Prior to handling, absorbance at 280 nm was measured using Nanodrop. The instrument was blanked using TBS (20 mM Tris pH 8.0, 150 mM NaCl). The sample was then transferred to polypropylene microcentrifuge tubes (USA Scientific, 1615-5500) and centrifuged at 4° C., 16.1 k×g for 30 min. Samples were filtered through a 0.22 m filter (Millipore; SLGV004SL). Post-filtration absorbance was measured.

HPLC Analysis

Sample conditions tested included the following: ambient stability (0 hr at room temperature, 8 hours at room temperature), refrigerated stability (0 hours at 4° C., 8 hours at 4° C., 24 hours at 4° C.), and freeze/thaw stability (1× freeze/thaw, 3× freeze/thaw, 5× freeze/thaw). Each condition was run in duplicate at three different concentrations: stock, 10× dilution, and 100× dilution. One hundred L samples were prepared for each condition and stored in a polypropylene microcentrifuge tube. Dilutions were prepared in TBS when necessary. Absorbance at 280 nm was read prior to analysis. Room temperature samples were stored on the benchtop for the durations indicated. 4° C. samples were either stored on ice or in 4° C. refrigerator for the periods indicated in Table 15. Freeze-thaw samples were snap-frozen in liquid nitrogen and then thawed in a room temperature water bath. The freeze and thaw process was performed either once, three or five times, and then the samples were stored at 4° C. until analysis.

SEC analysis was performed using a TOSOH TSKgel SuperSW mAb HR column on a Shimadzu HPLC with a UV detector at 280 nm. The columns were loaded with 25 μL of sample and run at 0.5 mL/min for 40 minutes. The KBI buffer formulation was used as the mobile phase.

Results

The concentrations of the antibody were determined using UV absorbance measurements before and after filtration, as shown in Table 15. Two 2 mL samples supplied by KBI were thawed, one vial for use in room temperature and freeze/thaw conditions, and the other vial for use in the 4° C. conditions. Absorbance readings showed nearly complete recovery after filtration.

TABLE 15

Protein Recovery after Sample Preparation

| Vial | Read | Pre-Filtration (mg/mL) | Post-Filtration (mg/mL) | Recovery (%) |
|---|---|---|---|---|
| 1 | 1 | 9.574 | 9.416 | 98.4 |
| (Used for RT and | 2 | 9.435 | 9.553 | 101.3 |
| Freeze/Thaw) | 3 | 9.504 | 9.541 | 100.4 |
| | Average | 9.50 ± 0.07 | 9.50 ± 0.07 | 100.0 ± 1.5 |
| 2 | 1 | 9.618 | 9.401 | 98.6 |
| (Used for 4° C.) | 2 | 9.814 | 9.704 | 98.9 |
| | 3 | 9.451 | 9.394 | 99.4 |
| | Average | 9.63 ± 0.18 | 9.53 ± 0.16 | 98.9 ± 0.4 |

Two or three high molecular weight peaks that eluted earlier than the main peak were observed (FIG. 21). These peaks comprised approximately 500 of the total sample under each condition assayed (Table 16). No significant differences in protein concentration were observed under all assayed conditions.

TABLE 16

Stability Results

| Condition | Time | Dilution | Sample | Concentration (mg/mL) | High Molecular Weight Peaks 1 | 2 | 3 | Total | Main |
|---|---|---|---|---|---|---|---|---|---|
| Room | 0 hr | 1 | 1 | 9.3 ± 0.3 | 0.06 | 3.024 | 4.307 | 7.39 | 92.61 |
| Temperature | | | 2 | 9.36 ± 0.03 | 0.615 | 0.273 | 3.822 | 4.71 | 95.29 |
| | | 10 | 1 | 0.96 ± 0.012 | 0.34 | 1.18 | 3.183 | 4.70 | 95.30 |
| | | | 2 | 1.00 ± 0.02 | 0.418 | 1.225 | 2.541 | 4.18 | 95.82 |
| | | 100 | 1 | 0.147 ± 0.003 | 0.25 | 2.1278 | 2.472 | 4.85 | 95.15 |
| | | | 2 | 0.14 ± 0.05 | 0.17 | 1.507 | 2.684 | 4.36 | 95.64 |

TABLE 16-continued

| Stability Results | | | | | | | | | |
|---|---|---|---|---|---|---|---|---|---|
| | | Dilution | | Concentration | High Molecular Weight Peaks | | | | |
| Condition | Time | Sample | | (mg/mL) | 1 | 2 | 3 | Total | Main |
| | 8 hr | 1 | 1 | 9.5 ± 0.19 | 0.597 | 1.41 | 1.997 | 4.00 | 96.00 |
| | | | 2 | 9.46 ± 0.04 | 0.501 | 1.219 | 2.147 | 3.87 | 96.13 |
| | | 10 | 1 | 1.03 ± 0.02 | 0.413 | 1.173 | 2.51 | 4.10 | 95.90 |
| | | | 2 | 1.026 ± 0.002 | 0.367 | 1.22 | 2.592 | 4.18 | 95.82 |
| | | 100 | 1 | 0.14 ± 0.012 | 0.839 | 1.584 | 2.342 | 4.77 | 95.24 |
| | | | 2 | 0.104 ± 0.008 | 0.723 | 1.578 | 2.719 | 5.02 | 94.98 |
| 4° C. | 1 hr | 1 | 1 | 9.68 ± 0.05 | 0.623 | 1.489 | 2.066 | 4.18 | 95.82 |
| | | | 2 | 9.6 ± 0.15 | 0.463 | 1.617 | 2.999 | 5.08 | 94.92 |
| | | 10 | 1 | 0.96 ± 0.03 | 0.436 | 1.122 | 2.438 | 4.00 | 96.00 |
| | | | 2 | 0.96 ± 0.02 | 0.432 | 1.173 | 2.799 | 4.40 | 95.60 |
| | | 100 | 1 | 0.106 ± 0.003 | 0.503 | 1.834 | 2.73 | 5.07 | 94.93 |
| | | | 2 | 0.103 ± 0.004 | 0.538 | 1.603 | 2.789 | 4.93 | 95.07 |
| | 8 hr | 1 | 1 | 9.59 ± 0.07 | 0.285 | 1.135 | 2.699 | 4.12 | 95.88 |
| | | | 2 | 9.87 ± 0.010 | 0.382 | 0.85 | 2.74 | 3.97 | 96.03 |
| | | 10 | 1 | 0.99 ± 0.015 | 1.342 | 1.168 | 2.647 | 5.16 | 94.84 |
| | | | 2 | 0.98 ± 0.03 | 0.901 | 1.79 | 2.547 | 5.24 | 94.76 |
| | | 100 | 1 | 0.100 ± 0.002 | 0 | 1.768 | 4.856 | 6.62 | 93.38 |
| | | | 2 | 0.097 ± 0.003 | 0 | 0.98 | 3.653 | 4.63 | 95.37 |
| | 24 hr | 1 | 1 | 9.60 ± 0.04 | 0.466 | 1.563 | 2.988 | 5.02 | 94.98 |
| | | | 2 | 9.68 ± 0.08 | 0.491 | 1.166 | 2.521 | 4.18 | 95.82 |
| | | 10 | 1 | 0.973 ± 0.005 | 0.579 | 1.095 | 2.888 | 4.56 | 95.44 |
| | | | 2 | 0.98 ± 0.04 | 0.36 | 1.106 | 2.488 | 3.95 | 96.05 |
| | | 100 | 1 | 0.097 ± 0.001 | 0.588 | 1.413 | 2.95 | 4.95 | 95.05 |
| | | | 2 | 0.099 ± 0.002 | 0.587 | 1.463 | 2.886 | 4.94 | 95.06 |
| Freeze Thaw | 1x | 11 | 1 | 9.5 ± 0.10 | 0.439 | 1.143 | 2.292 | 3.87 | 96.13 |
| | | | 2 | 9.04 ± 0.08 | 0.489 | 1.597 | 2.58 | 4.67 | 95.33 |
| | | 10 | 1 | 1.09 ± 0.03 | 0.388 | 1.228 | 2.741 | 4.36 | 95.64 |
| | | | 2 | 1.08 ± 0.05 | 0.387 | 1.243 | 2.932 | 4.56 | 95.44 |
| | | 100 | 1 | 0.12 ± 0.010 | 0.467 | 1.207 | 2.355 | 4.03 | 95.97 |
| | | | 2 | 0.11 ± 0.011 | 0.627 | 1.65 | 3.09 | 5.37 | 94.63 |
| | 3x | 1 | 1 | 8.1 ± 0.8 | 0.478 | 1.152 | 1.791 | 3.42 | 96.58 |
| | | | 2 | 9.0 ± 0.7 | 0.5 | 1.18 | 1.99 | 3.67 | 96.33 |
| | 5x | 1 | 1 | 8.9 ± 0.6 | 0.505 | 1.578 | 2.612 | 4.70 | 95.31 |
| | | | 2 | 8.6 ± 0.4 | 0.464 | 1.662 | 3.008 | 5.13 | 94.87 |

In summary, the anti-Galectin-9 antibody G92-17 showed consistent stability after storage under all conditions analyzed, as indicated by no significant change in the SEC profile. There was no significant loss of protein after filtration, and two to three high molecular weight peaks were identified, comprising approximately 5% of the total sample. The results suggest that the antibody is stable under all conditions tested, with no aggregate formation or degradation observed.

Example 13: In Vitro and In Vivo Characterization of Anti-Gal9 Antibody G9.2-17

In vivo and in vitro pharmacodynamics and pharmacology studies and safety pharmacology were conducted as disclosed below. In vivo studies were conducted with an IgG1 version of anti-galectin-9 mAb G9.2-17 for mouse studies based on the fact that this antibody was developed to have the exact same $V_H$ and $V_L$ chains and thus the exact same binding epitope as G9.2-17 and the same cross reactivity profile as well as binding affinities across species and same functional profile like G9.2-17.

In Vitro Pharmacology

In vitro assays encompass: non cell-based bead-, ELISA and BIACore surface plasmon resonance (SPR) affinity binding assays, competition ELISA functional blocking assay, cell based flow cytometry binding, a T-cell based apoptosis assay, species cross-reactivity, galectin-9 CRD1 versus CRD2 bead based epitope distinction, as well as patient tumor culture model functional assessment.

Preclinical in vitro pharmacology studies have been conducted to confirm binding affinity of G9.2-17 to galectin-9, and these were performed in a non-cell based format utilizing CRD2 domain specifically, as well as in a cell based format where binding of G9.2-17 was captured to the surface of cancer cell bound galectin-9. Affinity of G9.2-17 in both non-cell based and cell based assays was <1 nMol, while binding was specific to CRD2 domain, with no cross reactivity to CRD1. G9.2-17 binds CRD2 domain of galectin-9 across four species tested (human, rat, mouse and monkey) with equivalent binding affinity of <1 nmol (FIGS. 16A-16D).

Finally, studies to understand the mechanism of action included ADCC/ADCP (antibody dependent cell mediated cytotoxicity/antibody-dependent cellular phagocytosis) and blocking function assessment. As expected for a human IgG4 mAb, G9.2-17 does not mediate ADCC or ADCP (FIG. 22A). This was tested against the IgG1 human counterpart of G9.2-17 as a positive control, which mediates ADCC and ADCP, as expected (FIG. 22B).

Furthermore, blocking function of G9.2-17 was evaluated in a competition binding ELISA assay. G9.2-17 potently blocks binding of galectin-9 CRD2 domain to its binding partner CD206 human recombinant protein, confirming the intended mode of action for G9.2-17, which is to block galectin-9 activity. Moreover, we optimized a MOLM-13 T cell apoptosis assay where G9.2-17 proficiently rescues the cells from apoptosis caused by galectin-9 protein treatment (~50% apoptosis with galectin-9 treatment and ~10% apoptosis with galectin-9+G9.2-17 treatment).

Further extensive in vitro characterization has been done to compare binding and functional characteristics of G9.2-17 to the mouse IgG1 G9.2-17 mAb, which contains exactly the same CDR domains as G9.2-17, hence has the same binding epitope, i.e., CRD2 galectin-9 domain. mIgG1 G9.2-17 was developed for use in mouse syngeneic pharmacology efficacy studies, to avoid any potential development of immunogenicity with G9.2-17 itself. mIgG1 G9.2-17 has equivalent <1 nmol affinity across species, as well as the same cell based binding affinity to human cancer cell line, CRL-2134. mIgG1 G9.2-17 produces equivalent data in the MOLM-13 T cell apoptosis assay, as G9.2-17 itself.

In Vivo Pharmacology

In vivo assays include syngeneic mouse models conducted using a mouse mAb-G9.2-17 binding epitope cloned into an IgG1 mouse backbone (G9.2-17 surrogate mAb for animal efficacy studies), which shares the cross reactivity and binding affinity characteristics of G9.2-17.

Syngeneic mouse models tested were:

Orthotopic pancreatic adenocarcinoma (KPC) mouse model (single agent and in combination with anti-PD-1): tumor volume assessment and flow cytometry;

Subcutaneous melanoma B16F10 model (single agent and in combination with anti-PD-1): tumor volume assessment and flow cytometry.

Subcutaneous MC38 model (single agent and in combination with anti-PD-1): tumor volume assessment G9.2-17 has multi-species cross-reactivity (human, mouse, rat, cynomolgus monkey), with equivalent <1 nmol binding affinities, as assessed in vitro. (FIGS. 16A-16D). G9.2-17 does not cross react with the CRD1 domain of galectin-9 protein. It has excellent stability and purification characteristics, and no cross-reactivity to any of the other galectin proteins that exist in primates.

Table 17 below summarizes results from in vitro pharmacology studies.

TABLE 17

| In Vitro Primary Pharmacodynamics | | |
|---|---|---|
| Objective | Assays | Key Results |
| Bead based binding-human | Binding of G9.2-17 to CRD1 and CRD2 domain of human galectin-9 | Bead based measurements of G9.2-17 binding to the human galectin-9 CRD1 and CRD2 domains show that G9.2-17 is specific to only the human CRD2 domain of galectin-9. The mouse IgG1 version of G9.2-17 show similar specificity to only the CRD2 domain of galectin-9. KD Values (nM): G9.2-17 = 0.15 ± 0.02, G9.2-17 mIgG1 = 0.18 ± 0.02. |
| Bead based binding-mouse | Binding of G9.2-17 to CRD2 domain of mouse galectin-9 | Bead based measurements of G9.2-17 binding to the mouse galectin-9 CRD2 domain show that G9.2-17 binds with <1 nMol to the mouse CRD2 domain. The mouse IgG1 version of G9.2-17 show similar affinity to the CRD2 domain of mouse galectin-9. KD Values (nM): G9.2-17 = 0.30 ± 0.03; G9.2-17 mIgG1 = 0.30 ± 0.1. |
| Bead based binding-rat | Binding of G9.2-17 to CRD2 domain of rat galectin-9 | Bead based measurements of G9.2-17 binding to the rat galectin-9 CRD2 domain show that G9.2-17 binds with <1 nMol to the rat CRD2 domain. The mouse IgG1 version of G9.2-17 show similar affinity to the CRD2 domain of rat galectin-9. KD Values (nM): KD Values (nM): G9.2-17 = 0.31 ± 0.06; G9.2-17 mIgG1 = 0.35 ± 0.06. |
| Bead based binding-cynomolgus monkey | Binding of G9.2-17 to CRD2 domain of cynomolgus monkey galectin-9 | Bead based measurements of G9.2-17 binding to the cynomolgus galectin-9 CRD2 domain show that G9.2-17 binds with <1 nMol to the cynomolgus CRD2 domain. The mouse IgG1 version of G9.2-17 show similar affinity to the CRD2 domain of cynomolgus galectin-9. KD Values (nM): G9.2-17 = 0.31 ± 0.03; G9.2-17 mIgG1 = 0.30 ± 0.10. |
| Binding-ELISA | ELISA based binding assessment of G9.2-17 to human CRD2 domain of galectin-9 | G9.2-17 binding to human Galectin-9 CRD2 was assessed in ELISA format over a concentration range. G9.2-17 was titrated over immobilized Galectin-9 CRD2 and the resultant saturation curve indicates that G9.2-17 has <1 nMol to the CRD2 domain of galectin-9.<br>The mouse IgG1 version of G9.2-17 show similar affinity to the CRD2 domain of galectin-9 when assayed in this format.<br>KD Values (nM): G9.2-17 = 0.42 ± 0.07; G9.2-17 mIgG1 = 0.45 ± 0.04. |
| Binding-SPR human | SPR based binding assessment of G9.2-17 to human CRD2 domain of galectin-9 | SPR measurements using the OneStep method on a Pioneer SPR showed high binding of G9.2-17 to human galectin-9 CRD2. The resultant binding between the antibody and immobilized human galectin-9 CRD2 had no measurable off rate even after continued dissociation for over 30 minutes. This suggests that G9.2-17 has a KD below the measurable limit of assay. The mouse IgG1 version of G9.2-17 showed similar behavior, with no measurable off rate even over an extended dissociation time. KD Values (nM): G9.2-17 = below limit of detection; G9.2-17 mIgG1 = below limit of detection. |

TABLE 17-continued

| In Vitro Primary Pharmacodynamics | | |
|---|---|---|
| Objective | Assays | Key Results |
| Binding-SPR mouse | SPR based binding assessment of G9.2-17 to mouse CRD2 domain of galectin-9 | SPR measurements using the OneStep method on a Pioneer SPR showed high binding of G9.2-17 to mouse galectin-9 CRD2. Binding of G9.2-17 to mouse galectin-9 CRD2 had a KD value of 1.8 ± 0.4 nM. The mouse IgG1 version of G9.2-17 showed similar behavior, with a KD-value of 3.05 ± 0.03 nM. KD Values (nM): G9.2-17 = 1.8 ± 0.4; G9.2-17 mIgG1 = 3.05 ± 0.03. |
| Binding-Cell-based | Assessment of cell surface based (CRL-2134 cell line) binding of G9.2-17 | An assessment of G9.2-17 binding to galectin-9 on the cell surface was performed using the galectin-9 positive CRL-2134 cell line. First, staining of CRL2134 with G9.2-17 showed increased signal compared to staining of the galectin-9 negative HEK-293 cell line. A saturation curve was then generated by titrating G9.2-17 for surface staining of CRL-2134 cells. The curve was generated based on the fraction of the cell population that were positive for galectin-9 as compared unstained cells. Using the generated saturation curve, a cell based KD of 0.41 ± 0.07 nM was calculated. This assay was also performed with the mouse IgG1 variant of G9.2-17 with a resulting cell-based KD of 2.9 ± 0.7 nM. See also FIG. 12. |
| Cell-based potency T-cell apoptosis | G9.2-17 potency assessment using MOLM-13 T cell-based apoptosis assay | MOLM-13 cells are sensitive to high concentrations of human galectin-9. Incubation of MOLM-13 cells for 16 h in the presence of 200 nM galectin-9 results in significant cell death. The addition of G9.2-17 protects MOLM-13 from galectin-9 mediated cell death in a dose dependent manner, significantly reducing the population of necrotic cells. This effect is specific for G9.2-17 as well as the mouse IgG1 variant of G9.2-17 while the matched human IgG4 and mouse IgG1 isotypes show no protection against galectin-9 mediated cell death. |
| Non-cell based potency T-cell apoptosis | G9.2-17 potency assessment using non-cell based, competition ELISA CD206 binding assay | The receptor-ligand interaction between CD206 and galectin-9 was assayed in ELISA format. Full length galectin-9 was immobilized and recombinant, His-tagged CD206 was titrated to confirm CD206 does bind to galectin-9. In order to determine whether or not G9.2-17 blocked the binding between galectin-9 and its native receptor CD206, a competitive ELISA assay was utilized. Blockade of the galectin-9-CD206 interaction resulted in reduced ELISA signal compared to the unblocked condition in a dose dependent manner. |
| Functional assay: non-cell based ADCC/ADCP assay | Bead based ADCC/ADCP assay | G9.2-17 does not mediate ADCC or ADCP activity. |
| Protein array-cross reactivity | Protein Array-Cross reactivity | HuProt ™ array was used for the High-Spec ® antibody cross-reactivity assay. Arrays contained native and not denatured proteins. G9.2-17 recognized galectin-9 (CDI clone or the positive control antigen) as the top hit with high affinity. |
| Expression | Assessing cell surface and intra-cellular galectin-9 levels by flow cytometry on permeabilized and non permeabilized mouse pancreatic cancer (KPC) cells | Dose dependent effect was observed in detection of cell surface galectin-9 on KPC cells, peaking at 20% using 60 nM G9.2-17 Fab. Intracellular galectin-9 expression was uniformly detected in 10% of the cells at 15 nM, 30 nM and 60 nM of G9.2-17 Fab. |
| Expression | Assessing cell surface and intra-cellular galectin-9 levels by flow cytometry on permeabilized and non permeabilized mouse melanoma (B16F10) and colorectal cancer (MC38) cells | 27.6% of B16F10 express galectin-9 on their surface and 98.8% intracellularly. 6.9% of MC38 express galectin-9 on their surface and 41.5% intracellularly. |
| Mechanism of Action | Patient derived tumor cultures ex vivo (organoids) treated with G9.2-17 | Activation of T cells measured through IFNg, TNFα and CD44. n = 20 tumors processed. T cell reactivation from baseline observed in n = 12 out of 20 (60%) of tumors processed. |

TABLE 17-continued

| In Vitro Primary Pharmacodynamics | | |
|---|---|---|
| Objective | Assays | Key Results |
| Expression | Patient derived tumor cultures ex vivo (organoids) profiling for galectin-9 expression on T cells, tumor cells and macrophages | T cells galectin-9 expression (12.5-63.7% CD3+ CD45+ intra PTOD T cells). Myeloid cell galectin-9 expression (15-45.9% CD45+ CD11b+ intra PDOT myelod cells). Tumor cell galectin-9 expression (9.15-33.5% CD45-EpCAM + intra PDOT tumor cells) n = 6 PDOTs |
| Expression | Measuring galectin-9 levels in serum of healthy controls and cancer patients | Sera from healthy controls (n = 16) and cancer patients (n = 22; n = 10 primary and n = 12 metastatic) with gastrointestinal malignancies. Galectin-9 serum levels are significantly increased in cancer patients vs controls (p = 0.001) |
| Expression | Measuring galectin-9 levels in serum and plasma of healthy controls and cancer patients | Sera and plasma from healthy controls (n = 10) and cancer patients (n = 10) with metastatic tumors of diverse site of origin was tested for galectin-9 expression. |

Further, patient-derived tumor cultures ex vivo (organoids) treated with G9.2-17 are to be used for exploring mechanism of action of G9.2-17.

Mechanistically, G9.2-17 was found to have blocking activity and not ADCC/ADCP activity. Blocking of galectin-9 interactions with its binding receptors, such as CD206 on immunosuppressive macrophages, is observed. Functionally, in vivo studies demonstrated reduction of tumor growth in multiple syngeneic models treated with G9.2-17 mIgG1 surrogate antibody (orthotopic pancreatic KPC tumor growth and s.c. melanoma B16F10 model). In mouse tumors treated with single agent anti-galectin-9 mAb and in combination with anti-PD-1, G9.2-17 reactivates effector T cells and reduces levels of immunosuppressive cytokines. 10 Combination studies with an anti-PD-1 mAb suggest higher intra-tumoral presence of effector T cells, supporting clinical testing of the combinatorial approach. Importantly, mechanistic effects of G9.2-17 have been investigated and demonstrated in patient derived tumor cultures (Jenkins et al., 2018) (tumor excisions from primary and metastatic sites from PDAC, CRC, CCA, HCC), where G9.2-17 induces reproducible and robust T cell reactivation, indicating reversal of galectin-9 imposed intra-tumoral immunosuppression ex vivo.

In order to assess relevance of combining anti-PD-1 and anti-galectin-9 mAbs, s.c. melanoma B16 model was treated with single agent anti-PD-1 and anti-galectin-9 as well as the combination. Intra-tumoral presence effector T cells were enhanced in the combination arm.

Significant increases in the level of cytotoxic T cells (CD8) are observed in treatments 20 with anti-galectin-9 mIgG1 200 μg+anti-PD-1 (p<0.001) compared to that of anti-galectin-9 mIgG1 200 μg, and between anti-galectin-9 IgG1 200 μg+anti-PD-1 compared to anti-PD-1 alone (p<0.01). Such results suggest that anti-Gal9 antibody and anti-PD-1 antibody in combination would be expected to achieve superior therapeutic effects.

Table 18 below summarizes results from in vivo pharmacology studies.

TABLE 18

| In Vivo Primary Pharmacodynamics | | |
|---|---|---|
| Study Title | Test System | Key Results |
| Efficacy study assessing tumor volume and flow cytometry of intra-tumoral immune cells in mice treated with IgG1 mouse anti-galectin-9 mAb at 150 μg/dose i.p. | orthotopic KPC model | Efficacy observed with single agent IgG1 mouse galectin-9 mAb, p = 0.05. Flow cytometry: CD8 T cells: Increase in CD8+ T cell TNF alpha (p = 0.027), increase in CD8+ T cell CD44 (p = 0.0008) and reduction in CD8+ T cell IL10 (p = 0.0026). Increase in CD4+ T Cell TNF alpha (p = 0.0007). |
| Efficacy study assessing tumor volume and flow cytometry of intra-tumoral immune cells in mice treated with IgG1 mouse anti-galectin-9 mAb at 200 and 400 μg/dose i.p. | orthotopic KPC model | Efficacy observed at 200 μg (p = 0.0005) and 400 μg (p = 0.01) dose levels of single agent anti-galectin-9 mIgG1 mAb. Flow cytometry: CD8+ T cells: increase of CD44 (for dose levels 200 μg and 400 μg p = 0.002). CD4+ T cells: Increase in CD44 (for dose level 200 μg, p = 0.015 and for dose level 400 μg p = 0.0003). |
| Efficacy study assessing tumor volume and flow cytometry of intra-tumoral immune cells in mice treated with IgG1 mouse anti-galectin-9 mAb at 100 and 200 μg/dose i.p. | orthotopic KPC model | Efficacy observed at both dose levels (p < 0.01). Flow cytometry: CD4+ T cells: increase in CD44 (p < 0.0001), PD-1 (for dose level 100 μg p = 0.005 and for dose level 200 μg p = 0.001); CD8+ T cells: increase in CD44 (p < 0.0001). |

TABLE 18-continued

| In Vivo Primary Pharmacodynamics | | |
|---|---|---|
| Study Title | Test System | Key Results |
| Efficacy study assessing tumor volume in mice treated with IgG1 mouse anti-galectin-9 mAb at 20, 50 and 100 μg/dose i.p. + 100 μg/dose IgG1 mouse anti-galectin-9 mAb with anti-PD-1 | orthotopic KPC model | Efficacy observed at 50 μg ($p < 0.05$) and 100 μg ($p < 0.0001$) dose levels and no significant efficacy at 20 μg/dose. No significant TV synergy effect with combination of 100 μg anti-galectin-9 mAb and anti-PD-1 |
| Efficacy study assessing tumor volume and flow cytometry in mice treated with IgG1 mouse anti-galectin-9 mAb at 200 and 400 μg/dose i.v. + anti-PD-1 mAb | Sub cutaneous B16F10 model | Highest efficacy observed at 200 μg ($p < 0.005$) single agent mouse anti-galectin-9 mAb, superior to anti-PD-1 mAb. No significant TV synergy effect with combination of 200 μg anti-galectin-9 mAb and anti-PD-1 on tumor growth. However, significant increase in cytotoxic CD8 T cell levels were observed in mouse anti-galectin-9 mAb + anti-PD-1 mAb ($p < 0.01$). |
| Efficacy study assessing tumor volume in mice treated with IgG1 mouse anti-galectin-9 mAb at 200 and 400 μg/dose i.v. + anti-PD-1 mAb | Sub cutaneous MC38 model | Efficacy not superior to anti-PD-1 mAb in this model. Combination with anti-PD-1 is equivalent to anti-PD-1 alone. Please refer to CFCH001 for flow cytometry data explaining low expression of galectin-9 on MC38 cells. |

Further, tumor immune responses to treatment with G9.2-17 IgG1 mouse mAb (aka LYT-200 mIgG), anti-PD1 antibody, or a combination of the G9.2-17 IgG1 mouse mAb and anti-PD1 antibody were investigated in the B16F10 subcutaneous syngeneic model described herein. As shown in FIG. 23A and FIG. 23B, the G9.2-17 and anti-PD1 combination showed synergistic effects in reducing tumor volume and in increasing CD8+ cells in the mouse model. FIGS. 24A and 24B show that the G9.2-17 antibody (aka LYT-200) increased CD44 and TNFα expression in intratumoral T cells.

EQUIVALENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An isolated antibody, which binds human galectin-9, wherein the antibody comprises (a) a heavy chain comprising a heavy chain variable region ($V_H$) and a heavy chain constant region, and (b) a light chain comprising a light chain variable region ($V_L$) and a light chain constant region;

wherein the $V_H$ comprises a heavy chain complementarity determining region 1 (CDR1) set forth as SEQ ID NO: 22, a heavy chain complementary determining region 2 (CDR2) set forth as SEQ ID NO: 23, and a heavy chain complementary determining region 3 (CDR3) set forth as SEQ ID NO: 24, wherein the $V_L$ comprises a light chain complementarity determining region 1 (CDR1) set forth as SEQ ID NO: 19, a light chain complementary determining region 2 (CDR2) set forth as SEQ ID NO: 20, and a light chain complementary determining region 3 (CDR3) set forth as SEQ ID NO: 21, wherein the heavy chain constant region comprises the amino acid sequence of SEQ ID NO: 36, and wherein the light chain constant region comprises the amino acid sequence of SEQ ID NO: 37.

2. The isolated antibody of claim 1, wherein the $V_H$ comprises the amino acid sequence of SEQ ID NO: 10 and the $V_L$ comprises the amino acid sequence of SEQ ID NO: 9.

3. The isolated antibody of claim 2, wherein the heavy chain comprises the amino acid sequence of SEQ ID NO: 42 and the light chain comprises the amino acid sequence of SEQ ID NO. 47.

4. A pharmaceutical composition comprising the antibody of claim 1 and a pharmaceutically acceptable carrier.

5. A method of increasing an immune response in a subject having a solid tumor, the method comprising administering to the subject in need thereof an effective amount of a pharmaceutical composition comprising the antibody of claim 1.

6. The method of claim 5, wherein the solid tumor is selected from the group consisting of pancreatic cancer, glioblastoma, glioma, melanoma, skin squamous cell carcinoma, sarcoma, upper and lower gastrointestinal cancers, colorectal carcinoma, metastatic colorectal carcinoma, carcinoid tumors, neuroendocrine tumors, breast cancers, lung cancers, head and neck cancers, and genitourinary cancers.

7. The method of claim 5, wherein increasing the immune response results in CD4+ or CD8+ T cell activation, an increase in TNF-alpha level, an increase in CD44 level, a decrease in IL-10 level, or a combination thereof, as compared to a level of CD4+ or CD8+ T cell activation, TNF-alpha, CD44, and/or IL-10 found prior to administration of the galectin-9 antibody.

8. The method of claim 6, wherein the method further comprises administering to the subject an effective amount of a checkpoint inhibitor and/or a chemotherapeutic agent.

9. The method of claim 8, wherein the checkpoint inhibitor is an anti-PD-1 antibody.

10. The method of claim 8, wherein the chemotherapeutic agent is gemcitabine and/or paclitaxel.

11. A method of increasing the number of intra-tumoral effector T cells in a solid tumor of a subject, the method comprising administering anti-Galectin-9 to the subject in need thereof an effective amount of a pharmaceutical composition comprising the antibody of claim 1.

12. The method of claim 11, wherein the solid tumor is selected from the group consisting of pancreatic cancer, glioblastoma, glioma, melanoma, skin squamous cell carcinoma, sarcoma, upper and lower gastrointestinal cancers, colorectal carcinoma, metastatic colorectal carcinoma, carcinoid tumors, neuroendocrine tumors, breast cancers, lung cancers, head and neck cancers, and genitourinary cancers.

13. The method of claim 11, wherein the method further comprises administering to the subject an effective amount of a checkpoint inhibitor and/or a chemotherapeutic agent.

14. The method of claim 13, wherein the checkpoint inhibitor is an anti-PD-1 antibody.

15. The method of claim 13, wherein the chemotherapeutic agent is gemcitabine and/or paclitaxel.

* * * * *